(12) United States Patent  (10) Patent No.: US 7,884,108 B2
Blomgren et al.  (45) Date of Patent: Feb. 8, 2011

(54) CERTAIN SUBSTITUTED PYRAZINONES

(75) Inventors: Peter A. Blomgren, North Branford, CT (US); Kevin S. Currie, North Branford, CT (US); Seung H. Lee, Branford, CT (US); Scott A. Mitchell, East Haven, CT (US); Jianjun Xu, Branford, CT (US); Aaron C. Schmitt, Hamden, CT (US); Zhongdong Zhao, Guilford, CT (US); Pavel E. Zhichkin, Delmar, NY (US); Douglas G. Stafford, Niskayuna, NY (US); Jeffrey E. Kropf, Branford, CT (US)

(73) Assignee: CGI Pharmaceuticals, Inc., Branford, CT (US)

( * ) Notice: Subject to any disclaimer, the term of this patent is extended or adjusted under 35 U.S.C. 154(b) by 0 days.

(21) Appl. No.: 12/234,281

(22) Filed: Sep. 19, 2008

(65) Prior Publication Data

US 2009/0082330 A1  Mar. 26, 2009

Related U.S. Application Data

(60) Provisional application No. 60/973,995, filed on Sep. 20, 2007, provisional application No. 61/050,777, filed on May 6, 2008.

(51) Int. Cl.
*A61K 31/4965* (2006.01)

(52) U.S. Cl. .............. 514/255.06; 544/121; 544/359; 544/406; 546/268.1; 548/952; 549/29; 549/49; 435/15

(58) Field of Classification Search ............ 514/255.06; 544/121, 359, 406; 546/268.1; 548/952; 549/29, 49
See application file for complete search history.

(56) References Cited

FOREIGN PATENT DOCUMENTS

WO  WO 2006/099075 A2  9/2006
WO  WO 2008/033854 A1  3/2008
WO  WO 2008/033858 A2  3/2008

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*

* cited by examiner

*Primary Examiner*—James O Wilson
*Assistant Examiner*—Douglas M Willis
(74) *Attorney, Agent, or Firm*—Millen, White, Zelano & Branigan, P.C.

(57) ABSTRACT

Compounds of Formula I

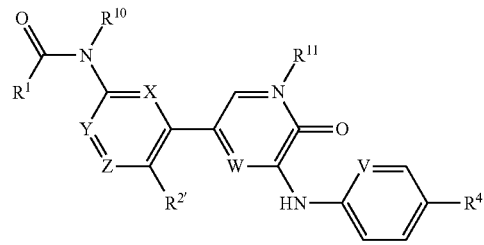

that inhibit Btk are described herein. Pharmaceutical compositions comprising at least one compound of Formula I, together with at least one pharmaceutically acceptable vehicle chosen from carriers, adjuvants, and excipients, are described. Methods of treating patients suffering from certain diseases responsive to inhibition of Btk activity and/or B-cell activity are described. Methods for determining the presence of Btk in a sample are described.

44 Claims, No Drawings

CERTAIN SUBSTITUTED PYRAZINONES

This application claims priority under 35 U.S.C. §119(e), U.S. Provisional Application No. 60/973,995 filed Sep. 20, 2007, and U.S. Provisional Application No. 61/050,777 filed May 6, 2008, which are incorporated herein by reference.

Provided herein are certain substituted amides and related compounds, compositions comprising such compounds, and methods of their use.

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis.

A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma. In addition, Btk has been reported to play a role in apoptosis; thus, inhibition of Btk activity can be useful for cancer, as well as the treatment of B-cell lymphoma and leukemia. Moreover, given the role of Btk in osteoclast function, the inhibition of Btk activity can be useful for the treatment of bone disorders such as osteoporosis.

Provided is a compound of Formula I:

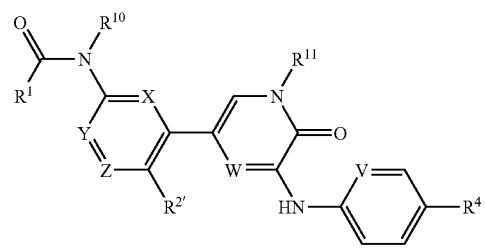

(Formula I)

and pharmaceutically acceptable salts, solvates, and mixtures thereof, wherein

X is chosen from N and $CR^2$;

Y is chosen from N and $CR^{3'}$;

Z is chosen from N and $CR^3$; provided that only one of X, Y and Z is N at a time;

W is chosen from N and CH;

V is chosen from CH and N; provided that one of W and V must be N and W and V are not both N;

$R^1$ is chosen from:

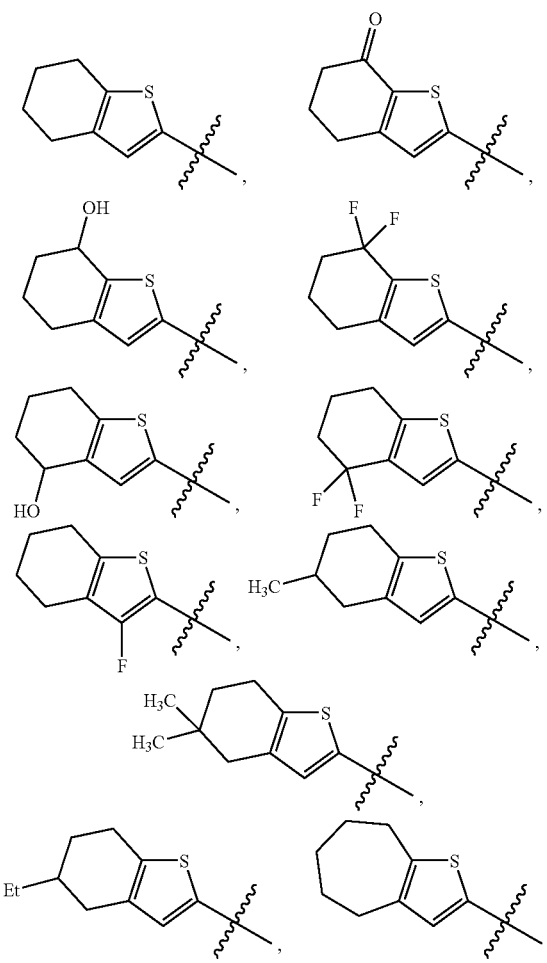

-continued

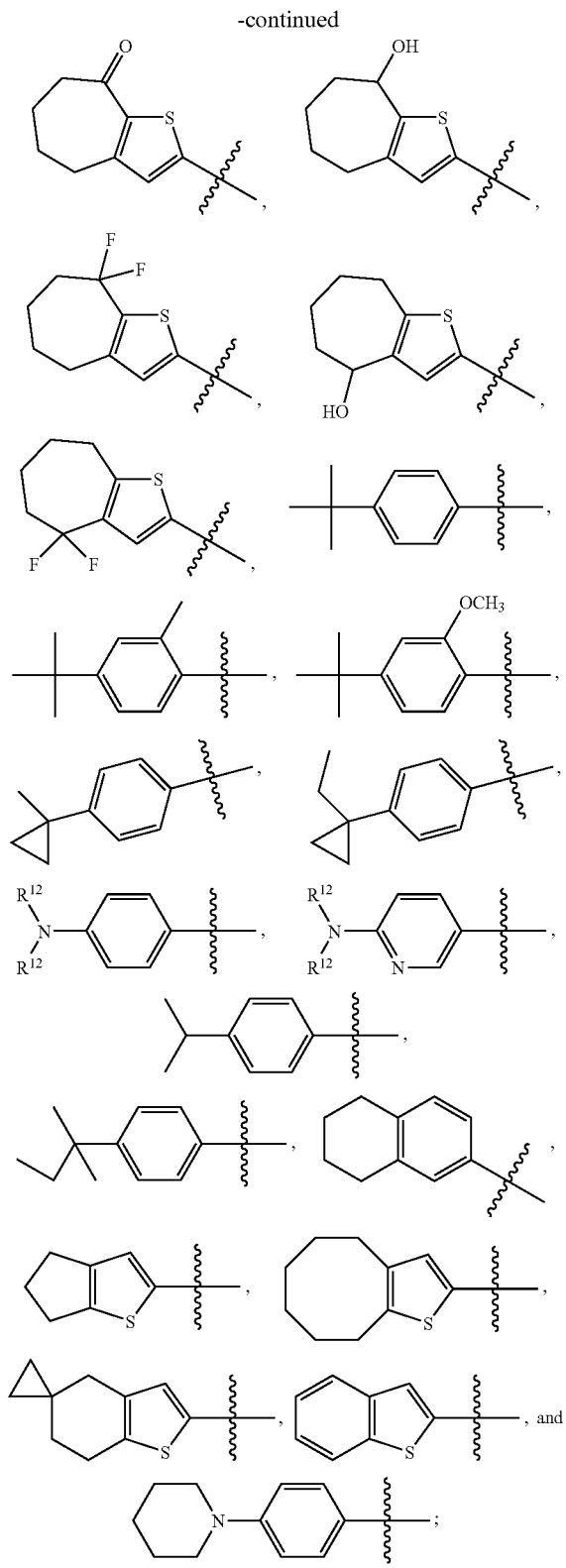

$R^2$ is chosen from H, CH$_3$, F, Cl, CN, OCH$_3$, OH and CF$_3$;
$R^{2'}$ is chosen from H and F;
$R^3$ is chosen from H, CH$_3$, CF$_3$, F, Cl, CN and OCH$_3$;
$R^{3'}$ is chosen from H, CH$_3$, F, Cl, CN and OCH$_3$;

$R^4$ is

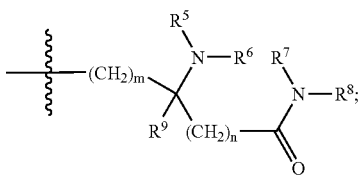

m is chosen from 0 and 1;
n is chosen from 0 and 1;
$R^5$ is chosen from H, C$_1$-C$_6$ alkyl, and C$_3$-C$_6$ cycloalkyl, wherein said alkyl is optionally substituted with one or more substituents chosen from OH, F, and OCH$_3$;
$R^6$ is chosen from H and C$_1$-C$_6$ alkyl; or $R^5$ and $R^6$ are optionally taken together with the nitrogen atom to which they are attached to form a 4- to 6-membered cyclic ring having 0-1 additional N, S or O, wherein the optional additional ring nitrogen is optionally substituted with C$_1$-C$_3$ alkyl and said cyclic ring is optionally substituted with OH;
$R^7$ is chosen from H, C$_1$-C$_6$ alkyl, and C$_3$-C$_6$ cycloalkyl, wherein said alkyl is optionally substituted with one or more substituents chosen from OH and O(C$_1$-C$_4$ alkyl); or $R^6$ and $R^7$ are optionally taken together with the —N(R$^5$)C(R$^9$)(CH$_2$)$_n$C(=O)N(R$^8$)— group through the respective nitrogen atoms to which they are directly attached to form a 6-membered cyclic ring;
$R^8$ is chosen from H and C$_1$-C$_6$ alkyl, wherein said alkyl is optionally substituted with one or more substituents chosen from OH, F, and OCH$_3$; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with C$_1$-C$_3$ alkyl and said cyclic ring is optionally substituted with OH;
$R^9$ is chosen from H and CH$_3$;
$R^{10}$ is chosen from OH, H and C$_1$-C$_3$ alkyl optionally substituted with N(R$^9$)$_2$;
$R^{11}$ is chosen from H, CH$_3$ and CF$_3$; and
$R^{12}$ is C$_1$-C$_3$ alkyl.

Provided is a pharmaceutical composition, comprising a compound of any one of Formulae I-IX, together with at least one pharmaceutically acceptable vehicle chosen from carriers, adjuvants, and excipients.

Provided is a packaged pharmaceutical composition, comprising
a pharmaceutical composition described herein; and
instructions for using the composition to treat a patient suffering from a disease responsive to inhibition of Btk activity.

Provided is a method for treating a patient having a disease responsive to inhibition of Btk activity, comprising administering to the patient an effective amount of a compound of any one of Formulae I-IX.

Provided is a method for treating a patient having a disease chosen from cancer, bone disorders, autoimmune diseases, inflammatory diseases, acute inflammatory reactions, and allergic disorders comprising administering to the patient an effective amount of a compound of any one of Formulae I-IX.

Provided is a method for increasing sensitivity of cancer cells to chemotherapy, comprising administering to a patient undergoing chemotherapy with a chemotherapeutic agent an amount of a compound of any one of Formulae I-IX sufficient to increase the sensitivity of cancer cells to the chemotherapeutic agent.

Provided is a method of reducing medication error and enhancing therapeutic compliance of a patient being treated for a disease responsive to inhibition of Btk activity, the method comprising providing a packaged pharmaceutical preparation described herein wherein the instructions additionally include contraindication and adverse reaction information pertaining to the packaged pharmaceutical composition.

Provided is a method for inhibiting ATP hydrolysis, the method comprising contacting cells expressing Btk with a compound of any one of Formulae I-IX in an amount sufficient to detectably decrease the level of ATP hydrolysis in vitro.

Provided is a method for determining the presence of Btk in a sample, comprising contacting the sample with a compound of any one of Formulae I-IX under conditions that permit detection of Btk activity, detecting a level of Btk activity in the sample, and therefrom determining the presence or absence of Btk in the sample.

Provided is a method for inhibiting B-cell activity comprising contacting cells expressing Btk with a compound of any one of Formulae I-IX in an amount sufficient to detectably decrease B-cell activity in vitro.

As used in the present specification, the following words and phrases are generally intended to have the meanings as set forth below, except to the extent that the context in which they are used indicates otherwise. The following abbreviations and terms have the indicated meanings throughout.

As used herein, when any variable occurs more than one time in a chemical formula, its definition on each occurrence is independent of its definition at every other occurrence. In accordance with the usual meaning of "a" and "the" in patents, reference, for example, to "a" kinase or compound or "the" kinase or compound is inclusive of one or more kinases or compounds. The broken bond 
indicates the point of attachment.

As used herein, "alkyl" encompasses straight chain and branched hydrocarbon chain having the indicated number of carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

As used herein, "modulation" refers to a change in kinase activity as a direct or indirect response to the presence of compounds described herein, relative to the activity of the kinase in the absence of the compound. The change may be an increase in activity or a decrease in activity, and may be due to the direct interaction of the compound with the kinase, or due to the interaction of the compound with one or more other factors that in turn affect kinase activity. For example, the presence of the compound may, for example, increase or decrease kinase activity by directly binding to the kinase, by causing (directly or indirectly) another factor to increase or decrease the kinase activity, or by (directly or indirectly) increasing or decreasing the amount of kinase present in the cell or organism.

Compounds of any one of Formulae I-IX include, but are not limited to, optical isomers of Formulae I-IX, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds include Z- and E-forms (or cis- and trans-forms) of compounds with carbon-carbon double bonds. Where compounds exist in various tautomeric forms, chemical entities of the present invention include all tautomeric forms of the compound. Compounds also include crystal forms including polymorphs and clathrates.

The present invention includes, but is not limited to, compounds of Formulae I-IX and all pharmaceutically acceptable forms thereof. Pharmaceutically acceptable forms of the compounds recited herein include pharmaceutically acceptable salts, solvates, prodrugs, and mixtures thereof. In certain embodiments, the compounds described herein are in the form of pharmaceutically acceptable salts. The compounds of this invention remain part of this invention even when they are in the form of chemical association with other chemical entities in the manner of a chelate or a non-covalent complex. The terms "compound" and "chemical entity" are used interchangeably herein.

"Pharmaceutically acceptable salts" include, but are not limited to, salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compound is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of the present invention, for example ester or amide derivatives of the compounds of any one Formulae I-IX. The term "prodrugs" includes any compounds that become compounds of any one of Formulae I-IX when administered to a patient, e.g., upon metabolic processing of the prodrug. Examples of prodrugs include, but are not limited to, acetate, formate, and benzoate and like derivatives of functional groups (such as alcohol or amine groups) in the compounds of any one of Formulae I-IX.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points. Such a metal ion include $Ca^{++}$ and $Mg^{++}$.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

The term "active agent" is used to indicate a chemical entity which has biological activity. In certain embodiments, an "active agent" is a compound having pharmaceutical utility. For example an active agent may be an anti-cancer therapeutic.

The term "therapeutically effective amount" of a compound of this invention means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Btk activity. In some embodiments, a therapeutically effective amount is an amount sufficient to reduce cancer symptoms, the symptoms of bone disorders, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In certain circumstances a patient suffering from cancer may not present symptoms of being affected. In some embodiments, a therapeutically effective amount of a compound/chemical entity is an amount sufficient to prevent a significant increase or significantly reduce the detectable level of cancerous cells or cancer markers in the patient's blood, serum, or tissues. In methods described herein for treating allergic disorders and/or autoimmune and/or inflammatory diseases and/or acute inflammatory reactions, a therapeutically effective amount may also be an amount sufficient, when administered to a patient, to detectably slow progression of the disease, or prevent the patient to whom the compound/chemical entity is given from presenting symptoms of the allergic disorders and/or autoimmune and/or inflammatory disease, and/or acute inflammatory response. In certain methods described herein for treating allergic disorders and/or autoimmune and/or inflammatory diseases and/or acute inflammatory reactions, a therapeutically effective amount may also be an amount sufficient to produce a detectable decrease in the amount of a marker protein or cell type in the patient's blood or serum. For example, in some embodiments a therapeutically effective amount is an amount of a compound/chemical entity described herein sufficient to significantly decrease the activity of B-cells. In another example, in some embodiments a therapeutically effective amount is an amount of a compound of any one of Formulae I-IX sufficient to significantly decrease the number of B-cells. In another example, in some embodiments a therapeutically effective amount is an amount of a compound of any one of Formulae I-IX sufficient to decrease the level of anti-acetylcholine receptor antibody in a patient's blood with the disease myasthenia gravis.

The term "inhibition" indicates a significant decrease in the baseline activity of a biological activity or process. "Inhibition of Btk activity" refers to a decrease in Btk activity as a direct or indirect response to the presence of a compound of any one of Formulae I-IX, relative to the activity of Btk in the absence of such compound. The decrease in activity may be due to the direct interaction of the compound with Btk, or due to the interaction of such compound with one or more other factors that in turn affect Btk activity. For example, the presence of the compound may decrease Btk activity by directly binding to the Btk, by causing (directly or indirectly) another factor to decrease Btk activity, or by (directly or indirectly) decreasing the amount of Btk present in the cell or organism.

Inhibition of Btk activity also refers to observable inhibition of Btk activity in a standard biochemical assay for Btk activity, such as the ATP hydrolysis assay described below. In some embodiments, a compound of any one of Formulae I-IX has an $IC_{50}$ value less than or equal to 1 micromolar. In some embodiments, a compound of any one of Formulae I-IX has an $IC_{50}$ value less than or equal to less than 25 nanomolar. In some embodiments, a compound of any one of Formulae I-IX has an $IC_{50}$ value less than or equal to 5 nanomolar.

"Inhibition of B-cell activity" refers to a decrease in B-cell activity as a direct or indirect response to the presence of a compound of any one of Formulae I-IX, relative to the activity of B-cells in the absence of such compound. The decrease in activity may be due to the direct interaction of the compound with Btk or with one or more other factors that in turn affect B-cell activity.

Inhibition of B-cell activity also refers to observable inhibition of CD86 expression in a standard assay such as the assay described below. In some embodiments, a compound of any one of Formulae I-IX has an $IC_{50}$ value less than or equal to 10 micromolar. In some embodiments, a compound of any one of Formulae I-IX has an $IC_{50}$ value less than or equal to less than 0.5 micromolar. In some embodiments, a compound of any one of Formulae I-IX has an $IC_{50}$ value less than or equal to 100 nanomolar.

"B cell activity" also includes activation, redistribution, reorganization, or capping of one or more various B cell membrane receptors, e.g., CD40, CD86, and Toll-like receptors TLRs (in particular TLR4), or membrane-bound immunoglobulins, e.g, IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates no increase or any significant decrease in the number of B-cells, either in vitro or in vivo. Thus an inhibition of B-cell proliferation in vitro would be any significant decrease in the number of B-cells in an in vitro sample contacted with a compound of any one of Formulae I-IX as compared to a matched sample not contacted with such compound.

Inhibition of B-cell proliferation also refers to observable inhibition of B-cell proliferation in a standard thymidine incorporation assay for B-cell proliferation, such as the assay described herein. In some embodiments, a compound of any one of Formulae I-IX has an $IC_{50}$ value less than or equal to 10 micromolar. In some embodiments, a compound of any one of Formulae I-IX has an $IC_{50}$ value less than or equal to less than 500 nanomolar. In some embodiments, a compound of any one of Formulae I-IX has an $IC_{50}$ value less than or equal to 50 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p<0.05$.

A "disease responsive to inhibition of Btk activity" is a disease in which inhibiting Btk kinase provides a therapeutic benefit such as an amelioration of symptoms, decrease in disease progression, prevention or delay of disease onset, or inhibition of aberrant activity of certain cell-types (monocytes, osteoclasts, B-cells, mast cells, myeloid cells, basophils, macrophages, neutrophils, and dendritic cells).

"Treatment or treating" means any treatment of a disease in a patient, including:
a) inhibiting the disease;
b) slowing or arresting the development of clinical symptoms; and/or
c) relieving the disease, that is, causing the regression of clinical symptoms.

"Prevent or preventing" a disease means causing the clinical symptoms of the disease not to develop.

"Patient" refers to an animal, such as a mammal, that has been or will be the object of treatment, observation or experiment. The methods of the invention can be useful in both human therapy and veterinary applications. In some embodiments, the patient is a mammal; in some embodiments the patient is human; and in some embodiments the patient is chosen from cats and dogs.

Provided is a compound of Formula I:

(Formula I)

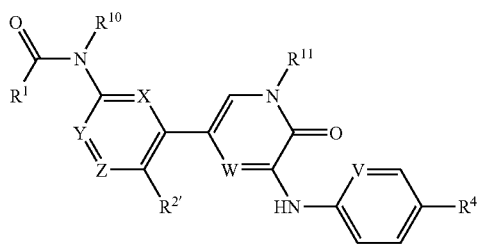

and pharmaceutically acceptable salts, solvates, and mixtures thereof, wherein

X is chosen from N and $CR^2$;

Y is chosen from N and $CR^{3'}$;

Z is chosen from N and $CR^3$; provided that only one of X, Y and Z is N at a time;

W is chosen from N and CH;

V is chosen from CH and N; provided that one of W and V must be N and W and V are not both N;

$R^1$ is chosen from:

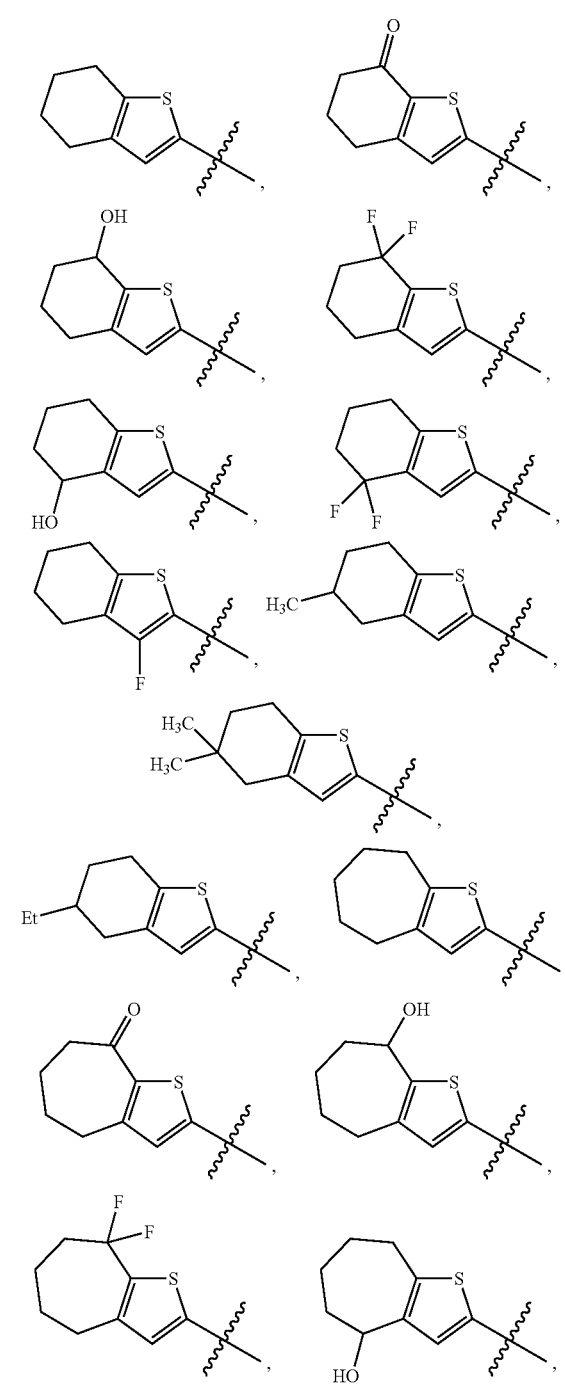

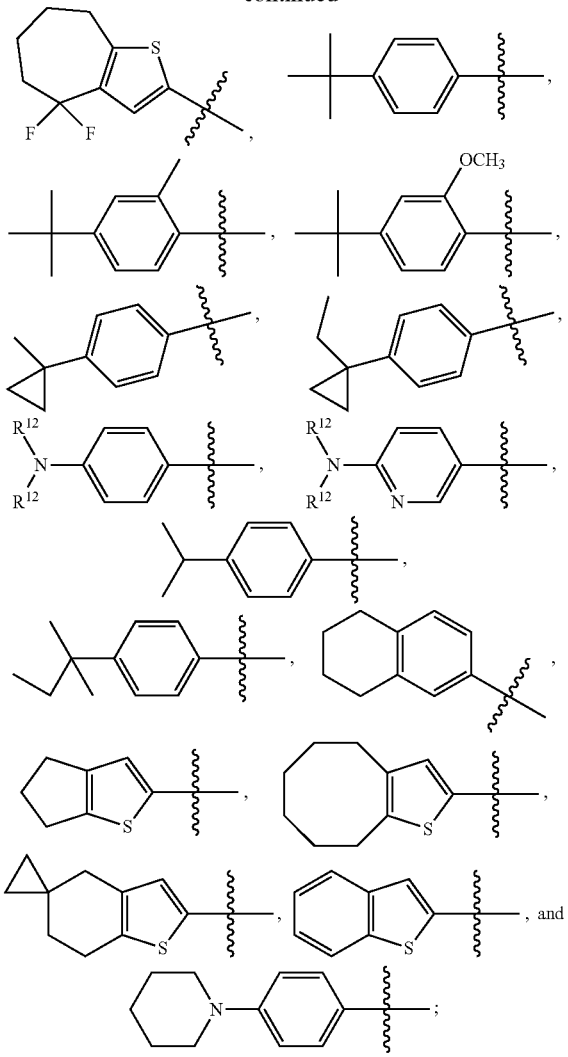

$R^2$ is chosen from H, $CH_3$, F, Cl, CN, $OCH_3$, OH and $CF_3$;
$R^{2'}$ is chosen from H and F;
$R^3$ is chosen from H, $CH_3$, $CF_3$, F, Cl, CN and $OCH_3$;
$R^{3'}$ is chosen from H, $CH_3$, F, Cl, CN and $OCH_3$;
$R^4$ is

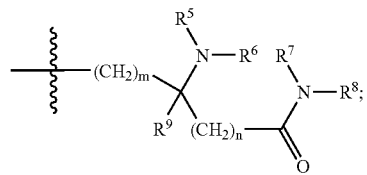

m is chosen from 0 and 1;
n is chosen from 0 and 1;
$R^5$ is chosen from H, $C_1$-$C_6$ alkyl, and $C_3$-$C_6$ cycloalkyl, wherein said alkyl is optionally substituted with one or more substituents chosen from OH, F, and $OCH_3$;
$R^6$ is chosen from H and $C_1$-$C_6$ alkyl; or $R^5$ and $R^6$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl and said cyclic ring is optionally substituted with OH;

$R^7$ is chosen from H, $C_1$-$C_6$ alkyl, and $C_3$-$C_6$ cycloalkyl, wherein said alkyl is optionally substituted with one or more substituents chosen from OH and O($C_1$-$C_4$ alkyl); or $R^6$ and $R^7$ are optionally taken together with the —N($R^5$)C($R^9$)($CH_2$)$_n$C(=O)N($R^8$)— group through the respective nitrogen atoms to which they are directly attached to form a 6-membered cyclic ring;

$R^8$ is chosen from H and $C_1$-$C_6$ alkyl, wherein said alkyl is optionally substituted with one or more substituents chosen from OH, F, and $OCH_3$; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl and said cyclic ring is optionally substituted with OH;

$R^9$ is chosen from H and $CH_3$;
$R^{10}$ is chosen from OH, H and $C_1$-$C_3$ alkyl optionally substituted with N($R^9$)$_2$;
$R^{11}$ is chosen from H, $CH_3$ and $CF_3$; and
$R^{12}$ is $C_1$-$C_3$ alkyl.

In certain embodiments, $R^{11}$ is $CH_3$. In certain embodiments, $R^{11}$ is H.

In certain embodiments, $R^{12}$ is $C_1$-$C_2$ alkyl.

In certain embodiments, W is N and V is CH (Formula I-a, wherein $R^1$, $R^{2'}$, $R^4$, $R^{10}$, X, Y and Z are as defined in Formula I).

(Formula I-a)

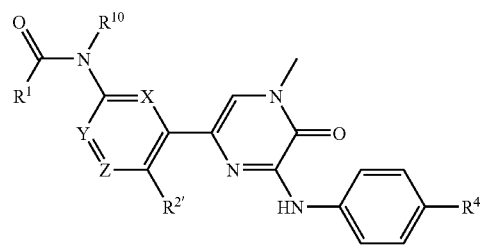

In certain embodiments, W is CH and V is N (Formula I-b, wherein $R^1$, $R^{2'}$, $R^4$, $R^{10}$, X, Y and Z are as defined in Formula I).

(Formula I-b)

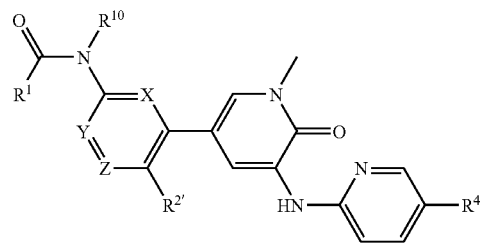

In certain embodiments, X is $CR^2$.

In certain embodiments, the compounds of the present invention are of Formula II wherein $R^1$, $R^2$, $R^{2'}$, $R^4$, $R^{10}$, Y and Z are as defined in Formula I.

(Formula II)

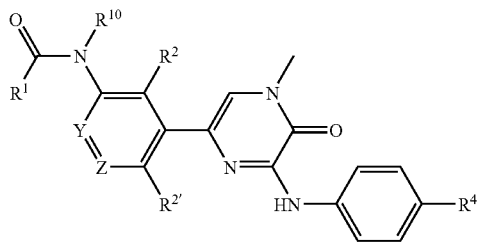

In certain embodiments, X is N.

In certain embodiments, the compounds of the present invention are of Formula III wherein $R^1$, $R^{2'}$, $R^3$, $R^{3'}$, $R^4$, and $R^{10}$ are as defined in Formula I.

(Formula III)

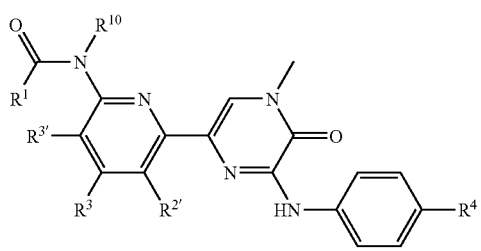

In certain embodiments, Y is $CR^{3'}$.

In certain embodiments, the compounds of the present invention are of Formula IV wherein $R^1$, $R^2$, $R^3$, $R^4$, $R^{10}$, X and Z are as defined in Formula I.

(Formula IV)

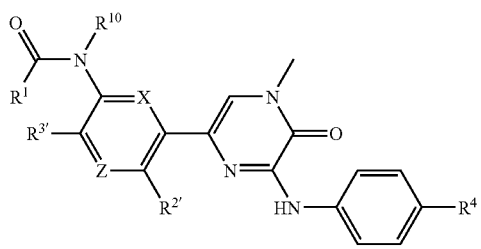

In certain embodiments, Y is N.

In certain embodiments, the compounds of the present invention are of Formula V wherein $R^1$, $R^2$, $R^{2'}$, $R^3$, $R^4$, and $R^{10}$ are as defined in Formula I.

(Formula V)

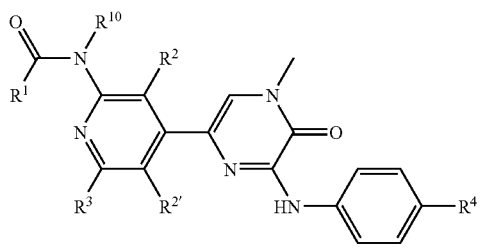

In certain embodiments, Z is $CR^3$.

In certain embodiments, the compounds of the present invention are of Formula VI wherein $R^1$, $R^{2'}$, $R^3$, $R^4$, $R^{10}$, X and Y are as defined in Formula I.

(Formula VI)

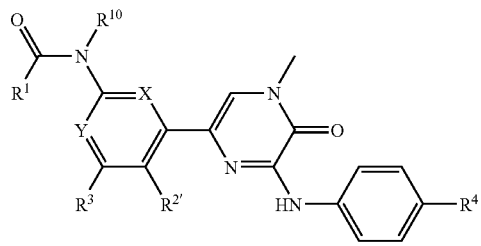

In certain embodiments, Z is N.

In certain embodiments, the compounds of the present invention are of Formula VII wherein $R^1$, $R^2$, $R^{2'}$, $R^3$, $R^{3'}$, $R^4$, $R^{10}$, and Z are as defined in Formula I.

(Formula VII)

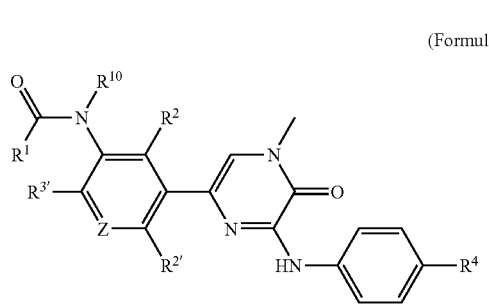

In certain embodiments, the compounds of the present invention are of Formula VIII wherein $R^1$, $R^2$, $R^{2'}$, $R^3$, $R^{3'}$, $R^4$, and $R^{10}$ are as defined in Formula I.

(Formula VIII)

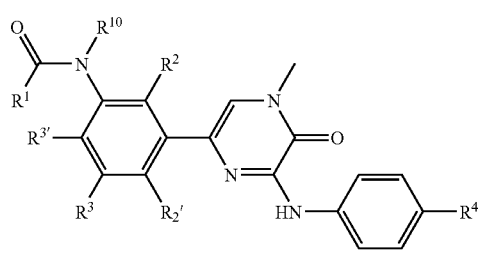

In certain embodiments, $R^{2'}$ is H.

In certain embodiments, $R^{2'}$ is F.

In certain embodiments, the compounds of the present invention are of Formula IX, wherein:

(Formula IX)

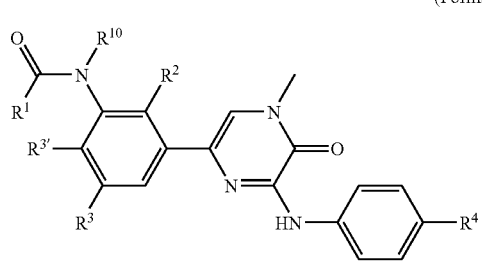

$R^1$ is chosen from:

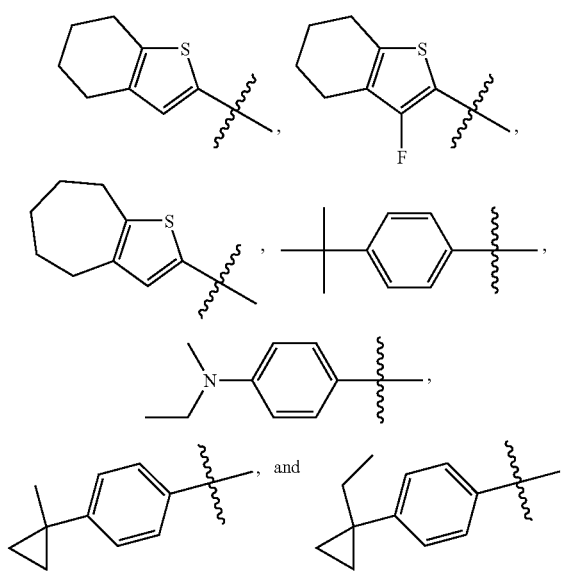

$R^2$ is chosen from H, $CH_3$, F, and Cl;
$R^3$ is chosen from H, $CH_3$, F, and Cl;
$R^{3'}$ is chosen from H, $CH_3$, F and Cl;
$R^4$ is

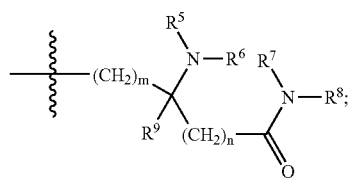

m is chosen from 0 and 1;
n is chosen from 0 and 1;
$R^5$ is chosen from H and $C_1$-$C_6$ alkyl;
$R^6$ is chosen from H and $C_1$-$C_6$ alkyl; or $R^5$ and $R^6$ are optionally taken together with the nitrogen atom to which they are attached to form a 6-membered cyclic ring having 0-1 additional N, S or O, wherein the optional additional ring nitrogen is optionally substituted with $C_1$-$C_3$ alkyl;
$R^7$ is chosen from H and $C_1$-$C_6$ alkyl wherein said alkyl is optionally substituted with one or more substituents chosen from OH and O($C_1$-$C_4$ alkyl); or $R^6$ and $R^7$ are optionally taken together with the —N($R^5$)C($R^9$)($CH_2$)$_n$C(=O) N($R^8$)— group through the respective nitrogen atoms to which they are directly attached to form a 6-membered cyclic ring;
$R^8$ is chosen from H and $C_1$-$C_6$ alkyl; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl;
$R^9$ is chosen from H and $CH_3$; and
$R^{10}$ is chosen from H and $C_1$-$C_3$ alkyl.

In certain embodiments, m is 0. In certain embodiments, n is 0.

In certain embodiments, $R^1$ is chosen from:

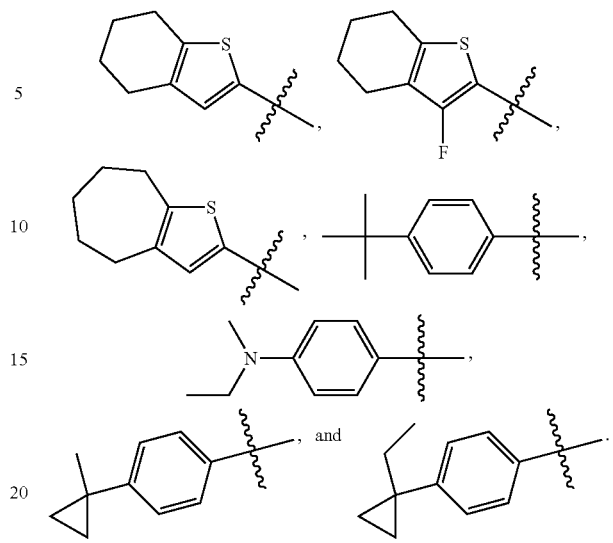

In certain embodiments, $R^1$ is chosen from:

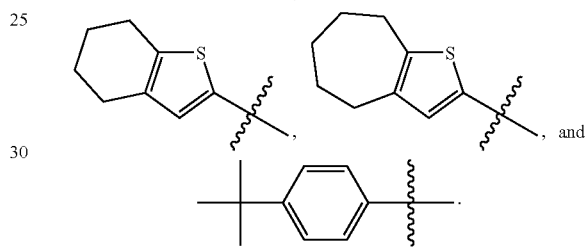

In certain embodiments, $R^2$ is chosen from $CH_3$, F, Cl, and H.

In certain embodiments, $R^2$ is chosen from $CH_3$, F, Cl and CN. In certain embodiments, $R^2$ is chosen from $CH_3$, F, and Cl. In certain embodiments, $R^2$ is $CH_3$.

In certain embodiments, $R^3$ is chosen from H, $CH_3$, F and Cl. In certain embodiments, $R^3$ is H. In certain embodiments, $R^3$ is chosen from F and Cl. In certain embodiments, $R^3$ is chosen from $CH_3$ and $OCH_3$.

In certain embodiments, $R^{3'}$ is chosen from H, $CH_3$, F and Cl. In certain embodiments, $R^{3'}$ is chosen from H, $CH_3$, F, Cl, and CN. In certain embodiments, $R^{3'}$ is H. In certain embodiments, $R^{3'}$ is chosen from $CH_3$ and F. In certain embodiments, $R^{3'}$ is chosen from Cl and CN.

In certain embodiments, $R^5$ is chosen from H and $C_1$-$C_3$ alkyl optionally substituted with OH. In certain embodiments, $R^5$ is chosen from H and $C_1$-$C_6$ alkyl. In certain embodiments, $R^5$ is chosen from H and $C_1$-$C_3$ alkyl. In certain embodiments, $R^5$ is chosen from H, methyl, ethyl and —($CH_2$)$_2$OH. In certain embodiments, $R^5$ is chosen from H, methyl, and ethyl.

In certain embodiments, $R^6$ is chosen from H and $C_1$-$C_3$ alkyl. In certain embodiments, $R^6$ is chosen from H, methyl, ethyl, n-propyl and i-propyl. In certain embodiments, $R^6$ is chosen from H, methyl and ethyl.

In certain embodiments, $R^5$ and $R^6$ are taken together with the nitrogen atom to which they are attached to form a 4- or 6-membered cyclic ring having 0-1 additional N, S or O, wherein the optional additional ring nitrogen is optionally substituted with $C_1$-$C_3$ alkyl. In certain embodiments, $R^5$ and $R^6$ are taken together with the nitrogen atom to which they are attached to form a 6-membered cyclic ring having 0-1 additional N, S or O, wherein the optional additional ring nitrogen is optionally substituted with $C_1$-$C_3$ alkyl. In certain embodiments, $R^5$ and $R^6$ are taken together with the nitrogen atom to which they are attached to form azetidinyl, N-methylpiperazinyl, N-ethylpiperazinyl or morpholinyl. In certain embodiments, $R^5$ and $R^6$ are taken together with the nitrogen atom to which they are attached to form N-methylpiperazinyl or N-ethylpiperazinyl.

In certain embodiments, $R^7$ is chosen from H, methyl, ethyl, —(CH$_2$)$_2$OH, and —(CH$_2$)$_2$OCH$_3$. In certain embodiments, $R^7$ is chosen from H, methyl, —(CH$_2$)$_2$OH, and —(CH$_2$)$_2$OCH$_3$. In certain embodiments, $R^6$ and $R^7$ are taken together with —N($R^5$)C($R^9$)(CH$_2$)$_n$C(=O)N($R^8$)— group through the respective nitrogen atoms to which they are directly attached to form a 6-membered cyclic ring (e.g.,

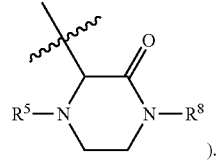
).

In certain embodiments, $R^8$ is chosen from H and $C_1$-$C_3$ alkyl. In certain embodiments, $R^8$ is chosen from H, methyl and ethyl. In certain embodiments, $R^7$ and $R^8$ are taken together with the nitrogen atom to which they are attached to form a 4- to 6-membered cyclic ring having 0-1 additional N, S or O, wherein the optional additional ring nitrogen is optionally substituted with $C_1$-$C_3$ alkyl. In certain embodiments, $R^7$ and $R^8$ are taken together with the nitrogen atom to which they are attached to form a 4- or 6-membered cyclic ring having 0-1 additional N or O, wherein the optional additional ring nitrogen is optionally substituted with methyl or ethyl and said cyclic ring is optionally substituted with OH. In certain embodiments, $R^7$ and $R^8$ are taken together with the nitrogen atom to which they are attached to form N-methylpiperazinyl, N-ethylpiperazinyl, morpholinyl, or azetidinyl optionally substituted with OH. In certain embodiments, $R^7$ and $R^8$ are taken together with the nitrogen atom to which they are attached to form morpholinyl or azetidinyl.

In certain embodiments, $R^9$ is H. In certain embodiments, $R^9$ is methyl.

In certain embodiments, $R^{10}$ is chosen from H and CH$_3$. In certain embodiments, $R^{10}$ is H. In certain embodiments, $R^{10}$ is —(CH$_2$)$_3$N(CH$_3$)$_2$. In certain embodiments, $R^{10}$ is OH.

In $R^5$—$R^8$ and $R^{10}$, where optionally substituted alkyl or a cyclic ring is substituted, in certain embodiments there are 1-3 substituents and these can replace any H atom. In $R^5$—$R^8$ and $R^{10}$, in certain embodiments cyclic rings are saturated.

In certain embodiments, $R^1$ contains a thiophene ring fused to a 5, 6, 7 or 8 membered ring as shown herein. In certain embodiments, $R^1$ contains a phenylene or benzo ring as shown herein. In certain embodiments, $R^5$, $R^6$, $R^7$ and/or $R^8$ form a cyclic ring and in certain embodiments, $R^5$, $R^6$, $R^7$ and/or $R^8$ are non-cyclic, as shown herein.

In certain embodiments, the compound of Formula I is chosen from

N-(3-(6-(4-(1,4-Dimethyl-3-oxopiperazin-2-yl)phenyl amino)-4-methyl-5-oxo-4,5-dihydropyrazin-2-yl)-2-fluorophenyl)-4,5,6,7-tetrahydrobenzo[b]thiophene-2-carboxamide;

N-(3-(6-(4-(1-(Ethyl(isopropyl)amino)-2-((2-methoxyethyl)(methyl)amino)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(1,2-Bis(4-ethylpiperazin-1-yl)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(1,2-Bis(4-ethyl piperazin-1-yl)-2-oxoethyl)phenylamino)-4-methyl-5-oxo-4,5-dihydropyrazin-2-yl)-2-methylphenyl)-5,6,7,8-tetrahydro-4H-cyclohepta[b]thiophene-2-carboxamide;

N-(3-(6-(4-(1-Ethyl-4-methyl-3-oxopiperazin-2-yl)phenylamino)-4-methyl-5-oxo-4,5-dihydropyrazin-2-yl)-2-methylphenyl)-4,5,6,7-tetra hydrobenzo[b]thiophene-2-carboxamide;

4-tert-Butyl-N-(3-(6-(4-(1-ethyl-4-methyl-3-oxopiperazin-2-yl)phenylamino)-4-methyl-5-oxo-4,5-dihydro pyrazin-2-yl)-2-methylphenyl)benzamide;

(S)—N-(3-(6-(4-(3-(Dimethyl amino)-2-(isopropyl(methyl)amino)-3-oxopropyl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(3-(Dimethylamino)-1-(isopropyl(methyl)amino)-3-oxopropyl)phenyl amino)-4-methyl-5-oxo-4,5-dihydropyrazin-2-yl)-2-methyl phenyl)-4,5,6,7-tetrahydro benzo[b]thiophene-2-carboxamide;

N-(3-(6-(4-(1-Amino-2-morpholino-2-oxoethyl)phenylamino)-4-methyl-5-oxo-4,5-dihydropyrazin-2-yl)-2-methylphenyl)-4-tert-butylbenzamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4,5,6,7-tetra hydrobenzo[b]thiophene-2-carboxamide;

4-tert-Butyl-N-(3-(6-(4-(1,4-dimethyl-3-oxopiperazin-2-yl) phenylamino)-4-methyl-5-oxo-4,5-dihydropyrazin-2-yl)-2-methylphenyl)benzamide;

N-(3-(6-(4-(2-Amino-1-(isopropyl(methyl)amino)-2-oxoethyl)phenylamino)-4-methyl-5-oxo-4,5-dihydro pyrazin-2-yl)-2-methylphenyl)-4,5,6,7-tetrahydrobenzo[b]thiophene-2-carboxamide;

N-(2-Methyl-3-(4-methyl-6-(4-(1-methyl-3-oxopiperazin-2-yl)phenylamino)-5-oxo-4,5-dihydropyrazin-2-yl)phenyl)-4,5,6,7-tetrahydrobenzo[b]thiophene-2-carboxamide;

N-(3-(6-(4-(2-(Dimethylamino)-1-(isopropyl(methyl)amino)-2-oxoethyl)phenyl amino)-4-methyl-5-oxo-4,5-dihydro pyrazin-2-yl)-2-methyphenyl)-4,5,6,7-tetrahydrobenzo[b]thiophene-2-carboxamide;

4-tert-Butyl-N-(3-(6-(4-(2-(dimethylamino)-1-(isopropyl (methyl)amino)-2-oxoethyl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenyl amino)-4-methyl-5-oxo-4,5-dihydropyrazin-2-yl)-2,5-difluorophenyl)-4,5,6,7-tetrahydrobenzo[b]thiophene-2-carboxamide;

(S)-4-tert-Butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide;

(R)-4-tert-Butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenylamino)-4-methyl-5-oxo-4,5-dihydro pyrazin-2-yl)-2-methylphenyl)-4-(ethyl(methyl)amino)benzamide;

(R)—N-(3-(6-(4-(2-(Dimethylamino)-1-(isopropyl(methyl)amino)-2-oxoethyl)phenyl amino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(1-ethylcyclopropyl)benzamide;

4-tert-Butyl-N-(3-(6-(4-(1-(4-ethylpiperazin-1-yl)-2-morpholino-2-oxoethyl)phenylamino)-4-methyl-5-oxo-4,5-dihydropyrazin-2-yl)-2-methylphenyl)benzamide;

N-(3-(6-(4-(1-(4-Ethylpiperazin-1-yl)-2-morpholino-2-oxoethyl)phenylamino)-4-methyl-5-oxo-4,5-dihydro pyrazin-2-yl)-2-methylphenyl)-4,5,6,7-tetrahydrobenzo[b]thiophene-2-carboxamide;

N-(3-(6-(4-(1-(4-ethylpiperazin-1-yl)-2-morpholino-2-oxoethyl)phenylamino)-4-methyl-5-oxo-4,5-dihydropyrazin-2-yl)-2-methyl phenyl)-5,6,7,8-tetrahydro-4H-cyclohepta[b]thiophene-2-carboxamide;

N-(3-(6-(4-(1,2-Bis(4-ethyl piperazin-1-yl)-2-oxoethyl)phenylamino)-4-methyl-5-oxo-4,5-dihydropyrazin-2-yl)-2-methylphenyl)-4-tert-butylbenzamide;

4-tert-Butyl-N-(3-(6-(4-(2-(dimethylamino)-1-(4-ethylpiperazin-1-yl)-2-oxoethyl)phenylamino)-4-methyl-5-oxo-4,5-dihydropyrazin-2-yl)-2-methylphenyl)benzamide;

N-(3-(6-(4-(2-(Dimethylamino)-1-(4-ethylpiperazin-1-yl)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(2-(Dimethylamino)-1-(4-ethylpiperazin-1-yl)-2-oxoethyl)phenylamino)-4-methyl-5-oxo-4,5-dihydro pyrazin-2-yl)-2-methylphenyl)-5,6,7,8-tetrahydro-4H-cyclohepta[b]thiophene-2-carboxamide;

4-tert-Butyl-N-(3-(6-(4-(1-(4-ethylpiperazin-1-yl)-2-((2-methoxyethyl)(methyl)amino)-2-oxoethyl)phenylamino)-4-methyl-5-oxo-4,5-dihydropyrazin-2-yl)-2-methylphenyl)benzamide;

N-(3-(6-(4-(1-(4-Ethylpiperazin-1-yl)-2-((2-methoxyethyl)(methyl)amino)-2-oxoethyl)phenylamino)-4-methyl-5-oxo-4,5-dihydropyrazin-2-yl)-2-methyl phenyl)-4,5,6,7-tetrahydrobenzo[b]thiophene-2-carboxamide;

N-(3-(6-(4-(1-(4-Ethylpiperazin-1-yl)-2-((2-methoxyethyl)(methyl)amino)-2-oxoethyl)phenylamino)-4-methyl-5-oxo-4,5-dihydro pyrazin-2-yl)-2-methylphenyl)-5,6,7,8-tetrahydro-4H-cyclohepta[b]thiophene-2-carboxamide;

N-(3-(6-(4-(1-Isopropyl-4-methyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(1,4-Dimethyl-3-oxopiperazin-2-yl)phenylamino)-4-methyl-5-oxo-4,5-dihydropyrazin-2-yl)-2-methylphenyl)-5,6,7,8-tetrahydro-4H-cyclohepta[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-5-fluoro-2-methylphenyl)-4,5,6,7-tetrahydrobenzo[b]thiophene-2-carboxamide;

N-(2-Chloro-3-(6-(4-(1,4-dimethyl-3-oxopiperazin-2-yl)phenylamino)-4-methyl-5-oxo-4,5-dihydropyrazin-2-yl)phenyl)-4,5,6,7-tetrahydrobenzo[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(ethyl(methyl)amino)benzamide;

N-(3-(6-(4-(1-(Ethyl(isopropyl)amino)-2-morpholino-2-oxoethyl)phenylamino)-4-methyl-5-oxo-4,5-dihydro pyrazin-2-yl)-2-methylphenyl)-4,5,6,7-tetrahydrobenzo[b]thiophene-2-carboxamide;

N-(3-(6-(4-(1-(Ethyl(isopropyl)amino)-2-(4-ethylpiperazin-1-yl)-2-oxoethyl)phenylamino)-4-methyl-5-oxo-4,5-dihydropyrazin-2-yl)-2-methyl phenyl)-4,5,6,7-tetrahydrobenzo[b]thiophene-2-carboxamide;

N-(3-(6-(4-(2-(Dimethylamino)-1-(ethyl(isopropyl)amino)-2-oxoethyl)phenyl mino)-4-methyl-5-oxo-4,5-dihydropyrazin-2-yl)-2-methylphenyl)-4,5,6,7-tetrahydrobenzo[b]thiophene-2-carboxamide;

N-{3-[6-({4-[2-(Azetidin-1-yl)-1-(morpholin-4-yl)-2-oxo ethyl]phenyl}amino)-4-methyl-5-oxo-4,5-dihydro pyrazin-2-yl]-2-methylphenyl}-4,5,6,7-tetrahydro-1-benzothiophene-2-carboxamide;

N-{2-Methyl-3-[4-methyl-6-({4-[(methylcarbamoyl)(morpholin-4-yl)methyl]phenyl}amino)-5-oxo-4,5-dihydropyrazin-2-yl]phenyl}-4,5,6,7-tetrahydro-1-benzothiophene-2-carboxamide;

N-{3-[6-({4-[2-(Azetidin-1-yl)-1-[ethyl(propan-2-yl)amino]-2-oxoethyl]phenyl}amino)-4-methyl-5-oxo-4,5-dihydro pyrazin-2-yl]-2-methylphenyl}-4,5,6,7-tetrahydro-1-benzothiophene-2-carboxamide;

N-{3-[6-({4-[(Dimethyl carbamoyl)[ethyl(propan-2-yl)amino]methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[1-(azetidin-1-yl)-2-(4-ethylpiperazin-1-yl)-2-oxoethyl]phenyl}amino)-4-methyl-5-oxo-4,5-dihydro pyrazin-2-yl]-2-methyl phenyl}-4H,5H,6H,7H,8H-cyclohepta[b]thiophene-2-carboxamide;

N-[3-(6-{[4-(1,4-Dimethyl-3-oxopiperazin-2-yl)phenyl]amino}-5-oxo-4,5-dihydro pyrazin-2-yl)-2-methylphenyl]-4,5,6,7-tetrahydro-1-benzothiophene-2-carboxamide;

N-{3-[6-({4-[Azetidin-1-yl(dimethylcarbamoyl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-[2-Methyl-3-(4-methyl-5-oxo-6-{[4-(1,2,4-trimethyl-3-oxopiperazin-2-yl)phenyl]amino}-4,5-dihydropyrazin-2-yl)phenyl]-4,5,6,7-tetrahydro-1-benzothiophene-2-carboxamide;

N-[5-Chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-{3-[6-({4-[Azetidin-1-yl(dimethylcarbamoyl)methyl]phenyl}amino)-4-methyl-5-oxo-4,5-dihydropyrazin-2-yl]-2-methylphenyl}-4-tert-butylbenzamide;

N-{3-[6-({4-[Azetidin-1-yl(dimethylcarbamoyl)methyl]phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{Azetidin-1-yl[(2-hydroxyethyl)(methyl)carbamoyl]methyl}phenyl)amino)-4-methyl-5-oxo-4,5-dihydropyrazin-2-yl]-2-methylphenyl)-4,5,6,7-tetrahydro-1-benzothiophene-2-carboxamide;

N-{2-Methyl-3-[4-methyl-6-({4-[4-methyl-3-oxo-1-(propan-2-yl)piperazin-2-yl]phenyl}amino)-5-oxo-4,5-dihydropyrazin-2-yl]phenyl}-4H,5H,6H,7H,8H-cyclohepta[b]thiophene-2-carboxamide;

N-{3-[6-({4-[(4-Ethyl piperazin-1-yl)][(2-hydroxy ethyl)(methyl)carbamoyl]methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[(Diethyl carbamoyl)(4-ethylpiperazin-1-yl)methyl]phenyl}amino)-4-methyl-5-oxo-4,5-dihydro pyrazin-2-yl]-2-methyl phenyl}-4H,5H,6H,7H,8H-cyclohepta[b]thiophene-2-carboxamide;

4-tert-Butyl-N-(3-{6-[(4-{[ethyl(methyl)carbamoyl](4-ethylpiperazin-1-yl)methyl}phenyl)amino]-4-methyl-5-oxo-4,5-dihydropyrazin-2-yl}-2-methylphenyl)benzamide;

4-tert-Butyl-N-{3-[6-({4-[(diethylcarbamoyl)(4-ethylpiperazin-1-yl)methyl]phenyl}amino)-4-methyl-5-oxo-4,5-dihydropyrazin-2-yl]-2-methylphenyl}benzamide;

N-[3-(6-{[4-(1,4-Dimethyl-3-oxopiperazin-2-yl)phenyl]amino}-5-oxo-4,5-dihydropyrazin-2-yl)-2-methylphenyl]-N-methyl-4,5,6,7-tetrahydro-1-benzothiophene-2-carboxamide;

4-tert-Butyl-N-(2-methyl-3-{4-methyl-6-[(4-{1-[methyl(propan-2-yl)amino]-2-(morpholin-4-yl)-2-oxoethyl}phenyl)amino]-5-oxo-4,5-dihydropyrazin-2-yl}phenyl)benzamide;

N-{3-[6-({4-[2-(Azetidin-1-yl)-1-[methyl(propan-2-yl)amino]-2-oxoethyl]phenyl}amino)-4-methyl-5-oxo-4,5-dihydropyrazin-2-yl]-2-methylphenyl}-4-tert-butylbenzamide;

N-{3-[6-({4-[1-(Azetidin-1-yl)-2-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{Azetidin-1-yl[(2-hydroxyethyl)(methyl)carbamoyl]methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

4-tert-Butyl-N-(2-methyl-3-{4-methyl-6-[(4-{1-[methyl(propan-2-yl)amino]-2-(4-methylpiperazin-1-yl)-2-oxoethyl}phenyl)amino]-5-oxo-4,5-dihydropyrazin-2-yl}phenyl)benzamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(1-methylcyclopropyl)benzamide;

N-(3-(6-(4-(1-Ethyl-4-methyl-3-oxopiperazin-2-yl)phenyl amino)-4-methyl-5-oxo-4,5-dihydropyrazin-2-yl)-2-methylphenyl)-5,6,7,8-tetrahydro-4H-cyclohepta[b]thiophene-2-carboxamide;

4-tert-Butyl-N-(3-(6-(4-(1-isopropyl-4-methyl-3-oxopiperazin-2-yl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide;

(S)—N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide;

(R)—N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide; and (S)-(+)-N-(3-(6-(4-(2-(Dimethylamino)-1-(isopropyl(methyl)amino)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-N-methyl-4,5,6,7-tetrahydro-1-benzothiophene-2-carboxamide;

N-(3-{6-[(4-{1-[ethyl(methyl)amino]-2-(4-ethylpiperazin-1-yl)-2-oxoethyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-6-[ethyl(methyl)amino]pyridine-3-carboxamide;

N-[3-(6-{[4-(1,4-dimethyl-3-oxopiperazin-2-yl)phenyl]amino}-4-methyl-5-oxo-4,5-dihydropyrazin-2-yl)-2-fluoro-5-methylphenyl]-4,5,6,7-tetrahydro-1-benzothiophene-2-carboxamide;

N-{3-[6-({4-[2-(azetidin-1-yl)-1-[methyl(propan-2-yl)amino]-2-oxoethyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4H,5H,6H,7H,8H-cyclohepta[b]thiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,5-dimethylphenyl]-4,5,6,7-tetrahydro-1-benzothiophene-2-carboxamide;

N-[5-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-{3-[6-({4-[(dimethylcarbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide;

N-{3-[6-({4-[(diethylcarbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{[ethyl(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide;

N-(3-{6-[(4-{[(2-hydroxyethyl)(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide;

N-{3-[6-({4-[2-(3-hydroxyazetidin-1-yl)-1-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide;

N-{3-[6-({4-[(dimethylcarbamoyl)(morpholin-4-yl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[(diethylcarbamoyl)(morpholin-4-yl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[2-(azetidin-1-yl)-1-(morpholin-4-yl)-2-oxoethyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{2-methyl-3-[4-methyl-6-({4-[(methylcarbamoyl)(morpholin-4-yl)methyl]phenyl}amino)-5-oxo-4,5-dihydropyrazin-2-yl]phenyl}-4H,5H,6H,7H,8H-cyclohepta[b]thiophene-2-carboxamide;

N-(3-{6-[(4-{[ethyl(methyl)carbamoyl](morpholin-4-yl)methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

N-(3-{6-[(4-{[(2-hydroxyethyl)(methyl)carbamoyl](morpholin-4-yl)methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

N-{3-[6-({4-[2-(3-hydroxyazetidin-1-yl)-1-(morpholin-4-yl)-2-oxoethyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methoxybenzamide;

N-[2-chloro-3-(6-{[4-(1,4-dimethyl-3-oxopiperazin-2-yl)phenyl]amino}-4-methyl-5-oxo-4,5-dihydropyrazin-2-yl)-5-methylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,6-dimethylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-5-methoxy-2-methylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[2,6-dichloro-3-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[6-chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[2-chloro-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[2-chloro-3-(6-{[4-(1,4-dimethyl-3-oxopiperazin-2-yl)phenyl]amino}-4-methyl-5-oxo-4,5-dihydropyrazin-2-yl)-6-fluorophenyl]-4,5,6,7-tetrahydro-1-benzothiophene-2-carboxamide;

N-[2-cyano-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[4-(6-{[4-(1,4-dimethyl-3-oxopiperazin-2-yl)phenyl]amino}-4-methyl-5-oxo-4,5-dihydropyrazin-2-yl)-6-fluoropyridin-2-yl]-4,5,6,7-tetrahydro-1-benzothiophene-2-carboxamide;

4-tert-butyl-N-{3-[6-({4-[(S)-(dimethylcarbamoyl)[methyl(propan-2-yl)amino]methyl]phenyl}amino)-4-methyl-5-oxo-4,5-dihydropyrazin-2-yl]-2-methylphenyl}benzamide;

4-tert-butyl-N-{3-[6-({4-[(R)-(dimethylcarbamoyl)[methyl(propan-2-yl)amino]methyl]phenyl}amino)-4-methyl-5-oxo-4,5-dihydropyrazin-2-yl]-2-methylphenyl}benzamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-N-[3-(dimethylamino)propyl]benzamide;

N-[6-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)pyridin-3-yl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)pyridin-2-yl]-4,5,6,7-tetrahydro-1-benzothiophene-2-carboxamide;

N-[2-chloro-3-(6-{[4-(1,4-dimethyl-3-oxopiperazin-2-yl)phenyl]amino}-4-methyl-5-oxo-4,5-dihydropyrazin-2-yl)-6-methylphenyl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)-5-fluoropyridin-2-yl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-oxo-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-hydroxy-4,5,6,7-tetrahydro-1-benzothiophene-2-carboxamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methylbenzamide;

N-[3-(6-{[4-(1-ethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[3-(6-{[4-(1-ethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[3-(6-{[4-(1-ethyl-4-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(4-ethyl-1-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

4-tert-butyl-N-[6-(6-{[4-(1,4-dimethyl-3-oxopiperazin-2-yl)phenyl]amino}-4-methyl-5-oxo-4,5-dihydropyrazin-2-yl)pyridin-2-yl]benzamide;

N-[5-(6-{[4-(1-ethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[5-(6-{[4-(1,4-diethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-7,7-difluoro-4,5,6,7-tetrahydro-1-benzothiophene-2-carboxamide;

N-[5-(6-{[4-(1-ethyl-4-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[6-(6-{[4-(1-ethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(4-ethyl-1-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1-ethyl-4-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1,4-diethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[3-(6-{[4-(1,4-diethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-{5-[6-({4-[(2R)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide;

N-[3-(6-{[4-(1,4-diethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-{5-[6-({4-[(2S)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide;

N-{6-[6-({4-[(2S)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide;

N-{6-[6-({4-[(2R)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide;

N-[2-fluoro-5-(4-methyl-6-{[4-(4-methyl-3-oxopiperazin-2-yl)phenyl]amino}-5-oxo-4,5-dihydropyrazin-2-yl)phenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-fluoro-6-methylphenyl]-4,5,6,7-tetrahydro-1-benzothiophene-2-carboxamide;

N-[3-(6-{[4-(1-ethyl-4-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[5-(6-{[4-(2,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-{5-[6-({4-[2-(azetidin-1-yl)-1-(dimethylamino)-2-oxoethyl]phenyl}amino)-4-methyl-5-oxo-4,5-dihydropyrazin-2-yl]-2-fluorophenyl}-4,5,6,7-tetrahydro-1-benzothiophene-2-carboxamide;

N-{2-fluoro-5-[6-({4-[1-(2-hydroxyethyl)-4-methyl-3-oxopiperazin-2-yl]phenyl}amino)-4-methyl-5-oxo-4,5-dihydropyrazin-2-yl]phenyl}-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,4-difluoro-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-4-hydroxy-4,5,6,7-tetrahydro-1-benzothiophene-2-carboxamide;

N-[3-(5-{[5-(1,4-dimethyl-3-oxopiperazin-2-yl)pyridin-2-yl]amino}-1-methyl-6-oxo-1,6-dihydropyridin-3-yl)-2-methylphenyl]-4,5,6,7-tetrahydro-1-benzothiophene-2-carboxamide; and pharmaceutically acceptable salts, solvates, and mixtures thereof.

The present compounds described herein are potent inhibitors of Btk. While not being bound by any theory, certain compounds have improved properties in the form of greater efficacy (as measured by, for example, the inhibition of Btk in whole blood and the inhibition of B-cell activation in mice).

Methods for obtaining the novel compounds described herein will be apparent to those of ordinary skill in the art, suitable procedures being described, for example, in the reaction schemes and examples below, and in the references cited herein. See, also, U.S. application Ser. No. 11/371,180 (US2006/0229337), filed Mar. 9, 2006, which is incorporated herein by reference in its entirety.

Reaction Scheme 1

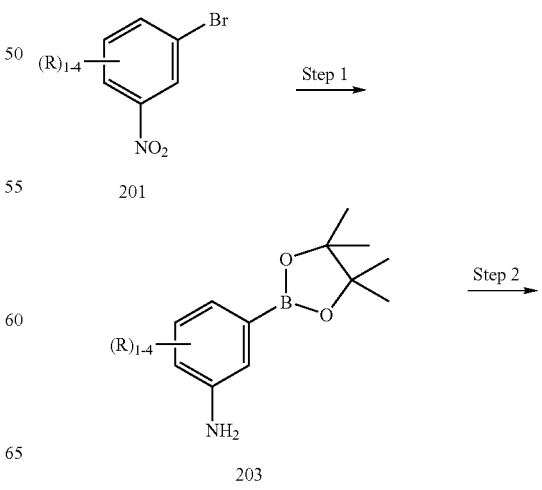

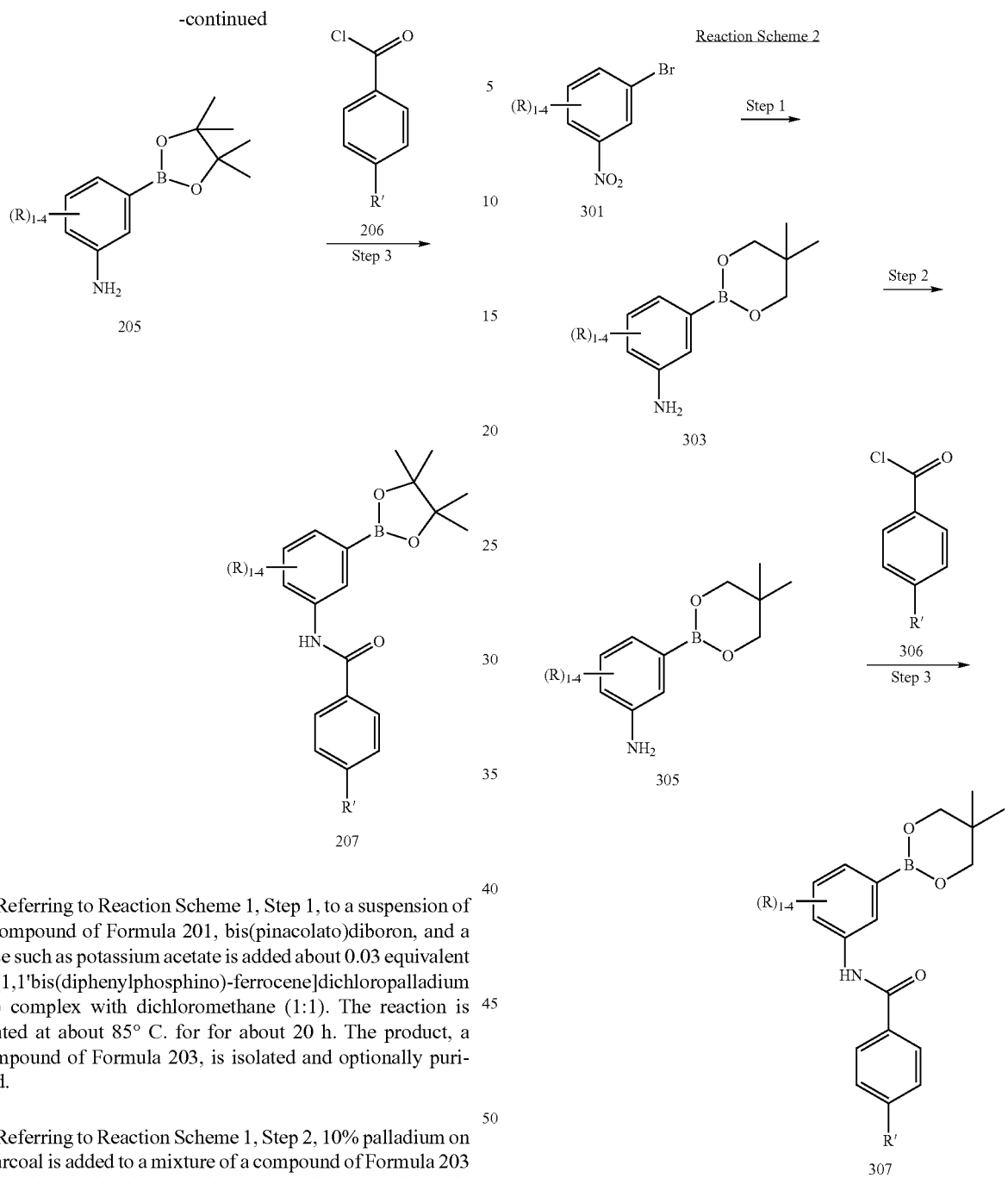

Referring to Reaction Scheme 1, Step 1, to a suspension of a compound of Formula 201, bis(pinacolato)diboron, and a base such as potassium acetate is added about 0.03 equivalent of [1,1'bis(diphenylphosphino)-ferrocene]dichloropalladium (II) complex with dichloromethane (1:1). The reaction is heated at about 85° C. for for about 20 h. The product, a compound of Formula 203, is isolated and optionally purified.

Referring to Reaction Scheme 1, Step 2, 10% palladium on charcoal is added to a mixture of a compound of Formula 203 in a polar, protic solvent such as methanol. To the mixture is added hydrogen gas. The reaction is stirred under balloon pressure of hydrogen at room temperature for about 13 h. The product, a compound of Formula 205, is isolated and optionally purified.

Referring to Reaction Scheme 1, Step 3, a solution of about an equivalent of a compound of formula 206 in an inert solvent such as dichloromethane is added portionwise to a solution of a compound of Formula 205 and a base such as triethylamine in an inert solvent such as dichloromethane. The mixture is stirred at room temperature for about 16 h. The product, a compound of Formula 207, is isolated and optionally purified.

Referring to Reaction Scheme 2, Step 1, a mixture of a compound of Formula 301; an excess (such as about 1.2 equivalents) of bis(neopentyl glycolato)diboron; and about 0.3 equivalent of [1,1'-bis(diphenylphosphino)-ferrocene] dichloropalladium, 1:1 complex with dichloromethane; and a base such as potassium acetate in an inert solvent such as dioxane is heated at reflux for about 3 h. The product, a compound of Formula 303, is isolated and optionally purified.

Referring to Reaction Scheme 2, Step 2, a mixture of a compound of Formula 303 and 10% palladium-on-carbon in an inert solvent such as ethyl acetate methanol is treated with 40 psi of hydrogen for about 2 h at room temperature. The product, a compound of Formula 305, is isolated and optionally purified.

Referring to Reaction Scheme 2, Step 3, a solution of a compound of Formula 305 and a base, such as triethylamine in an inert solvent such as THF is treated dropwise with about an equivalent of an acid chloride of the Formula 306 and the mixture is stirred at room temperature for about 15 min. The product, a compound of Formula 307, is isolated and optionally purified.

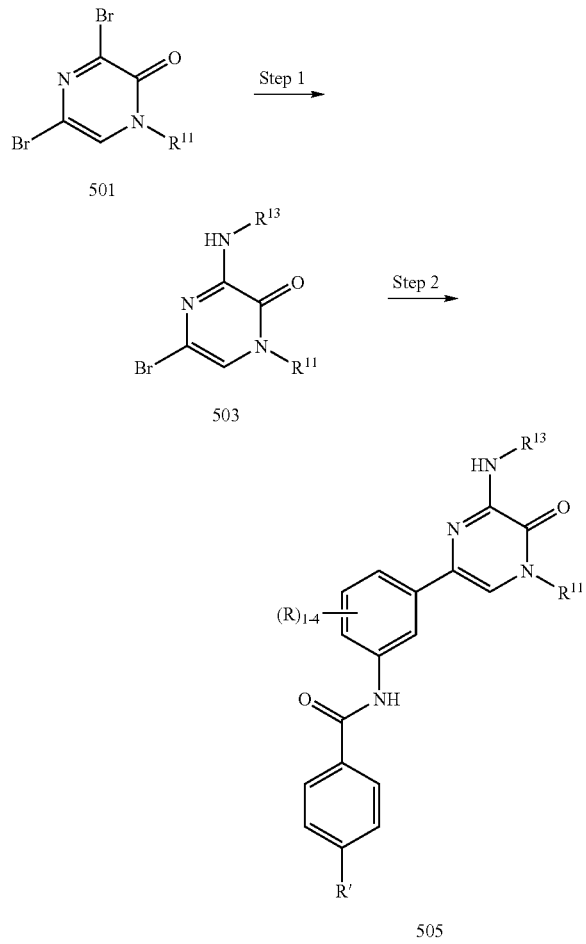

Referring to Reaction Scheme 3, Step 1, a mixture of a compound of Formula 501, about an equivalent of a compound of $NH_2$—$R^{13}$, and an inert base such as 1-methyl-2-pyrollidinone is heated at about 130° C. for about 1 hr. The product, a compound of Formula 503, is isolated and optionally purified, wherein $R^{13}$ is

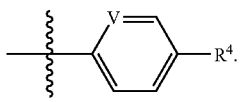

Referring to Reaction Scheme 3, Step 2, a mixture of a compound of Formula 503, an excess (such as about 1.2 equivalents) of a compound of Formula 107, about 0.05 equivalent of tetrakis(triphenylphosphine)palladium and a base such as 1N sodium carbonate in an inert solvent such as 1,2-dimethoxyethane is heated at about 100° C. in a sealed pressure vessel for about 16 hr. The product, a compound of Formula 505, is isolated and optionally purified.

In some embodiments, compounds of any one of Formulae I-IX are administered as a pharmaceutical composition or formulation. Accordingly, the invention provides pharmaceutical formulations comprising a compound of any one of Formulae I-IX and pharmaceutically acceptable salts, solvates, and mixtures thereof, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the compound is sufficient to provide a practical quantity of material for administration per unit dose of the compound.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such as sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the compound of the present invention.

Effective concentrations of a compound of any one of Formulae I-IX and pharmaceutically acceptable salts, solvates, and mixtures thereof, are mixed with a suitable pharmaceutical acceptable vehicle. In instances in which the compound exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the compound of any one of Formulae I-IX, the resulting mixture may be a solution, suspension, emulsion or the like. The form of the resulting mixture depends upon a number of factors, including the intended mode of administration and the solubility of the compound in the chosen vehicle. The effective concentration sufficient for ameliorating the symptoms of the disease treated may be empirically determined.

Compounds of any one of Formulae I-IX may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral formulations contain from 0.1 to 99% of a compound of any one of Formulae I-IX. In some embodiments, oral formulations contain at least 5% (weight %) of a compound of a Formula I. Some embodiments contain from 25% to 50% or from 5% to 75% of a compound of any one of Formulae I-IX.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol, or sucrose. Such formulations may also contain a demulcent.

Compounds of any one of Formulae I-IX can be incorporated into oral liquid preparations such as aqueous or oily suspensions, solutions, emulsions, syrups, or elixirs, for example. Moreover, formulations containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients include suspending agents, for example sodium carboxymethylcellulose, methylcellulose, hydropropylmethylcellulose, sodium alginate, polyvinylpyrrolidone, gum tragacanth and gum acacia; dispersing or wetting agents; naturally-occurring phosphatides, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n- propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Compounds of any one of Formulae I-IX may be administered parenterally in a sterile medium. Parenteral administration includes subcutaneous injections, intravenous, intramuscular, intrathecal injection or infusion techniques. Compounds of any one of Formulae I-IX, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Compounds of any one of Formulae I-IX may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Compounds of any one of Formulae I-IX may be formulated for local or topical application, such as for topical application to the skin and mucous membranes, such as in the eye, in the form of gels, creams, and lotions and for application to the eye. Topical compositions may be in any form including, for example, solutions, creams, ointments, gels, lotions, milks, cleansers, moisturizers, sprays, skin patches, and the like.

Such solutions may be formulated as 0.01% -10% isotonic solutions, pH 5-7, with appropriate salts. Compounds of any one of Formulae I-IX may also be formulated for transdermal administration as a transdermal patch.

Topical compositions comprising a compound of any one of Formulae I-IX can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, and ethylene glycol monostearate.

Compounds of any one of Formulae I-IX may also be topically administered in the form of liposome delivery systems, such as small unilamellar vesicles, large unilamellar vesicles, and multilamellar vesicles. Liposomes can be formed from a variety of phospholipids, such as cholesterol, stearylamine and phosphatidylcholines.

Other compositions useful for attaining systemic delivery of the compound include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance or be independent of therapeutic effects of the present compounds. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of a compound of any one of Formulae I-IX. These optional other active agents, when present, are typically employed in the compositions of the invention at a level ranging from 0.01% to 15%. Some embodiments contain from 0.1% to 10% by weight of the composition. Other embodiments contain from 0.5% to 5% by weight of the composition.

The invention includes packaged pharmaceutical formulations. Such packaged formulations include a pharmaceutical composition comprising a compound of any one of Formulae I-IX and pharmaceutically acceptable salts, solvates, and mixtures thereof, and instructions for using the composition to treat a mammal (typically a human patient). In some embodiments, the instructions are for using the pharmaceutical composition to treat a patient suffering from a disease responsive to inhibition of Btk activity and/or inhibition of B-cell and/or myeloid-cell activity. The invention can include providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the compounds of any one of Formulae I-IX can be administered alone, as mixtures, or in combination with other active agents.

Accordingly, the invention includes a method of treating a patient, for example, a mammal, such as a human, having a disease responsive to inhibition of Btk activity, comprising administrating to the patient having such a disease, an effective amount of a compound of any one of Formulae I-IX and pharmaceutically acceptable salts, solvates, and mixtures thereof.

To the extent that Btk is implicated in disease, alleviation of the disease, disease symptoms, preventative, and prophylactic treatment is within the scope of this invention. In some embodiments, compounds of any one of Formulae I-IX may also inhibit other kinases, such that alleviation of disease, disease symptoms, preventative, and prophylactic treatment of conditions associated with these kinases is also within the scope of this invention.

Methods of treatment also include inhibiting Btk activity and/or inhibiting B-cell and/or myeloid-cell activity, by inhibiting ATP binding or hydrolysis by Btk or by some other mechanism, in vivo, in a patient suffering from a disease responsive to inhibition of Btk activity, by administering an effective concentration of a compound of any one of Formulae I-IX and pharmaceutically acceptable salts, solvates, and mixtures thereof. An example of an effective concentration would be that concentration sufficient to inhibit Btk activity in vitro. An effective concentration may be ascertained experimentally, for example by assaying blood concentration of the compound, or theoretically, by calculating bioavailability.

In some embodiments, the condition responsive to inhibition of Btk activity and/or B-cell and/or myeloid-cell activity is cancer, a bone disorder, an allergic disorder and/or an autoimmune and/or inflammatory disease, and/or an acute inflammatory reaction.

The invention includes a method of treating a patient having cancer, a bone disorder, an allergic disorder and/or an autoimmune and/or inflammatory disease, and/or an acute inflammatory reaction, by administering an effective amount of a compound of any one of Formulae I-IX and pharmaceutically acceptable salts, solvates, and mixtures thereof.

In some embodiments, the conditions and diseases that can be affected using compounds of any one of Formulae I-IX, include, but are not limited to:

allergic disorders, including but not limited to eczema, allergic rhinitis or coryza, hay fever, bronchial asthma, urticaria (hives) and food allergies, and other atopic conditions;

autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, osteoarthritis, chronic Idiopathic thrombocytopenic purpura (ITP), Addison's disease, Parkinson's disease, Alzheimer's disease, Diabetes mellitus (type 1), septic shock, myasthenia gravis, Ulcerative Colitis, Aplastic anemia, Coeliac disease, Wegener's granulomatosis and other diseases in which the cells and antibodies arise from and are directed against the individual's own tissues;

acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis;

cancer, including but not limited to hematological malignancies, such as B-cell lymphoma, and acute lymphoblastic leukemia, acute myelogenous leukemia, chronic myelogenous leukemia, chronic and acute lymphocytic leukemia, hairy cell leukemia, Hodgkin's disease, Non-Hodgkin lymphoma, multiple myeloma, and other diseases that are characterized by cancer of the blood or lymphatic system; and bone disorders, including but not limited to osteoporosis.

Btk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Btk comprising contacting the cell with a compound of any one of Formulae I-IX, pharmaceutically acceptable salts, solvates, and mixtures thereof.

The invention provides methods of treatment in which a compound of any one of Formulae I-IX, and pharmaceutically acceptable salts, solvates, and mixtures thereof, or a composition (e.g., a pharmaceutical composition thereof), is the only active agent given to a patient and also includes methods of treatment in which a compound of any one of Formulae I-IX, and pharmaceutically acceptable salts, solvates, and mixtures thereof, or a composition (e.g., a pharmaceutical composition thereof), is given to a patient in combination with one or more additional active agents. The additional active agent(s) can be given to a patient sequentially or consecutively with a compound or composition of the present invention.

The invention provides methods of treatment of rheumatoid arthritis, systemic lupus erythematosus, multiple sclerosis and/or asthma in which a compound of any one of Formulae I-IX, and pharmaceutically acceptable salts, solvates, and mixtures thereof, is the only active agent given to a patient and also includes methods of treatment of rheumatoid arthritis, systemic lupus erythematosus, multiple sclerosis and/or asthma in which a compound of any one of Formulae I-IX, and pharmaceutically acceptable salts, solvates, and mixtures thereof, is given to a patient in combination with one or more additional active agents.

Thus in one embodiment the invention provides a method of treating cancer, a bone disorder, an allergic disorder and/or an autoimmune and/or inflammatory disease, and/or an acute inflammatory reaction, which comprises administering to a patient in need thereof an effective amount of a compound of any one of Formulae I-IX and pharmaceutically acceptable salts, solvates, and mixtures thereof, together with a second active agent, which can be useful for treating a cancer, a bone disorder, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with a compound of any one of Formulae I-IX and pharmaceutically acceptable salts, solvates, and mixtures thereof. In certain embodiments, a compound of any one of Formulae I-IX and pharmaceutically acceptable salts, solvates, and mixtures thereof, is combined with another active agent in a single dosage form. Suitable antitumor therapeutics that may be used in combination with a compound of any one of Formulae I-IX include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Compounds of any one of Formulae I-IX can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with a compound of any one of Formulae I-IX and pharmaceutically acceptable salts, solvates, and mixtures thereof, in an amount sufficient to increase the sensitivity of cancer cells to the chemotherapeutic agent is also provided herein.

Examples of other chemotherapeutic drugs that can be used in combination with the present compounds include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), biological agents (e.g. antibodies such as anti CD20 antibody, IDEC 8, immunotoxins, and cytokines), tyrosine kinase inhibitors (e.g., Gleevac) and the like. Such examples of other chemotherapeutic drugs that can be used in combination with the present compounds also include R-CHOP (cyclophosphamide (also called Cytoxan/Neosar), doxorubicin (or Adriamycin), vincristine (Oncovin) and prednisolone), ICE (ifosfamide, carboplatin, and etoposide), DHAP (dexamethasone, cisplatin, and cytarabine), ESHAP (etoposide, methylpredinsolone, cytarabine, and cisplatin), gemcitabine, Rituxan®, Treanda®, chlorambucil, fludarabine, alemtuzumab, and the like.

Included herein are methods of treatment, for example for treating autoimmune and/or inflammatory diseases, in which a compound of any one of Formulae I-IX and pharmaceutically acceptable salts, solvates, and mixtures thereof, is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In a further embodiment, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In additional embodiments the anti-inflammatory therapeutic agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide. The second anti-inflammatory agent that may be used in combination with any one or more compounds of the present invention includes biologics and oral agents for treating rheumatoid arthritis.

Other embodiments of the invention pertain to combinations in which at least one anti-inflammatory compound is an anti-C5 monoclonal antibody (such as eculizumab or pexelizumab), a TNF antagonist, such as entanercept, infliximab, and adalimumab (Humira®) which are anti-TNF alpha monoclonal antibodies.

Still other embodiments of the invention pertain to combinations in which at least one active agent is an immunosuppressant compound such as methotrexate, leflunomide, cyclosporine, tacrolimus, azathioprine, or mycophenolate mofetil.

Still other embodiments of the invention pertain to combinations with Rituxan® (Rituximab) or other agents that work by selectively depleting CD20+ B-cells.

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a compound of the invention can be used as a diagnostic for identifying and/or obtaining compounds that have the function of modulating an activity of a kinase as described herein. The compounds of the invention may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

The invention is further illustrated by the following non-limiting examples.

EXAMPLE 1

Scheme 1a

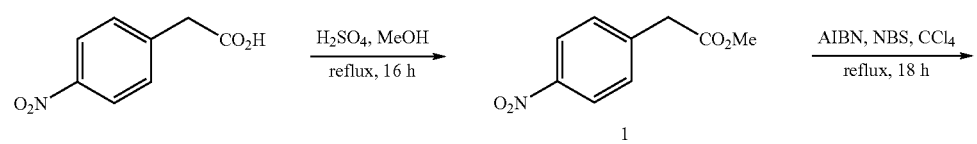

-continued
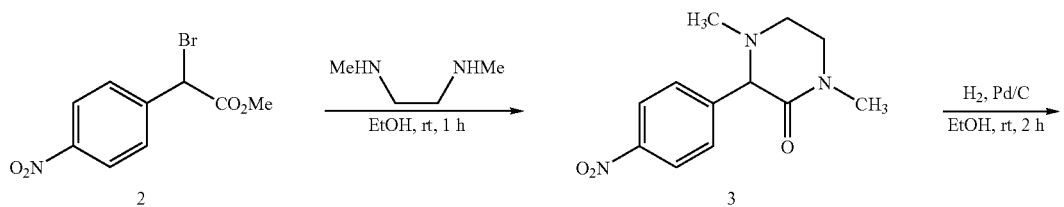
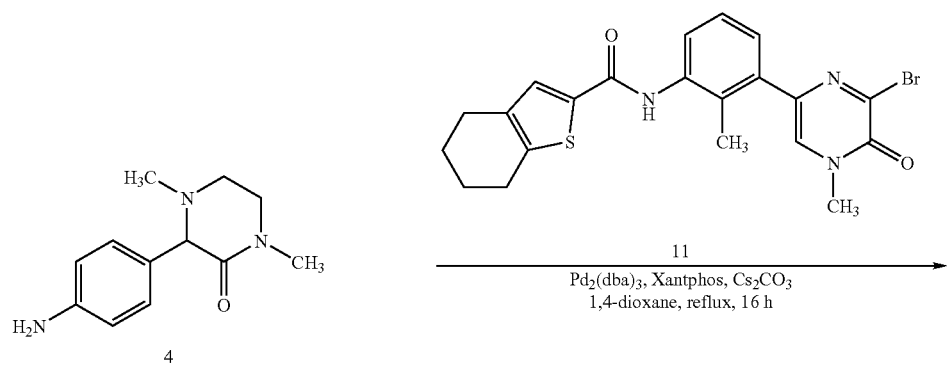
Scheme 1b
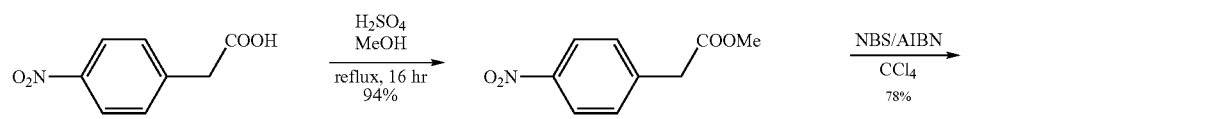
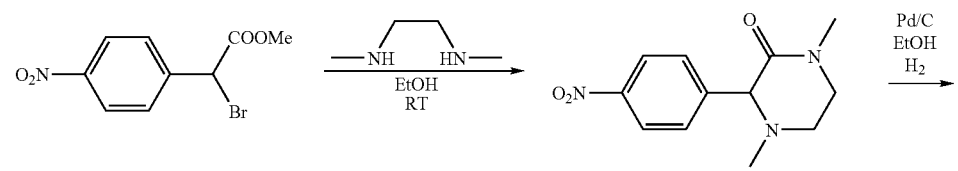
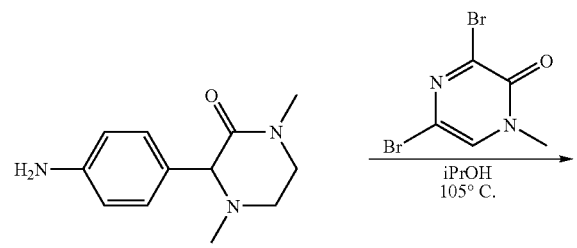

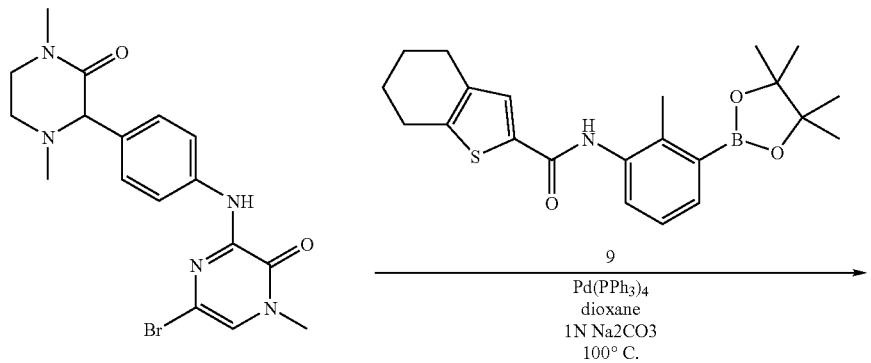

Methyl 2-(4-Nitrophenyl)acetate (1)

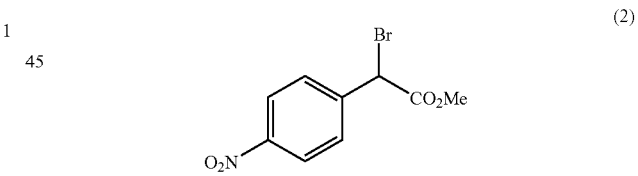

A 1-L single-neck round-bottomed flask equipped with a magnetic stirrer and reflux condenser was charged with 4-nitrophenylacetic acid (14.1 g, 77.5 mmol), anhydrous methanol (130 mL) and concentrated sulfuric acid (12.0 mL, 216 mmol), and the reaction mixture was heated at reflux for 16 h. After this time, the reaction was concentrated to dryness under reduced pressure. The resulting residue was partitioned between water (500 mL) and diethyl ether (200 mL) and the layers separated. The aqueous phase was extracted with diethyl ether (100 mL). The combined organic phases were washed with saturated aqueous sodium carbonate and dried over magnesium sulfate, and the drying agent was removed by filtration. The filtrate was concentrated under reduced pressure and dried to a constant weight under vacuum to afford a 96% yield of 1 (14.6 g) as a white solid: mp 45-46° C.; $^1$H NMR (500 MHz, CDCl$_3$) δ 8.19 (d, 2H, J=8.5 Hz), 7.46 (d, 2H, J=8.5 Hz), 3.75 (s, 2H), 3.73 (s, 3H). Reference: *Tetrahedron* 2002, 58, 10113.

Methyl 2-Bromo-2-(4-nitrophenyl)acetate (2)

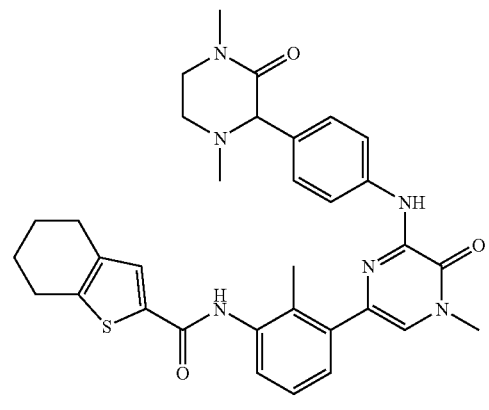

A 1-L single-neck round-bottomed flask equipped with a magnetic stirrer and reflux condenser was charged with 1 (10.6 g, 54.1 mmol), carbon tetrachloride (120 mL), N-bromosuccinimide (10.7 g, 59.9 mmol) and azobisisobutylonitrile (275 mg, 1.67 mmol), and the reaction mixture was heated at reflux for 18 h. After this time the reaction was cooled to room temperature and poured into heptane (120 mL). The resulting suspension was filtered and the filter cake washed with heptane (40 mL). The filtrate was concentrated under reduced pressure and the resulting residue was subjected to flash chromatography to afford 2 in 72% yield (10.7 g) as a clear oil: $^1$H NMR (500 MHz, CDCl$_3$) δ 8.23 (d, 2H, J=9 Hz), 7.74 (d, 2H, J=9.0 Hz), 5.40 (s, 1H), 3.82 (s, 3H); MS (ESI−) m/z 272 (M−H). Reference: *Tetrahedron* 2002, 58, 10113.

1,4-Dimethyl-3-(4-nitrophenyl)piperazin-2-one (3)

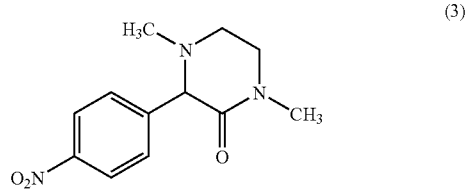

(3)

A 100-mL single-neck round-bottomed flask equipped with a magnetic stirrer was purged with nitrogen, charged with $N^1,N^2$-dimethylethane-1,2-diamine (1.61 g, 18.2 mmol), ethanol (5 mL) and 2 (500 mg, 1.82 mmol), and the reaction was stirred at room temperature for 1 h. After this time, the reaction mixture was evaporated under reduced pressure, and the resulting residue was purified by flash column chromatography to afford an 89% yield (404 mg) of 3 as a yellow oil: $^1$H NMR (500 MHz, DMSO-$d_6$) δ 8.18 (d, 2H, J=8.5 Hz), 7.60 (d, 2H, J=8.5 Hz), 3.87 (s, 1H), 3.61 (td, 1H, J=12.0, 4.0 Hz), 3.26 (ddd, 1H, J=12.0, 4.0, 2.5 Hz), 3.02 (ddd, 1H, J=12.0, 4.0, 2.5 Hz), 2.84 (s, 3H), 2.64 (td, 1H, J=12.0, 4.0 Hz), 2.06 (s, 3H).

3-(4-Aminophenyl)-1,4-dimethylpiperazin-2-one (4)

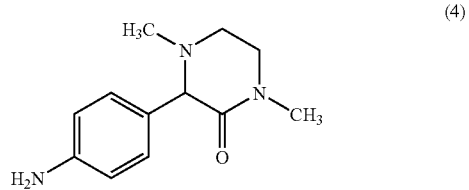

(4)

A 50-mL single-neck round-bottomed flask equipped with a magnetic stirrer was purged with nitrogen and charged with 3 (200 mg, 0.80 mmol), ethanol (5 mL) and 10% palladium on carbon (50% wet, 4 mg dry weight). The reaction flask was purged with hydrogen gas and the reaction mixture stirred under a balloon pressure of hydrogen for 2 h. After this time the flask was purged with nitrogen. The catalyst was removed by filtration through a pad of Celite 521 and the filter cake washed with ethanol (10 mL). The filtrate was concentrated under reduced pressure to afford a 94% yield of 4 (166 mg) as a colorless oil: $^1$H NMR (500 MHz, DMSO-$d_6$) δ 6.89 (d, 2H, J=8.5 Hz), 6.47 (d, 2H, J=8.5 Hz), 4.94 (s, 2H), 3.53 (td, 1H, J=12.0, 4.0 Hz), 3.44 (m, 1H), 3.21 (dt, 1H, J=12.0, 4.0 Hz), 2.92 (dt, 1H, J=12.0, 4.0 Hz), 2.82 (s, 3H), 2.02 (s, 3H); MS (ESI+) m/z 220 (M+H).

5-Bromo-3-hydroxy-1-methyl-1H-pyrazin-2-one hydrogen bromide salt (5)

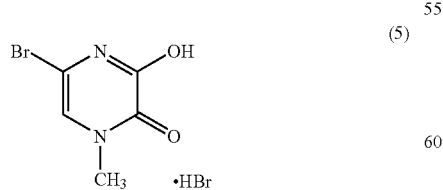

(5)

A 500-mL three-neck round bottomed flask equipped with a mechanical stirrer and reflux condenser was purged with nitrogen and charged with 2-(methylamino)acetonitrile (23.4 g, 220 mmol) and methylene chloride (200 mL). The suspension was treated with oxalyl bromide (50.0 g, 231 mmol) and the reaction heated to reflux. After 2.5 days the resulting mixture was cooled to 0° C. and filtered. The filter cake was washed with methylene chloride (2×30 mL) and dried to a constant weight under vacuum to afford a 79% yield of 5 (49.4 g) as an orange solid: mp 161-162° C. dec; $^1$H NMR (500 MHz, DMSO-$d_6$) δ 12.00 (s, 1H), 5.11 (s, 1H), 2.95 (s, 3H); MS (ESI+) m/z 205 (M−Br).

4,4,5,5-Tetramethyl-2-(2-methyl-3-nitro-phenyl)-[1,3,2]dioxaborolane (6)

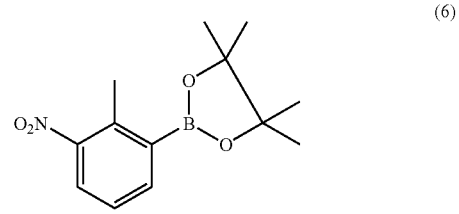

(6)

A 1-L three-neck round-bottomed flask equipped with a mechanical stirrer and thermoregulator was purged with nitrogen and charged with 2-bromo-6-nitrotoluene (60.2 g; 278 mmol), bis(pinacolato)diboron (85.2 g; 336 mmol), potassium acetate (82.4 g; 840 mmol) and DMSO (320 mL). A stream of nitrogen was passed through the resulting suspension for 30 min, [1,1'bis(diphenylphosphino)-ferrocene] dichloropalladium (II), complex with dichloromethane (1:1) (7.60 g; 9.30 mmol) was then added and the reaction heated at 85° C. for 20 h. After this time the mixture was cooled to ambient temperature, poured into a mixture of water (1300 mL) and MtBE (500 mL) and treated with Cellpure P65 (150 cc). The resulting suspension was filtered through a pad of Cellpure P65 (200 cc) packed onto a fritted funnel (ID 185 mm). The filter cake was washed with MtBE (3×180 mL) and the organic layer of the filtrate separated, washed with water (3×1 L) and dried over sodium sulfate. After filtering off sodium sulfate, the filtrate was concentrated and purified by flash chromatography to afford 4,4,5,5-tetramethyl-2-(2-methyl-3-nitro-phenyl)-[1,3,2]dioxaborolane (6) as a light yellow solid: mp 52-53° C.; MS (APCI+) m/z 264 (M+H).

2-Methyl-3-(4,4,5,5-tetramethyl-[1,3,2]dioxaborolan-2-yl)-phenylamine (7)

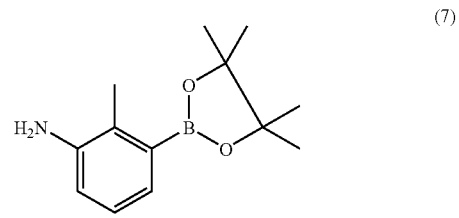

(7)

A 500-mL round-bottomed flask equipped with a magnetic stirrer was charged with 4,4,5,5-Tetramethyl-2-(2-methyl-3-nitro-phenyl)-[1,3,2]dioxaborolane (6) (8.44 g; 32.1 mmol) and methanol (150 mL). The reaction flask was twice evacuated and back-filled with argon. 10% Palladium on charcoal (50% wet, 425 mg dry weight) was then added to the solution, and the reaction flask evacuated and back-filled with hydrogen three times. The reaction was then stirred under balloon pressure of hydrogen at room temperature for 13 h. After this time, the flask was twice evacuated and back-filled with argon, then filtered through a pad of Celite 521 and the filtrate concentrated in vacuo. The resulting residue was dried under high vacuum for 1 d to afford a quantitative yield (8.16 g) of 2-methyl-3-(4,4,5,5-tetramethyl-[1,3,2]dioxaborolan-2-yl)-phenylamine (7) as a white solid: mp 110-112° C.; MS (ESI+) m/z 234 (M+H).

4,5,6,7-Tetrahydro-benzo[b]thiophene-2-carbonyl Chloride (8)

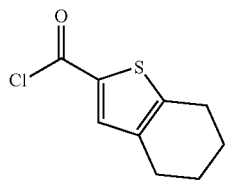

8

4,5,6,7-Tetrahydro-benzo[b]thiophene-2-carboxylic acid (1.0 g, 5.50 mmol) is dissolved in dichloromethane [DCM] (25 mL) that contains 5 drops of N,N-dimethylformamide [DMF] under nitrogen and cooled to 0° C. Oxalyl chloride (13.7 mL of a 2.0M solution in DCM) is added via syringe and allowed to warm to RT over 1 hour. All solvent is then removed under reduced pressure, and the resultant oil is reduced from toluene (3×20 mL) to remove residual oxalyl chloride. The residue is then dissolved in ethyl acetate and washed with saturated sodium bicarbonate (1×100 mL), then washed with saturated sodium chloride (1×100 mL) and dried over sodium sulfate. The solution is then filtered and concentrated under reduced pressure to give 4,5,6,7-tetrahydro-benzo[b]thiophene-2-carbonyl chloride (8) as an off-white solid (1.03 g).

4,5,6,7-Tetrahydro-benzo[b]thiophene-2-carboxylic acid [2-methyl-3-(4,4,5,5-tetramethyl-[1,3,2]diox-aborolan-2-yl)-phenyl]-amide (9)

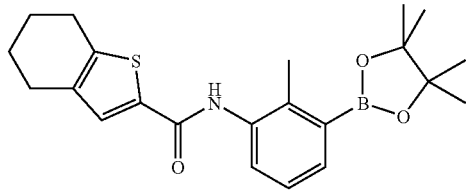

9

2-Methyl-3-(4,4,5,5-tetramethyl-[1,3,2]dioxaborolan-2-yl)-phenylamine (7) (1.20 g, 5.16 mmol, 1.0 equiv) and pyridine (0.42 mL, 25.8 mmol) are dissolved in DCM (40 mL) at 0° C. under a nitrogen atmosphere. 4,5,6,7-Tetrahydro-benzo[b]thiophene-2-carbonyl chloride (8) (1.03 g, 5.16 mmol) is then added in portions over 5 min and allowed to react warming to RT over 60 min. All solvent is then removed under reduced pressure, and the resultant oil is reduced from toluene (3×20 mL) to remove residual pyridine. The residue is then dissolved in ethyl acetate and washed with sodium hydroxide (1N, 1×100 mL), then washed with saturated sodium chloride (1×100 mL) and dried over sodium sulfate. The solution is then filtered and concentrated under reduced pressure to give 4,5,6,7-tetrahydro-benzo[b]thiophene-2-carboxylic acid [2-methyl-3-(4,4,5,5-tetramethyl-[1,3,2]dioxaborolan-2-yl)-phenyl]-amide (9) as an off-white solid (1.87 g).

Sodium 4-methyl-6-(2-methyl-3-(4,5,6,7-tetrahydrobenzo[b]thiophene-2-carboxamido)phenyl)-3-oxo-3,4-dihydropyrazin-2-olate (10)

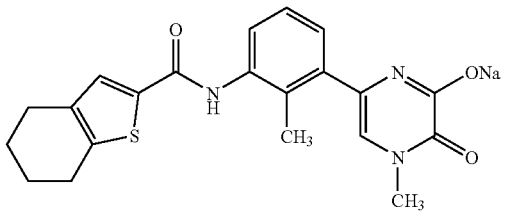

(10)

A 250-mL three-neck round-bottomed flask equipped with a mechanical stirrer, reflux condenser and nitrogen inlet was charged with 1,4-dioxane (100 mL) and aqueous 2.0 M sodium carbonate (15 mL, 29.5 mmol). After bubbling nitrogen through the resulting solution for 15 minutes, 5 (8.44 g, 29.5 mmol), 9 (12.9 g, 32.5 mmol) and tetrakis(triphenylphosphine)palladium (2.38 g, 2.06 mmol) were added and the reaction mixture then heated at reflux for 20 h. After this time the reaction was cooled to room temperature and filtered through a pad of Celite 521. The filter cake was washed with a 1:1 solution of methanol/methylene chloride (350 mL) and the filter cake discarded. On standing a precipitate formed in the filtrate and this solid was filtered. The filter cake was triturated with ethyl acetate (50 mL), filtered and dried under vacuum. The resulting solid was suspended in water (75 mL), filtered and the filter cake washed with water (25 mL). The filter cake was dried to a constant weight to give a 53% yield (6.57 g) of 10 as a light yellow solid: mp 225-230° C. dec, $^1$H NMR (500 MHz, DMSO-$d_6$) δ 9.73 (s, 1H), 7.66 (s, 1H), 7.21 (m, 1H), 7.16 (m, 2H), 6.37 (s, 1H), 2.75 (m, 2H), 2.61 (m, 2H), 2.20 (s, 3H), 1.77 (m, 4H); MS (ESI+) m/z 418(M+H).

N-(3-(6-Bromo-4-methyl-5-oxo-4,5-dihydropyrazin-2-yl)-2-methylphenyl)-4,5,6,7-tetrahydrobenzo[b]thiophene-2-carboxamide (11)

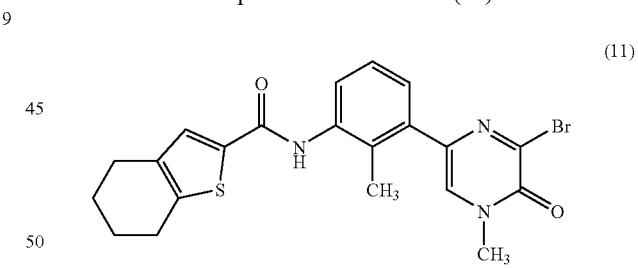

(11)

A 250-mL single-neck round-bottomed flask equipped with a magnetic stirrer and reflux condenser was purged with nitrogen and charged with 10 (6.55 g, 15.7 mmol) and anhydrous methylene chloride (60 mL). To the resulting suspension phosphorous oxybromide (9.95 g, 34.3 mmol) and N,N-dimethylformamide (190 mg, 2.60 mmol) were added and the reaction was then heated at reflux for 4 h. After this time the reaction mixture was poured into a 10% aqueous potassium carbonate solution (100 mL) and methylene chloride (75 mL) was added. The resulting suspension was filtered through Celite 521 and the layers separated. The aqueous layer was extracted with methylene chloride (2×100 mL) and the combined organic layers were dried over sodium sulfate, filtered and concentrated under reduced pressure. The resulting residue was triturated with a 2:1 solution of ethyl acetate/hexanes (10 mL) and filtered. The filter cake was washed with the 2:1 ethyl acetate/hexanes solution (20 mL) and dried to a constant weight under vacuum to afford a 50% yield (3.59 g) of 11 as a light yellow solid: mp 240-241° C., $^1$H NMR (500 MHz, DMSO-$d_6$) δ 9.86 (s, 1H), 7.98 (s, 1H), 7.67 (s, 1H), 7.28 (m, 3H), 3.57 (s, 3H), 2.76 (t, 2H, J=5.5 Hz), 2.61 (t, 2H, J=5.5 Hz), 2.18 (s, 3H), 1.76 (m, 4H); MS (ESI+) m/z 458(M+H).

N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (12)

(12)

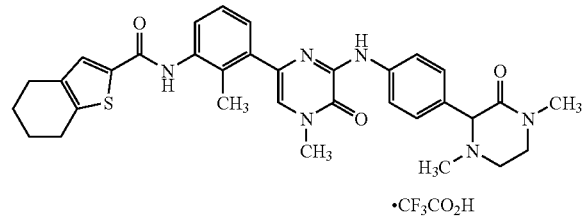

·CF$_3$CO$_2$H

A 25-mL single-neck round-bottomed flask equipped with a magnetic stirrer and reflux condenser was charged with 4 (160 mg, 0.73 mmol), 11 (304 mg, 0.66 mmol), cesium carbonate (475 mg, 1.46 mmol) and 1,4-dioxane (10 mL). After bubbling nitrogen through the resulting solution for 30 minutes, Xantphos (32 mg, 0.056 mmol) and tris(dibenzylideneacetone)dipalladium(0) (30 mg, 0.033 mmol) were added and the reaction mixture was heated at reflux for 16 h. After this time the reaction was cooled to room temperature and concentrated under reduced pressure. The resulting residue was absorbed onto silica gel and purified by flash chromatography to give a residue, which was further purified by preparative reverse phase HPLC to afford a 30% yield (143 mg) of 12 as a yellow solid: mp 155-156° C.; $^1$H NMR (500 MHz, DMSO-$d_6$) δ 9.82 (s, 1H), 9.43 (s, 1H), 8.08 (d, 2H, J=7.5 Hz), 7.68 (s, 1H), 7.32 (d, 2H, J=7.5 Hz), 7.27-7.32 (m, 3H), 7.24 (s, 1H), 4.88 (bs, 1H), 3.42-3.75 (m, 4H), 3.59 (s, 3H), 2.95 (s, 3H), 2.76 (m, 2H), 2.61 (m, 5H), 2.28 (s, 3H), 1.78 (m, 4H); MS (ESI+) m/z 597 (M+H).

EXAMPLE 2

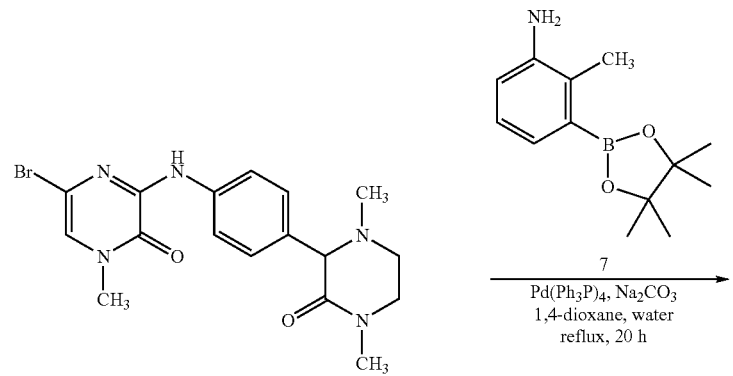

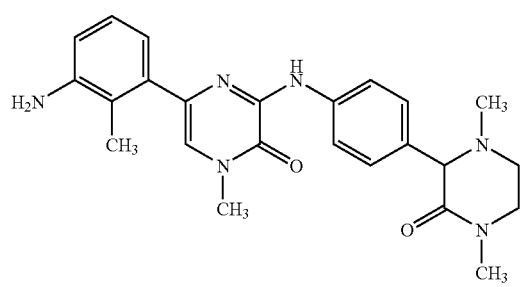

-continued
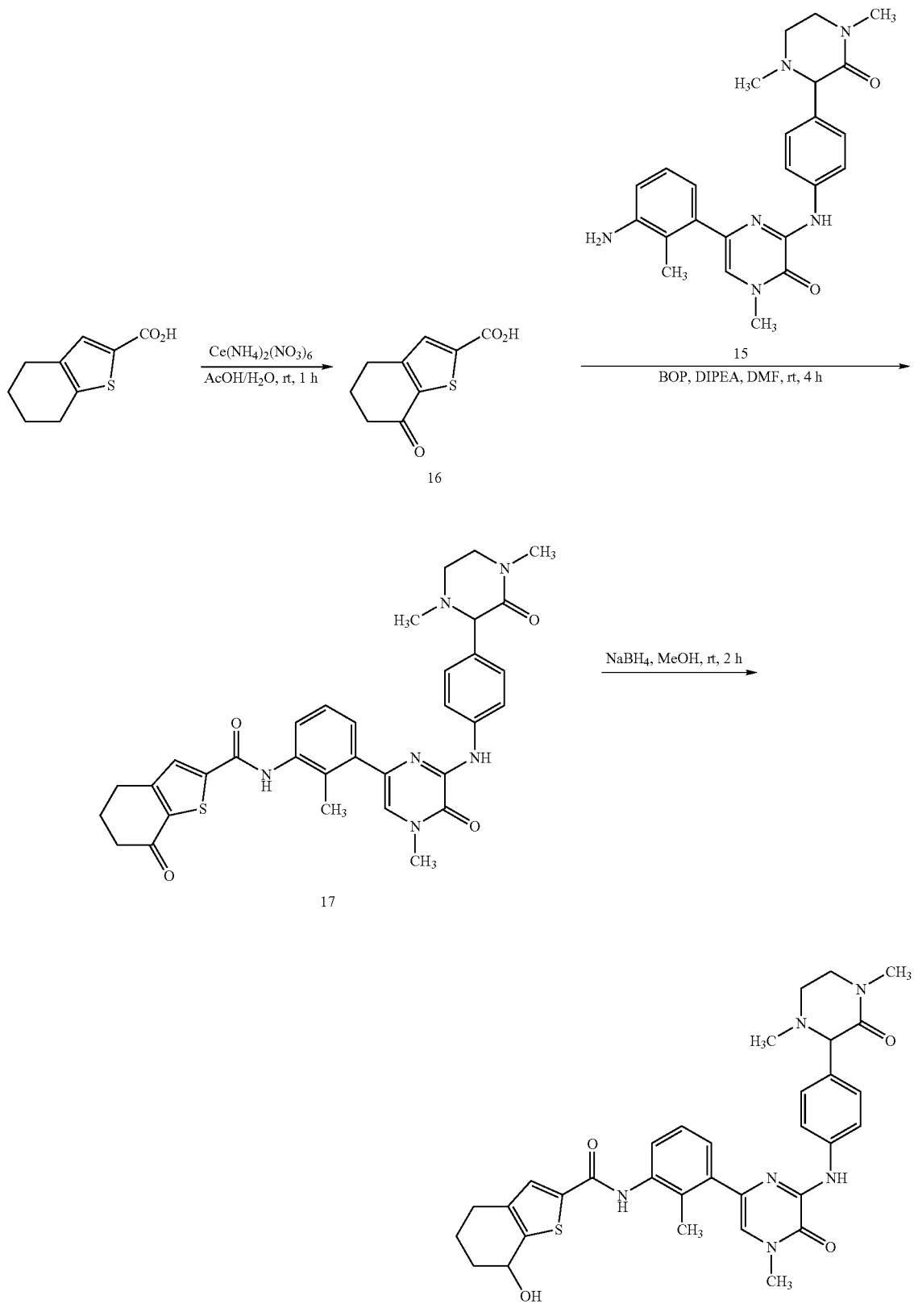

3,5-dibromo-1-methyl-2(1H)pyrazinone (13)

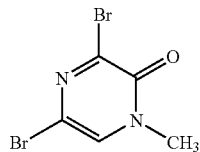

(*J. Heterocycl. Chem.* 1983, 20, 919)

A 250-mL three-neck round-bottomed flask equipped with a magnetic stirrer and reflux condenser was charged with 1,2-dichlorobenzene (100 mL) and oxalyl bromide (60.6 g; 281 mmol). To the solution was added methylamino-acetonitrile (7.01 g; 65.8 mmol) and the reaction heated under nitrogen to 80° C. After 18 h the resulting mixture was cooled to room temperature, evaporated under reduced pressure and the resulting residue purified by flash chromatography to afford 3,5-dibromo-1-methyl-2(1H)pyrazinone (13) (2.87 g, 16%) as an off-white solid: mp 94-95° C.; MS (ESI+) m/z 267 (M+H).

5-Bromo-3-(4-(1,4-dimethyl-3-oxopiperazin-2-yl)phenylamino)-1-methylpyrazin-2(1H)-one (14)

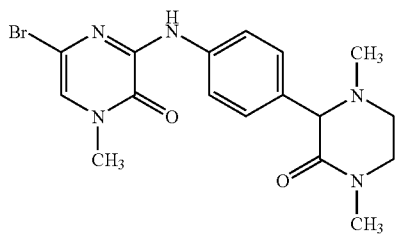

A 100-mL three-neck round-bottomed flask equipped with a mechanical stirrer and reflux condenser was charged with (4) (780 mg, 3.56 mmol), 13 (998 mg, 3.73 mmol), cesium carbonate (2.36 g, 7.26 mmol) and 1,4-dioxane (40 mL). After bubbling nitrogen through the resulting solution for 30 minutes, Xantphos (0.162 g, 0.281 mmol) and tris(dibenzylideneacetone)dipalladium(0) (0.15 g, 0.165 mmol) were added, and the reaction mixture was heated at reflux for 16 h. After this time the reaction was cooled to room temperature and concentrated under reduced pressure. The resulting residue was absorbed onto silica gel and purified by flash chromatography to afford a 57% yield (818 mg) of 14 as an orange solid: mp 206-207° C.; $^1$H NMR (500 MHz, CDCl$_3$) δ 8.27 (bs, 1H), 7.72 (dd, 1H, J=2.0, 8.5 Hz), 7.36 (dd, 2H, J=2.0, 8.5 Hz), 6.73 (s, 1H), 3.71 (m, 1H), 3.69 (s, 1H), 3.52 (s, 3H), 3.21 (m, 1H), 3.01 (m, 1H), 2.97 (s, 3H), 2.67 (m, 1H), 2.19 (s, 3H); MS (ESI+) m/z 406 (M+H).

5-(3-Amino-2-methylphenyl)-3-(4-(1,4-dimethyl-3-oxopiperazin-2-yl)phenylamino)-1-methylpyrazin-2(1H)-one (15)

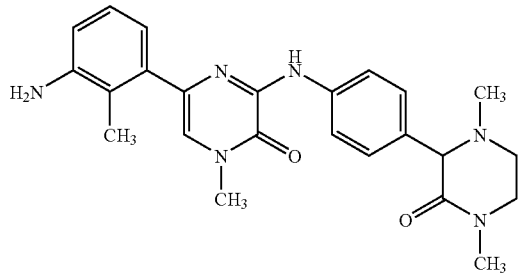

A 250-mL three-neck round-bottomed flask equipped with a magnetic stirrer, reflux condenser and nitrogen inlet was charged with 14 (2.50 g, 6.16 mmol), 7 (1.79 g, 7.70 mmol), 1,4-dioxane (70 mL) and a solution of sodium carbonate (1.96 g, 18.5 mmol) in water (14 mL). After bubbling nitrogen through the resulting mixture for 30 min, tetrakis(triphenylphosphine)palladium (711 mg, 0.62 mmol) was added and the reaction mixture then heated at reflux for 11 h. After this time the reaction was cooled to room temperature and 2N hydrochloric acid (70 mL) followed by ethyl acetate (70 mL) was added. The mixture was stirred for 0.5 h and then filtered through a pad of Celite 521. The organic layer of the filtrate was separated and extracted with 2N hydrochloric acid (2×30 mL). The acidic extracts were combined and washed with ethyl acetate (4×50 mL). The aqueous solution was then stirred vigorously with ethyl acetate (100 mL) while solid potassium carbonate was added portionwise until a pH of 12 was reached. The aqueous layer was separated and extracted with ethyl acetate (2×100 mL). The combined organic layers were washed with brine (70 mL) and dried over magnesium sulfate. The drying agent was removed by filtration, and the filtrate was concentrated under reduced pressure and dried in a 49° C. vacuum oven for 24 h to afford 15 in 86% yield (2.32 g) as an amber foam: mp 133-134° C.; $^1$H NMR (500 MHz, CDCl$_3$) δ 8.29 (s, 1H), 7.80 (d, 1H, J=8.5 Hz), 7.29 (d, 2H, J=8.5 Hz), 7.05 (t, 1H, J=8.0 Hz), 6.79 (d, 1H, J=7.5 Hz), 6.73 (d, 1H, J=7.5 Hz), 6.68 (s, 1H), 3.72 (s, 3H), 3.64 (m, 1H), 3.20 (m, 1H), 3.01 (m, 1H), 2.99 (s, 3H), 2.66 (m, 1H), 2.24 (s, 3H), 2.17 (s, 3H); MS (ESI+) m/z 433.3 (M+H).

7-Oxo-4,5,6,7-tetrahydrobenzo[b]thiophene-2-carboxylic Acid (16)

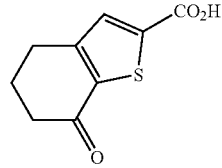

A 25-mL single-neck round-bottomed flask equipped with a magnetic stirrer was purged with nitrogen and charged with 4,5,6,7-tetrahydrobenzo[b]thiophene-2-carboxylic acid (3.00 g, 16.5 mmol), acetic acid (40 mL) and water (40 mL). A solution of ammonium cerium(IV) nitrate (36.1 g, 65.9 mmol) in acetic acid (40 mL) was added dropwise, and the reaction was stirred at room temperature for 1 h. After this time, the reaction mixture was poured into water (200 mL) and extracted with methylene chloride (3×200 mL). The organic extracts were combined, dried over sodium sulfate, filtered and the solvent removed under reduced pressure to afford 16 in 72% yield (2.35 g) as a yellow solid: mp 174-175° C.; $^1$H NMR (500 MHz, DMSO-d$_6$) δ 13.60 (bs, 1H), 7.68 (s, 1H), 2.86 (t, 2H, J=6.0 Hz), 2.59 (t, 2H, J=6.0 Hz), 2.08 (quintet, 2H, J=6.0 Hz).

N-(3-(6-(4-(1,4-Dimethyl-3-oxopiperazin-2-yl)phenylamino)-4-methyl-5-oxo-4,5-dihydropyrazin-2-yl)-2-methylphenyl)-7-oxo-4,5,6,7-tetrahydrobenzo[b]thiophene-2-carboxamide (17)

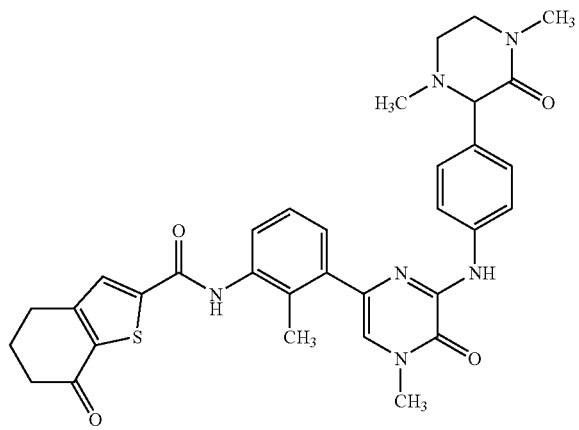

A 50-mL single-neck round-bottomed flask equipped with a magnetic stirrer was purged with nitrogen and charged with 15 (249 mg, 1.27 mmol), 16 (500 mg, 1.16 mmol), N,N-diisopropylethylamine (600 mg, 4.64 mmol) and anhydrous DMF (5 mL). Benzotriazol-1-yl-oxy-tris(dimethylamino)phosphonium hexafluorophosphate (BOP, 616 mg, 1.39 mmol) was added, and the reaction was stirred for 4 h. After this time, the reaction was diluted with water (10 mL), and the resulting suspension was filtered. The filter cake was dissolved in methylene chloride (20 mL), and the solution was washed with 10% aqueous citric acid (10 mL), saturated aqueous sodium bicarbonate (10 mL), and water (10 mL), and dried over sodium sulfate. The drying agent was removed by filtration, and the solvent was evaporated under reduced pressure. The resulting residue was purified by flash chromatography to afford a 52% yield of 17 (370 mg) as a white solid: mp 154-155° C.; $^1$H NMR (500 MHz, CD$_2$Cl$_2$) δ 8.31 (s, 1H), 7.81 (dd, 1H, J=7.5, 1.5 Hz), 7.76-7.72 (m, 3H), 7.50 (s, 1H), 7.28-7.23 (m, 4H), 6.73 (s, 1H), 3.64 (td, 1H, J=11.5, 4.5 Hz), 3.57 (s, 1H), 3.55 (s, 3H), 3.14 (dt, 1H, J=11.5, 3.5 Hz), 2.93 (m, 1H), 2.88-2.86 (m, 5H), 2.62-2.57 (m, 3H), 2.36 (s, 3H), 2.17 (m, 2H), 2.09 (s, 3H); MS (ESI+) m/z 611.2 (M+H).

N-(3-(6-(4-(1,4-Dimethyl-3-oxopiperazin-2-yl)phenylamino)-4-methyl-5-oxo-4,5-dihydropyrazin-2-yl)-2-methylphenyl)-7-hydroxy-4,5,6,7-tetrahydrobenzo[b]thiophene-2-carboxamide (18)

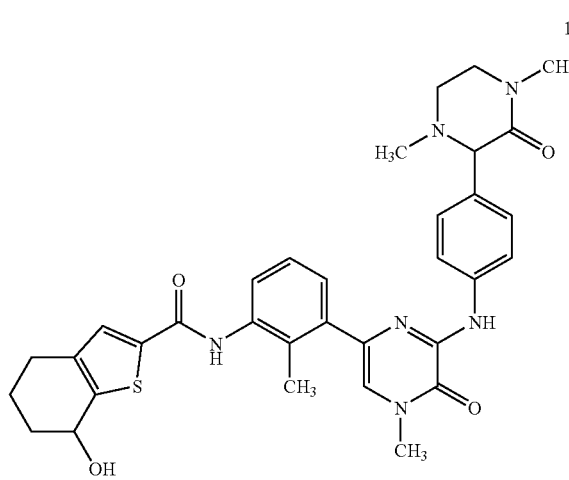

A 50-mL single-neck round-bottomed flask equipped with a magnetic stirrer was purged with nitrogen and charged with 17 (250 mg, 0.409 mmol) and methanol (10 mL). The resulting solution was cooled to 0° C., and sodium borohydride (31 mg, 0.819 mmol) was added. After stirring the reaction at room temperature for 2 h, the solvent was evaporated under reduced pressure. The resulting residue was purified by flash chromatography to afford 18 in 88% yield (220 mg) as a white solid: mp 165-166° C.; $^1$H NMR (500 MHz, CD$_2$Cl$_2$) δ 8.38 (s, 1H), 7.90 (d, 1H, J=7.5 Hz), 7.81 (d, 2H, J=8.5 Hz), 7.71 (s, 1H), 7.39 (s, 1H), 7.34-7.27 (m, 4H), 6.80 (s, 1H), 4.94 (m, 1H), 3.72 (td, 1H, J=11.5, 4.5 Hz), 3.65 (s, 1H), 3.62 (s, 3H), 3.21 (m, 1H), 3.01 (m, 1H), 2.95 (s, 3H), 2.76-2.62 (m, 3H), 2.43 (s, 3H), 2.22-2.13 (m, 5H), 2.02 (m, 1H), 1.83 (m, 2H); MS (ESI+) m/z 595.2 (M+H).

EXAMPLES 3A AND 3B

N-(3-(6-(4-((2R)-1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (19)

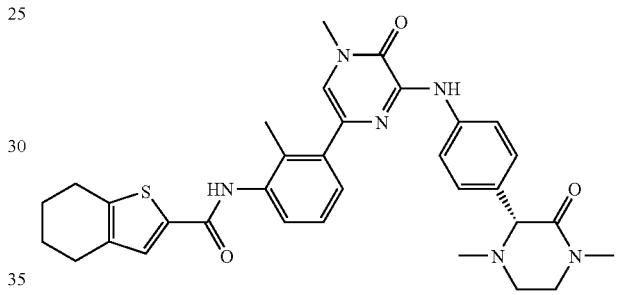

N-(3-(6-(4-((2S)-1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide (20)

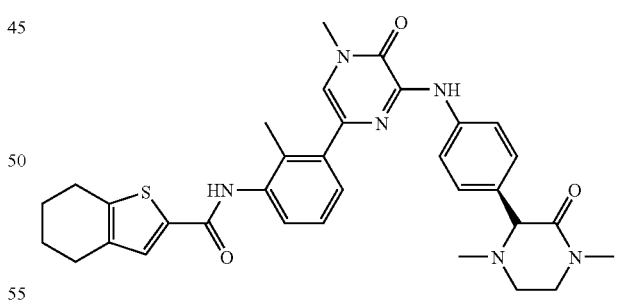

The racemic mixture (12) was subjected to chiral separation on Chiralcel-AD-H (60% isopropanol in heptane, with 0.1% trifluoroacetic acid) to give individual enantiomers at 4.6 minutes (20) ((−) isomer) ([α]$_D^{25}$=−37.8° (c=3.75, CHCl$_3$), mp=181-183° C.) and at 9.2 minutes (19) ((+) isomer) ([α]$_D^{25}$=+38.8° (c=3.57, CHCl$_3$), mp=180-182° C.). Alternatively, the racemic mixture (12) was subjected to chiral separation on Chiralpak AD (75% isopropanol in heptane, at 1 mL/min) and individual enantiomers were collected from 17 to 27 minutes (20) ((−) isomer) and from 27 to 60 minutes (19) ((+) isomer).

Alternatively, racemic mixture (4) was subjected to separation on Chiralpak AD (30% i-propanol/heptane 0.1% trifluoroacetic acid) to give individual enantiomers at 5.4 minutes (S-isomer) and 14.9 minutes (R-isomer). The individual isomers 19 and 20 were then prepared using the general synthetic routes described in Example 1 or Example 2.

5-Bromo-3-(4-((S)-1,4-dimethyl-3-oxopiperazin-2yl) phenylamino)-1-methylpyrazin-2(1H)-one ((S)-14)

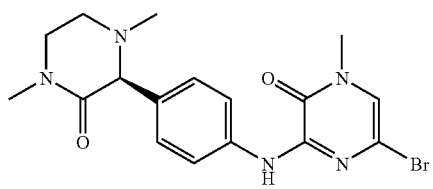

(S)-14

To a single-necked 250 mL round-bottomed flask equipped with a magnetic stirrer and reflux condenser was charged (−)-1,4-dimethyl-3-(4-aminophenyl)piperazin-2-one (8.2 g, 37.3 mmol), 3,5-dibromo-1-methylpyrazin-2(1H)-one (10.0 g, 37.3 mmol), and i-PrOH (100 mL). Triethylamine (5.72 mL, 41 mmol, 1.1 eq) was then added and the resulting suspension was heated at 80° C. for 16 hrs. A thick slurry was observed the following day. The reaction was cooled to room temperature then concentrated in vacuo to ~20 mL total volume. At that point 20 mL of 2M Na₂CO₃ solution was added followed by 100 mL of water. The mixture was then allowed to slurry for 2 hrs at room temperature. The off-white solid was then collected on a fritted funnel and allowed to air dry for ~1 hr. The solids were returned to the reaction flask and 100 mL of diethyl ether/hexanes (1:1) was added and the suspension was triturated at room temperature for 1 hr. The white solid was then collected on a fritted funnel, dried on the filter with vacuum for 1 hr, then transferred to a round-bottomed flask and vacuum-dried overnight. White solids were obtained, 12.88 g (85%).

5-Bromo-3-(4-((R)-1,4-dimethyl-3-oxopiperazin-2yl)phenylamino)-1-methylpyrazin-2(1H)-one ((R)-14)

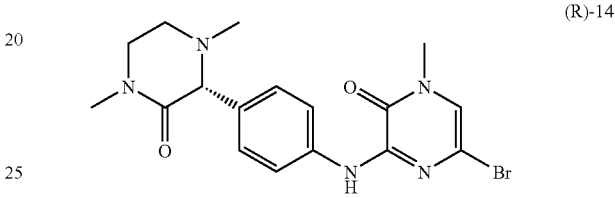

(R)-14

The (R)-isomer of compound 14 can be prepared from the (+)-isomer of 1,4-dimethyl-3-(4-aminophenyl)piperazin-2-one using the same procedure.

EXAMPLE 4

Scheme 4

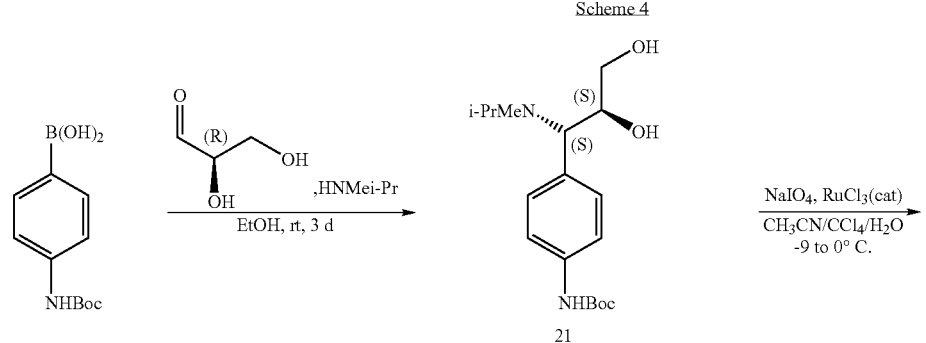

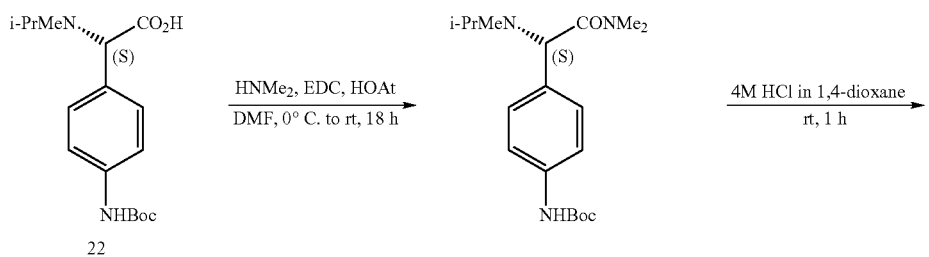

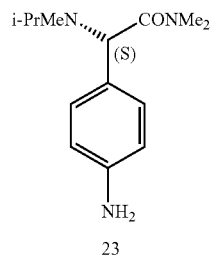

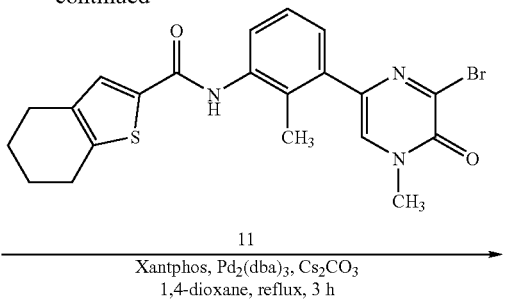

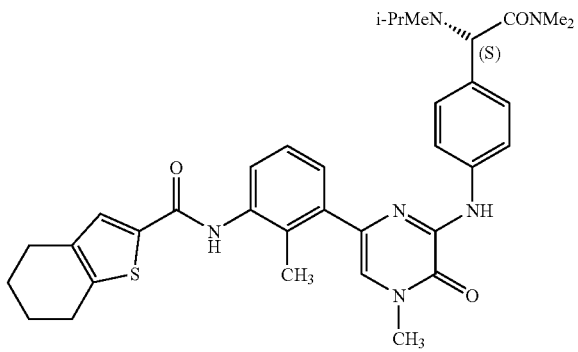

tert-Butyl 4-((1S,2S)-2,3-dihydroxy-1-isopropyl(methyl)amino)propyl)-phenylcarbamate (21)

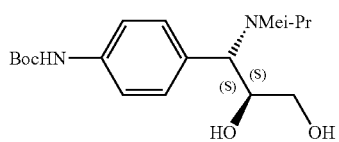

A 50-mL single-neck round-bottomed flask equipped with a magnetic stirrer was charged with D-(+) glyceraldehyde (90% purity, 1.62 g, 16.2 mmol), ethanol (16 mL), N,N-methylisopropylamine (1.19 g, 16.3 mmol) and 4-(tert-butoxycarbonylamino)-phenylboronic acid (3.85 g, 16.2 mmol). The flask was sealed with a teflon stopper, and the reaction mixture was stirred for 3 d. After this time the mixture was evaporated to dryness under reduced pressure. The residue was dissolved in 10 mL of 2M aqueous sodium hydrogensulfate (20.0 mmol). The resulting solution was extracted with methyl tert-butyl ether (2×150 mL), and the aqueous layer was basified by adding potassium carbonate (2.76 g, 20.0 mmol). The suspension was extracted with ether (2×50 mL), and the organic extracts were combined and dried over sodium sulfate. After removing the drying agent by filtration, the solution was evaporated under reduced pressure to afford a 69% yield (3.79 g) of 21 as a white solid: mp 61-80° C.; $^1$H NMR (300 MHz, DMSO-$d_6$) δ 9.23 (br s, 1H), 7.33 (d, 2H, J=8.4 Hz), 7.16 (d, 2H, J=8.5 Hz), 4.58 (t, 1H, J=5.3 Hz), 4.22 (d, 1H, J=4.7 Hz), 3.96 (quintet, 1H, J=5.4 Hz), 3.49 (d, 1H, J=6.2 Hz), 3.30 (m, 1H), 3.15 (m, 1H), 2.83 (septet, 1H, J=6.5 Hz), 2.06 (s, 3H), 1.47 (s, 9H), 0.85 (d, 3H, J=6.6 Hz), 0.79 (d, 3H, J=6.5 Hz); MS (ESI+) m/z 339 (M+H).

(S)-2-(4-(tert-Butoxycarbonylamino)phenyl)-2-(isopropyl(methyl)amino)acetic Acid (22)

(22)

BocHN—⟨phenyl⟩—CH(NMei-Pr)(S)CO$_2$H

A 100-mL single-neck round-bottomed flask equipped with a magnetic stirrer was charged with 21 (1.01 g, 3.00 mmol), acetonitrile (6 mL), carbon tetrachloride (6 mL), water (9 mL) and ruthenium(III) chloride monohydrate (39 mg, 0.17 mmol); and the resulting mixture was stirred for 10 min. The reaction was cooled to −9° C., and sodium periodate (2.56 g, 12.0 mmol) was added. The mixture was slowly warmed to 0° C. over 1.5 h, and then stirred at 0° C. for 1 h and filtered. The filter cake was washed with ice-cold water (2×5 mL), and the filtrate was diluted with additional water (20 mL). The aqueous layer was separated, its acidity was adjusted to pH 5.8, and it was evaporated to dryness. The residue was triturated with water (10 mL) and the resulting suspension was filtered. The filter cake was washed with water (2×1 mL) and methyl tert-butyl ether (2×5 mL), and dried overnight under reduced pressure to afford a 13% yield of 22 (121 mg) as a white solid: $^1$H NMR (300 MHz, DMSO-$d_6$) δ 9.40 (s, 1H), 7.41 (d, 2H, J=8.8 Hz), 7.36 (d, 2H, J=8.8 Hz), 4.19 (s, 1H), 3.27 (septet, 1H, J=6.6 Hz), 2.21 (s, 3H), 1.47 (s, 9H), 1.13 (d, 3H, J=6.6 Hz), 1.09 (d, 3H, J=6.6 Hz); MS (ESI+) m/z 323 (M+H).

1(S)-2-(4-Aminophenyl)-2-(isopropyl(methyl)amino)-N,N-dimethylacetamide (23)

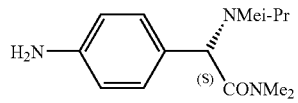

(23)

A 25-mL single-neck round-bottomed flask equipped with a magnetic stirrer was purged with nitrogen and charged with 22 (116 mg, 0.36 mmol), 1-hydroxy-7-azabenzotriazole (50 mg, 0.37 mmol), N-(3-dimethylaminopropyl)-N'-ethylcarbodiimide hydrochloride (208 mg, 1.08 mmol) and DMF (2 mL), and the mixture was cooled to 0° C. A 2M solution of dimethylamine in THF (0.3 mL, 0.6 mmol) was added, and the reaction was allowed to warm slowly to room temperature overnight. A solution of potassium carbonate (2.00 g) in water (10 mL) was added, and the mixture was extracted with hexanes (3×30 mL). The hexanes extracts were combined, dried over sodium sulfate, filtered, and evaporated to dryness. The resulting crude product was mixed with methylene chloride (1 mL) and 4M solution of hydrogen chloride in dioxane (10 mL). The resulting emulsion was vigorously stirred for 1 h at room temperature. After this time, the solvents were evaporated under reduced pressure, and the resulting residue was treated with water (2 mL) followed by potassium carbonate (1.0 g), and then extracted with MtBE (10 mL). The extract was evaporated and the residue was purified by flash chromatography on silica gel to afford a 58% yield (53 mg) of 23 as a light yellow oil: $^1$H NMR (300 MHz, CDCl$_3$/CD$_3$OD) δ 7.20 (d, 2H, J=8.5 Hz), 6.69 (d, 2H, J=8.5 Hz), 4.56 (s, 1H), 3.02 (s, 3H), 2.97 (m, 1H), 2.91 (s, 3H), 2.11 (s, 3H), 1.03 (d, 3H, J=6.7 Hz), 1.00 (d, 3H, J=6.6 Hz).

(S)-(+)-N-(3-(6-(4-(2-(Dimethylamino)-1-(isopropyl(methyl)amino)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide (24)

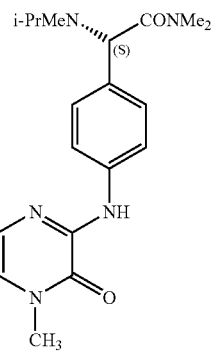

(24)

A 15-mL three-neck round-bottomed flask equipped with a magnetic stirrer, nitrogen inlet and reflux condenser was charged with 23 (53 mg, 0.212 mmol), 11 (98 mg, 0.212 mmol), cesium carbonate (152 mg, 0.468 mmol) and 1,4-dioxane (3 mL). After bubbling nitrogen through the resulting solution for 30 minutes, Xantphos (10.4 mg, 0.018 mmol) and tris(dibenzylideneacetone)dipalladium(0) (9.70 mg, 0.010 mmol) were added and the reaction mixture was heated at reflux for 3 h. After this time the reaction was cooled to room temperature, filtered and the filter cake washed with methylene chloride (2×25 mL). The filtrate was then concentrated under reduced pressure and the residue was purified by column chromatography to afford 24 (68 mg, 52%) as a yellow solid: mp 133-134° C.; $^1$H NMR (500 MHz, DMSO-d$_6$) δ 9.79 (br s, 1H), 9.19 (br s, 1H), 7.93 (d, 2H, J=8.5 Hz), 7.68 (s, 1H), 7.30 (m, 5H), 7.20 (s, 1H), 4.56 (s, 1H), 3.55 (s, 3H), 3.01 (s, 3H), 2.84 (m, 1H), 2.76 (m, 5H), 2.63 (t, 2H, J=5.5 Hz), 2.28 (s, 3H), 2.02 (s, 3H), 1.79 (m, 4H), 0.91 (m, 6H); MS (ESI+) m/z 627.5 (M+H); $[\alpha]^{25}_D$+24.0° (c 0.25, chloroform).

EXAMPLE 5

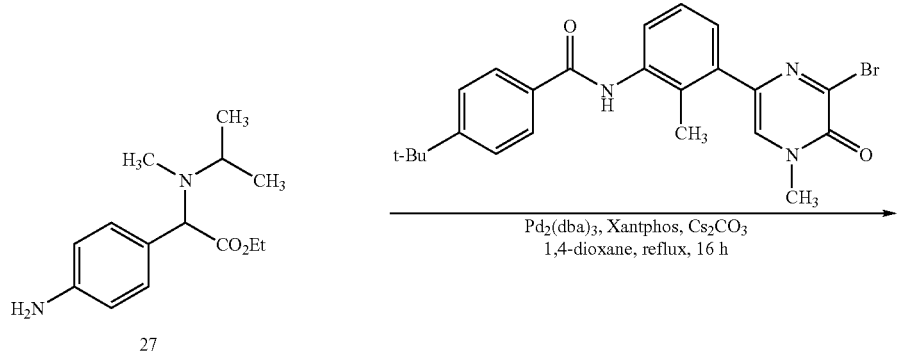

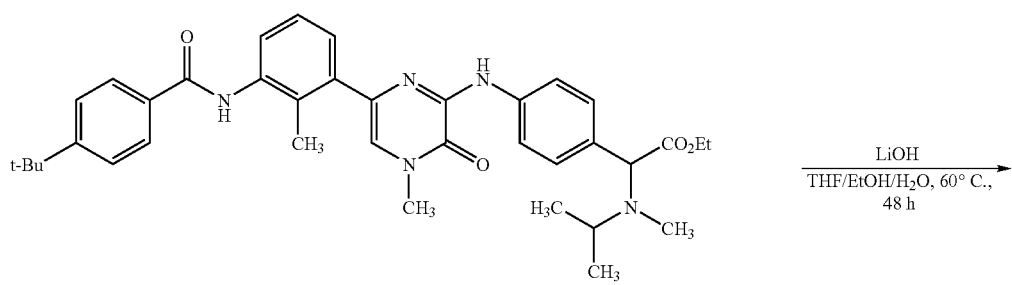

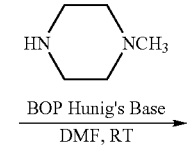

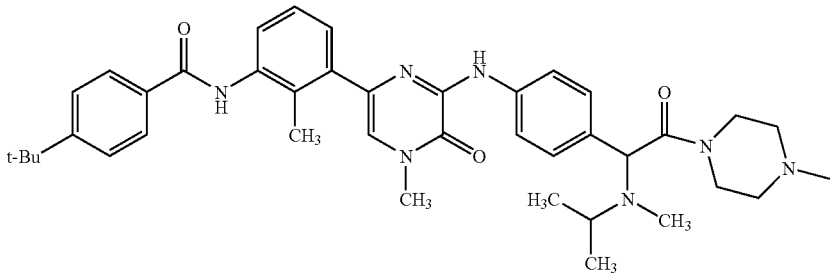

2-[4-(tert-Butoxycarbonylamino)phenyl]-2-[isopropyl(methyl)amino]acetic Acid (25)

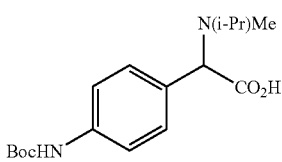

A 50-mL single-neck round-bottomed flask equipped with a magnetic stirrer was charged with glyoxylic acid (618 mg, 6.72 mmol), toluene (20 mL), N,N-isopropylmethylamine (486 mg, 6.60 mmol) and 4-(tert-butoxycarbonylamino)phenylboronic acid (1.58 g, 6.66 mmol). The reaction was sealed with a plastic cap under a nitrogen atmosphere and stirred at room temperature for 7 d. After this time, the reaction was concentrated under reduced pressure. The resulting residue was subjected to flash chromatography to afford 25 in 62% yield (1.34 g) as a light brown solid: mp 320° C. dec, $^1$H NMR (300 MHz, DMSO-$d_6$) δ 9.42 (s, 1H), 7.42 (d, 2H, J=8.7 Hz), 7.37 (d, 2H, J=8.7 Hz), 4.23 (s, 1H), 3.28 (m, 1H), 3.17 (s, 1H), 2.23 (s, 3H), 1.47 (s, 9H), 1.15 (d, 3H, J=6.6 Hz), 1.11 (d, 3H, J=6.6 Hz); MS (ESI+) m/z 323 (M+H).

Ethyl 2-[4-(tert-Butoxycarbonylamino)phenyl]-2-[isopropyl(methyl)amino]acetate (26)

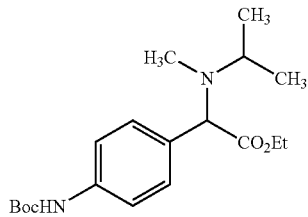

A 250-mL single-neck round-bottomed flask equipped with a magnetic stirrer was purged with nitrogen and charged with 25 (1.50 g, 4.66 mmol), THF (45 mL), 1-hydroxy-7-azabenzotriazole (1.27 g, 9.32 mmol) and 1-ethyl-3-[3-dimethyl amino)propyl]-carbodiimide hydrochloride (1.79 g, 9.32 mmol), and the reaction mixture was stirred for 15 min. Ethanol (429 mg, 9.32 mmol) and 4-dimethylamino pyridine (57 mg, 0.47 mmol) were added, and the reaction mixture was stirred at room temperature for a further 16 h. After this time, the reaction was partitioned between water (40 mL) and methylene chloride (50 mL). The layers were separated, and the aqueous phase was extracted with methylene chloride (2×30 mL). The organic extracts were combined and dried over sodium sulfate. The drying agent was removed by filtration, and the solvent was evaporated under reduced pressure. The resulting residue was dried to a constant weight under vacuum to afford 26 in 73% yield (1.20 g) as a white solid: mp 87-88° C.; $^1$H NMR (500 MHz, DMSO-$d_6$) δ 9.35 (s, 1H), 7.40 (d, 2H, J=7.5 Hz), 7.28 (d, 2H, J=7.5 Hz), 4.16 (s, 1H), 4.05 (m, 2H), 2.80 (septet, 1H, J=6.5 Hz), 2.02 (s, 3H), 1.47 (s, 9H), 1.11 (t, 3H, J=7.0 Hz), 0.94 (d, 3H, J=6.5 Hz), 0.88 (d, 3H, J=6.5 Hz); MS (ESI+) m/z 351 (M+H).

Ethyl 2-(4-Aminophenyl)-2-[isopropyl(methyl)amino]acetate (27)

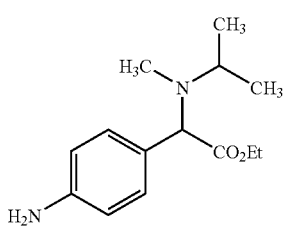

A 100-mL single-neck round-bottomed flask equipped with a magnetic stirrer was charged with 26 (1.19 g, 3.40 mmol) and 4M hydrogen chloride in 1,4-dioxane (15.0 mL, 60 mmol), and the mixture was stirred at room temperature for 4 h. After this time, the reaction mixture was concentrated under reduced pressure, and the resulting residue was partitioned between 10% aqueous potassium carbonate (100 mL) and methylene chloride (75 mL). The layers were separated, and the aqueous phase was extracted with methylene chloride (2×75 mL). The combined organic extracts were dried over sodium sulfate, filtered and concentrated under reduced pressure to afford 27 in 81% yield (878 mg) as an orange solid: mp 70-71° C.; $^1$H NMR (500 MHz, DMSO-$d_6$) δ 7.02 (d, 2H, J=7.5 Hz), 6.49 (d, 2H, J=7.5 Hz), 5.07 (bs, 2H), 4.07-3.97 (m, 3H), 2.81 (septet, 1H, J=6.5 Hz), 1.99 (s, 3H), 1.11 (t, 3H, J=7.0 Hz), 0.92 (d, 3H, J=6.5 Hz), 0.85 (d, 3H, J=6.5 Hz); MS (ESI+) m/z 251 (M+H).

Ethyl 2-(4-{6-[3-(4-tert-Butylbenzamido)-2-methylphenyl]-4-methyl-3-oxo-3,4-dihydropyrazin-2-ylamino}phenyl)-2-[isopropyl(methyl)amino]acetate (28)

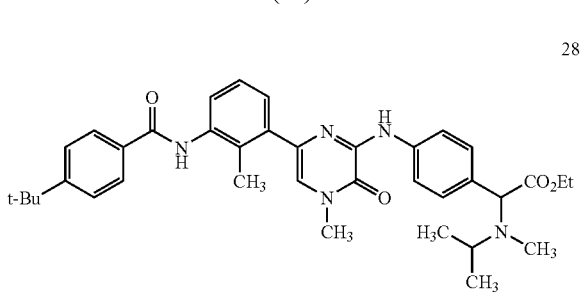

A 50-mL single-neck round-bottomed flask equipped with a magnetic stirrer, nitrogen inlet and reflux condenser was charged with 27 (435 mg, 1.74 mmol), 4-tert-butyl-N-{2-methyl-3-(4,4,5,5,-tetramethyl-[1,3,2]dioxaborolan-2-yl)-phenyl)-benzamide (717 mg, 1.58 mmol), cesium carbonate (1.13 g, 3.48 mmol) and 1,4-dioxane (15 mL). After bubbling nitrogen through the resulting solution for 20 minutes, Xantphos (78 mg, 0.134 mmol) and tris(dibenzylideneacetone) dipalladium(0) (72 mg, 0.079 mmol) were added, and the reaction mixture was heated at reflux for 16 h. After this time, the reaction was cooled to room temperature, filtered and concentrated under reduced pressure. The resulting residue was purified by flash chromatography to afford a 43% yield (430 mg) of 28 as a yellow solid: mp 119-120° C.; $^1$H NMR (500 MHz, DMSO-$d_6$) δ 9.88 (s, 1H), 9.24 (s, 1H), 7.97 (d, 2H, J=8.5 Hz), 7.95 (d, 2H, J=8.5 Hz), 7.55 (d, 2H, J=8.5 Hz), 7.37 (dd, 1H, J=6.5, 3.5 Hz), 7.31 (d, 2H, J=8.5 Hz), 7.28 (m, 2H), 7.22 (s, 1H), 4.18 (s, 1H), 4.04 (m, 2H), 3.56 (s, 3H), 2.81 (septet, 1H, J=6.5 Hz), 2.29 (s, 3H), 2.02 (s, 3H), 1.33 (s, 9H), 1.11 (t, 3H, J=7.0 Hz), 0.94 (d, 3H, J=6.5 Hz), 0.88 (d, 3H, J=6.5 Hz); MS (ESI+) m/z 624 (M+H).

2-(4-{6-[3-(4-tert-Butylbenzamido)-2-methylphenyl]-4-methyl-3-oxo-3,4-dihydropyrazin-2-ylamino}phenyl)-2-[isopropyl(methyl)amino]acetic Acid (29)

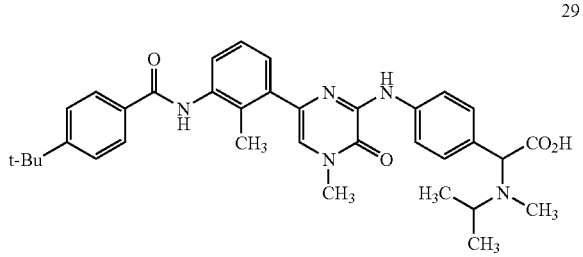

A 100-mL single-neck round-bottomed flask equipped with a magnetic stirrer and reflux condenser was charged with 28 (400 mg, 0.642 mmol), THF (5 mL) and ethanol (5 mL). A solution of lithium hydroxide (124 mg, 10.2 mmol) in water (5 mL) was added, and the mixture was heated at 60° C. for 48 h. After this time, the reaction was cooled to room temperature, and the mixture was slowly acidified to pH 4.0 with 10% aqueous citric acid. The resulting precipitate was filtered, and the filter cake was washed with water (20 mL), then triturated with a 1:10 mixture of methylene chloride/ethyl acetate (20 mL). The resulting residue was dried to a constant weight under vacuum at 45° C. to afford 29 in 55% yield (210 mg) as an off-white solid: mp 197-198° C.; $^1$H NMR (500 MHz, DMSO-$d_6$) δ 9.91 (s, 1H), 9.29 (s, 1H), 7.99 (d, 2H, J=8.5 Hz), 7.95 (d, 2H, J=8.5 Hz), 7.55 (d, 2H, J=8.5 Hz), 7.39 (d, 2H, J=8.5 Hz), 7.35 (dd, 1H, J=7.0, 1.5 Hz), 7.32-7.28 (m, 2H), 7.24 (s, 1H), 4.23 (s, 1H), 3.56 (s, 3H), 3.30 (m, 1H), 2.30 (s, 3H), 2.23 (s, 3H), 1.33 (s, 9H), 1.13 (d, 3H, J=6.5 Hz), 1.10 (d, 3H, J=6.5 Hz); MS (ESI+) m/z 596 (M+H).

4-tert-Butyl-N-(3-(6-(4-(1-(isopropyl(methyl)amino)-2-(4-methylpiperazin-1-yl)-2-oxoethyl)phenylamino)-4-methyl-5-oxo-4,5-dihydropyrazin-2-yl)-2-methylphenyl)benzamide (30)

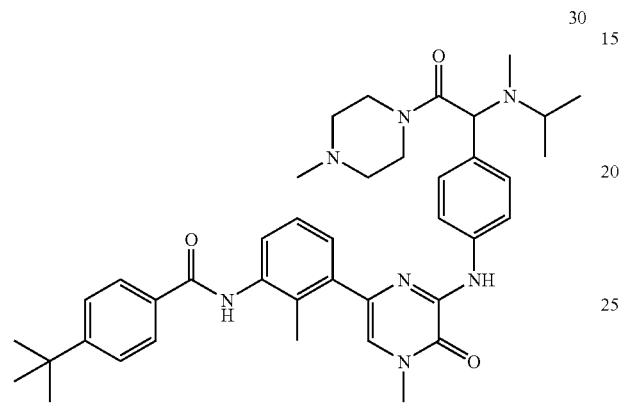

To a sealed tube equipped with a magnetic stirrer, were charged 29 (100 mg, 0.168 mmol), 1-methylpiperazine (14.6 mg, 0.168 mmol), DMF (3 mL), Hunig's base (65.1 mg, 0.503 mmol), and BOP (74.3 mg, 0.168 mmol). The reaction mixture was stirred at room temperature for 26 hrs. Most solvent was removed by rotary evaporation and the resulting residue was dissolved in ethyl acetate (100 mL). The solution was washed with water (15 mL×3), dried over MgSO$_4$, filtered and solvent removed in vacuo. Silica gel column chromatography (MeOH:CH$_2$Cl$_2$=5:95) afforded 30 as a light yellow solid, 25 mg (22%). $^1$H NMR (300 MHz, CDCl$_3$) δ8.45 (s, 1 H), 8.09 (s, 1 H), 7.95 (s, 1 H), 7.92 (s, 1 H), 7.85 (m, 2 H), 7.75 (m, 1 H), 7.54 (s, 1 H), 7.51 (s, 1 H), 7.40 (m, 2 H), 7.19-7.23 (m, 2 H), 6.79 (s, 1 H), 5.19 (s, 1 H), 3.62 (s, 3 H), 3.40 (broad s, 2 H), 3.21 (broad s, 2 H), 2.26-2.50 (m, 9 H), 2.18 (s, 3 H), 1.92 (broad s, 2 H), 1.34 (s, 9 H), 1.25-1.31 (m, 6 H) ppm; MS (ESI+) m/z 678.19 (M+H).

EXAMPLE 6

3-(4-Nitrophenyl)-5,6-dihydropyrazin-2(1H)-one (31)

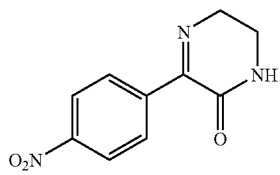

A 50-mL single-neck round-bottomed flask equipped with a magnetic stirrer was purged with nitrogen, charged with ethyl 4-nitrophenylpyruvate (223 mg, 1.00 mmol), 3 pieces of molecular sieves (4-8 mesh, 3A) and anhydrous methanol (10 mL). The resulting solution was cooled to 0° C. with an ice bath and 1,2-ethylenediamine (63 mg, 1.05 mmol) was added dropwise. After addition was complete the reaction was stirred at room temperature for 1 h. After this time the resulting suspension was filtered and the filter cake washed with cold methanol (2×5 mL). The filter cake was dried in an oven at 50° C. overnight under vacuum to afford 31 in 89% yield (196 mg) as a white solid: mp 191-192° C.; $^1$H NMR (500 MHz, DMSO-$d_6$) δ 8.63 (bs, 1H), 8.26 (d, 2H, J=8.0 Hz), 8.09 (d, 2H, J=8.0 Hz), 3.88 (t, 2H, J=6.5 Hz), 3.37 (m, 2H); MS (ESI+) m/z 220 (M+H).

4-Ethyl-3-(4-nitrophenyl)piperazin-2-one (32)

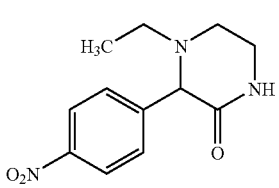

A 10-mL single-neck round-bottomed flask equipped with a magnetic stirrer was purged with nitrogen, charged with 31 (2.78 g, 12.7 mmol), acetaldehyde (727 mg, 16.5 mmol) and anhydrous methanol (40 mL). A solution of sodium cyanoborohydride (2.4 g, 38 mmol) and anhydrous zinc chloride (2.6 g, 19.1 mmol) in anhydrous methanol (40 mL) was added, and the reaction was stirred at room temperature for 1 h. After this time, 1N aqueous sodium hydroxide (25 mL) was added, and the methanol was evaporated under reduced pressure. The remaining aqueous solution was extracted with ethyl acetate (3×100 mL). The organic layers were combined, washed with water (100 mL) and brine (100 mL) and dried over magnesium sulfate. The drying agent was removed by filtration and the filtrate concentrated under reduced pressure to afford a 98% yield (3.20 g) of 32 as a yellow oil: $^1$H NMR (500 MHz, DMSO-$d_6$) δ 8.18 (d, 2H, J=8.5 Hz), 8.02 (d, 1H, J=4.0 Hz), 7.66 (d, 2H, J=8.5 Hz), 4.06 (s, 1H), 3.39 (td, 1H, J=12.0, 4.0 Hz), 3.22 (m, 1H), 3.07 (dt, 1H, J=12.0, 3.0 Hz), 2.50 (m, 1H), 2.37 (m, 1H), 2.21 (m, 1H), 0.91 (t, 3H, J=8.5 Hz); MS (ESI+) m/z 250 (M+H).

3-(4-Aminophenyl)-4-ethylpiperazin-2-one (33)

A 25-mL single-neck round-bottomed flask equipped with a reflux condenser and magnetic stirrer was purged with nitrogen and charged with 32 (210 mg, 0.89 mmol), ethanol (6 mL), iron powder (–325 mesh, 491 mg, 8.93 mmol) and 2N hydrochloric acid (0.70 mL, 1.40 mmol), and the mixture was heated at reflux for 30 min. After this time, the reaction was cooled to room temperature, and powdered potassium carbonate (3.03 g, 22.0 mmol) was added. The resulting suspension was filtered and the filter cake washed with ethanol (4×10 mL). The filtrate was concentrated under reduced pressure to afford 33 in 100% yield (185 mg) as a white solid: mp 153-154° C.; 1H NMR (300 MHz, DMSO-d6) δ 7.74 (d, 1H, J=2.7 Hz), 6.90 (d, 2H, J=8.4 Hz), 6.47 (d, 2H, J=8.4 Hz), 4.95 (bs, 2H), 3.45 (m, 1H), 3.42 (s, 1H), 3.14 (m, 1H), 2.89 (m, 1H), 2.44 (m, 1H), 2.02 (s, 3H); MS (ESI+) m/z 206 (M+H).

5-Bromo-3-(4-(1-ethyl-3-oxopiperazin-2-yl)phenylamino]-1-methylpyrazin-2(1H)-one (34)

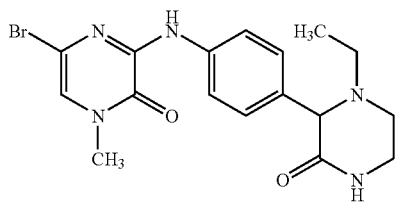

34

A 100-mL single-neck round-bottomed flask equipped with a magnetic stirrer and reflux condenser was charged with 33 (450 mg, 2.05 mmol), isopropanol (5 mL), 13 (603 mg, 2.26 mmol) and DL-10-camphorsulfonic acid (813 mg, 3.50 mmol), and the reaction mixture was then stirred at reflux for 16 h. After this time, the reaction mixture was cooled to room temperature, filtered and the filter cake washed with isopropanol (10 mL). The resulting solid was dissolved in methylene chloride/methanol (3:1), absorbed onto silica gel and purified by flash chromatography to afford 34 in 79% yield (654 mg) as an orange solid: mp 152-153° C.; 1H NMR (500 MHz, CDCl3) δ8.28 (bs, 1H 7.73 (d, 2H, J=8.5 Hz), 7.43 (d, 2H, J=8.5 Hz), 6.74 (s, 1H), 5.90 (d, 1H, J=3.5 Hz), 4.12 (s, 1H), 3.60 (m, 1H), 3.52 (s, 3H), 3.36 (m, 1H), 3.12 (m, 1H), 2.60 (m, 2H), 2.28 (m, 1H), 1.00 (t, 3H, J=7.0 Hz); MS (ESI+) m/z 406.0 (M+H).

N-(3-(6-(4-(1-Ethyl-3-oxopiperazin-2-yl)phenylamino)-4-methyl-5-oxo-4,5-dihydropyrazin-2-yl)-6-fluoro-2-methylphenyl)-4,5,6,7-tetrahydrobenzo[b]thiophene-2-carboxamide (35)

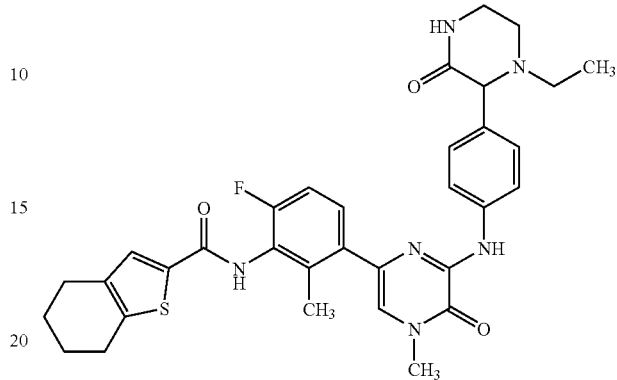

A 100-mL single-neck round-bottomed flask equipped with a magnetic stirrer, reflux condenser and nitrogen inlet was charged with 1,4-dioxane (13 mL), water (3 mL) and sodium carbonate (417 mg, 3.93 mmol). After bubbling nitrogen through the resulting mixture for 15 min, 34 (150 mg, 0.370 mmol), N-(6-Fluoro-2-methyl-3-(4,4,5,5-tetramethyl-1,3,2-dioxaborolan-2-yl)phenyl)-4,5,6,7-tetrahydro benzo[b]thiophene-2-carboxamide. (192 mg, 0.460 mmol and tetrakis(triphenyl phosphine)palladium(0) (75 mg, 0.065 mmol) were added, and the reaction mixture then heated at reflux for 5 h. After this time, the reaction mixture was cooled to room temperature, filtered and the filter cake washed with diethyl ether (10 mL). The resulting solid was dissolved in methylene chloride/methanol (10:1), absorbed onto silica gel and purified by flash chromatography to afford 35 in 41% yield (93 mg) as a yellow solid: mp 179-180° C.; 1H NMR (500 MHz, CDCl3) δ 8.31 (bs, 1H), 7.79 (d, 2H, J=8.5 Hz), 7.39 (m, 3H), 7.33 (m, 1H), 7.22 (s, 1H), 7.04 (t, 1H, J=8.0 Hz), 6.68 (s, 1H), 5.80 (d, 1H, J=3.5 Hz), 3.99 (s, 1H), 3.65 (s, 3H), 3.64 (m, 1H), 3.36 (m, 1H), 3.11 (m, 1H), 2.82 (t, 2H, J=6.0 Hz), 2.66 (t, 2H, J=6.0 Hz), 2.59 (m, 2H), 2.36 (s, 3H), 2.27 (m, 1H), 1.85 (m, 4H), 0.99 (t, 3H, J=7.0 Hz); MS (ESI+) m/z 615.3 (M+H).

EXAMPLE 7

Scheme 7

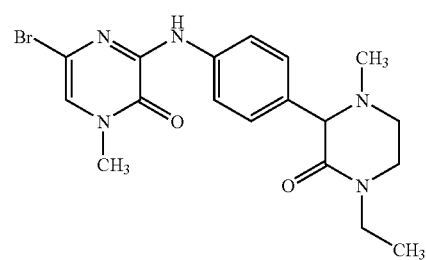

34

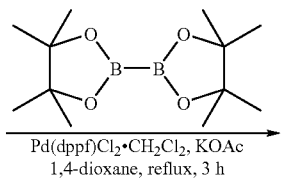

Pd(dppf)Cl2·CH2Cl2, KOAc
1,4-dioxane, reflux, 3 h

-continued

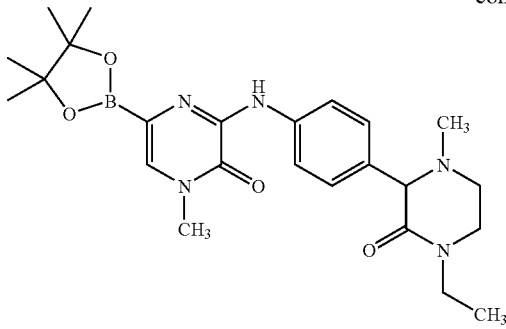

39

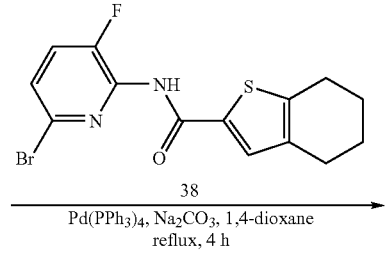

38
—————————→
Pd(PPh₃)₄, Na₂CO₃, 1,4-dioxane
reflux, 4 h

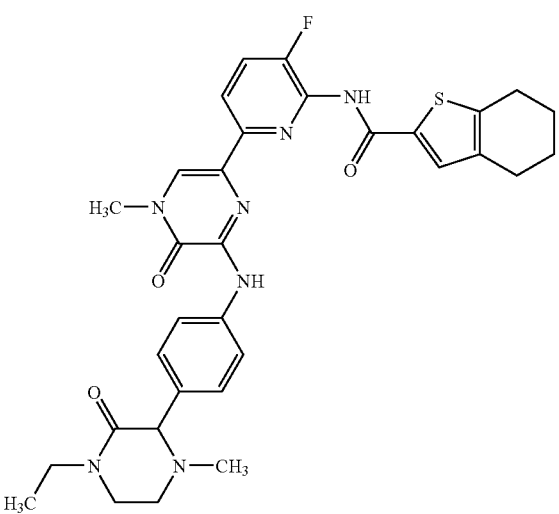

40

2,6-Dibromopyridine-3-diazonium Tetrafluoroborate (36)

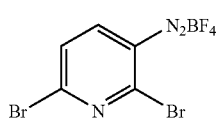

36

A 500-mL three-neck round-bottomed flask equipped with a magnetic stirrer, nitrogen inlet and addition funnel was purged with nitrogen and charged with 2,6-dibromo-3-aminopyridine (25.0 g, 99.2 mmol) and 1,2-dimethoxyethane (70 mL), and the solution was cooled to −10° C. using an ice/acetone bath. A solution of boron trifluoride-diethyl etherate (21.1 g, 148 mmol) in 70 mL of 1,2-dimethoxyethane was added at such a rate at to maintain the internal reaction temperature below −5° C. After the addition was complete, a solution of tert-butyl nitrite (12.2 g, 118 mmol) in 70 mL of 1,2-dimethoxyethane was added dropwise maintaining the internal reaction temperature below −5° C. The reaction was stirred for a further 1 h at −10° C. After this time the reaction was filtered and the filter cake was washed with hexanes (3×75 mL) and dried at room temperature on air for 24 h, to afford a 98% yield (34.1 g) of 36 as a white solid: mp 130-131° C.; ¹H NMR (300 MHz, DMSO-d₆) δ7.72 (d, 1H, J=9.6 Hz), 5.66 (d, 1H, J=9.6 Hz).

2,6-Dibromo-3-fluoropyridine (37)

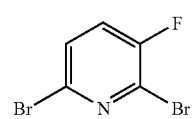

37

A 1-L single-neck round-bottomed flask equipped with a reflux condenser open to air was charged with 36 (4.00 g, 11.4 mmol) which was equally distributed on the flask bottom and placed in an oil bath at room temperature. The bath was heated to 80° C. over 20 min, then the bath temperature was gradually increased to 130° C. over 30 min, until a decomposition occurred at an oil bath temperature of 130° C. Once all of the powder had visibly decomposed (the solid was transformed to a goo and the evolution of gas stopped), the reaction was cooled to room temperature and the resulting residue extracted with diethyl ether (3×75 mL) decanting the ether extracts. The organic extracts were combined, washed with saturated aqueous sodium bicarbonate (200 mL) and dried over sodium sulfate. The drying agent was removed by filtration, and the filtrate was concentrated under reduced pressure at room temperature to afford a 100% yield (3.00 g) of 37 as a yellow solid: mp 47-48° C.; ¹H NMR (300 MHz, CDCl₃) δ 7.44 (dd, 1H, J=3.3, 8.4 Hz), 7.31 (m, 1H).

N-(6-Bromo-3-fluoropyridin-2-yl)-4,5,6,7-tetrahydrobenzo[b]thiophene-2-carboxamide (38)

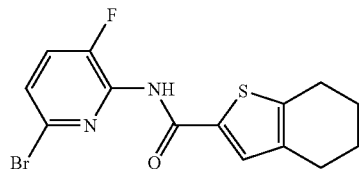

A 1-L three-neck round-bottomed flask equipped with a mechanical stirrer, reflux condenser and nitrogen inlet was charged with 1,4-dioxane (56 mL), 37 (3.00 g, 11.7 mmol), 4,5,6,7-tetrahydrobenzo[b]thiophene-2-carboxamide (1.29 g, 7.12 mmol) and cesium carbonate (5.09 g, 15.6 mmol). After bubbling nitrogen through the resulting solution for 30 min, Xantphos (350 mg, 0.605 mmol) and tris(dibenzylideneacetone)-dipalladium(0) (326 mg, 0.365 mmol) were added and the reaction mixture was heated at reflux for 2 h. After this time the reaction was cooled to room temperature and filtered through a pad of Celite 521. The filter cake was washed with methylene chloride (50 mL). The filtrate was concentrated under reduced pressure and the resulting residue was purified by column chromatography using 500 cc of silica and eluting with 5% EtOAc/hexanes to afford a 37% yield of 38 (940 mg) a white solid: $R_f$=0.55 (20% ethyl acetate in hexanes); $^1$H NMR (500 MHz, CDCl$_3$) δ7.80 (bs, 1H), 7.38 (m, 1H), 7.37 (s, 1H), 7.32 (dd, 1H, J=3.0, 8.0 Hz), 2.81 (t, 2H, J=6.5 Hz), 2.64 (t, 2H, J=6.0 Hz), 1.85 (m, 4H); MS (ESI+) m/z 355.1 (M+H) and N-(6-bromo-5-fluoropyridin-2-yl)-4,5,6,7-tetrahydrobenzo[b]thiophene-2-carboxamide in 34% yield as a white solid: $R_f$=0.85 (20% ethyl acetate in hexanes); $^1$H NMR (500 MHz, CDCl$_3$) δ 8.29 (dd, 1H, J=3.5, 9.0 Hz), 8.24 (bs, 1H), 7.47 (dd, 1H, m), 7.33 (s, 1H), 2.81 (t, 2H, J=6.5 Hz), 2.64 (t, 2H, J=6.0 Hz), 1.85 (m, 4H); MS (ESI+) m/z 355.1 (M+H).

3-(4-(4-Ethyl-1-methyl-3-oxopiperazin-2-yl)phenylamino)-1-methyl-5-(4,4,5,5-tetramethyl-1,3,2-dioxaborolan-2-yl)pyrazin-2(1H)-one (39)

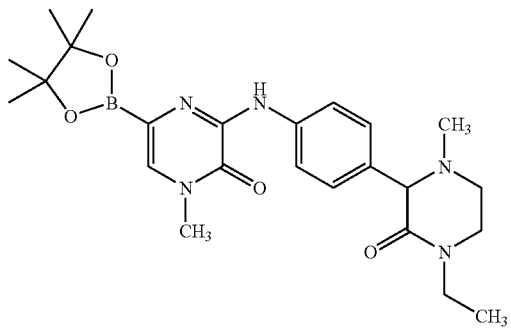

A 25 mL single-neck round-bottomed flask equipped with a magnetic stirrer and thermoregulator was purged with nitrogen and charged with 5-bromo-3-(4-(4-ethyl-1-methyl-3-oxopiperazin-2-yl)phenylamino)-1-methylpyrazin-2(1H)-one (225 mg, 0.536 mmol), bis(4,4,5,5-tetramethylpinacolato)diboron (170 mg, 0.671 mmol) potassium acetate (210 mg, 2.06 mmol) and 1,4-dioxane (10 mL). A stream of nitrogen was passed through the resulting suspension for 30 min. Pd(dppf)Cl$_2$.CH$_2$Cl$_2$ (15 mg, 0.016 mmol) was then added and the reaction stirred at reflux for 3 h. After this time, the mixture was cooled to ambient temperature, partitioned between water (40 mL) and ethyl acetate (60 mL) and filtered through a plug of Celite 521. The organic phase was separated, dried over sodium sulfate, filtered and concentrated under reduced pressure. The residue was triturated with diethyl ether (5 mL) and the suspension was filtered. The filter cake was dried under vacuum at room temperature to afford) crude 39, which was used in the following reaction directly: MS (ESI+) m/z 468.2 (M+H).

N-(6-(6-(4-(4-Ethyl-1-methyl-3-oxopiperazin-2-yl)phenylamino)-4-methyl-5-oxo-4,5-dihydropyrazin-2-yl)-3-fluoropyridin-2-yl)-4,5,6,7-tetrahydrobenzo[b]thiophene-2-carboxamide (40)

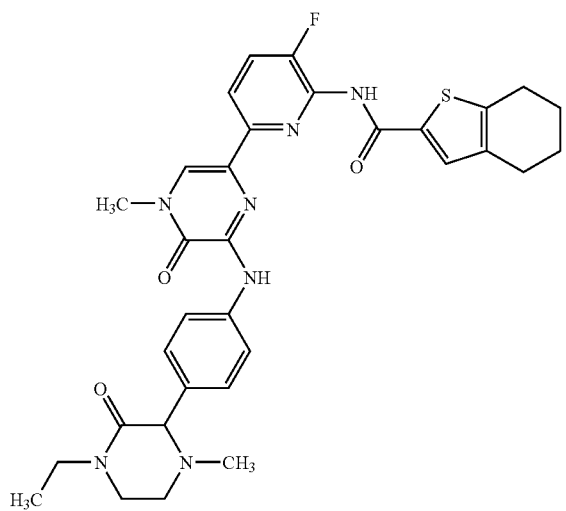

A 25-mL three-neck round-bottomed flask equipped with a magnetic stirrer, reflux condenser and nitrogen inlet was charged with 1,4-dioxane (7 mL), a solution of sodium carbonate (163 mg, 2.08 mmol) in water (1 mL), 38 (183 mg, 0.515 mmol) and 39 (0.537 mmol, presuming quantitative yield) After bubbling nitrogen through the resulting mixture for 30 min, tetrakis(triphenylphosphine)palladium(0) (60 mg, 0.052 mmol) was added, and the reaction mixture then heated at reflux for 4 h. After this time, the reaction mixture was cooled to room temperature, and 2N hydrochloric acid (20 mL) followed by methylene chloride (20 mL) was added. The aqueous layer was separated, washed with methylene chloride (2×25 mL) and then basified to pH 9 with saturated aqueous potassium carbonate. The aqueous layer was then extracted with methylene chloride (3×25 mL), and the organic extracts were combined and dried over sodium sulfate. The drying agent was removed by vacuum filtration and the filtrate concentrated under reduced pressure to afford 40 in 30% yield (83 mg) as a yellow solid: mp 155-156° C.; $^1$H NMR (500 MHz, CDCl$_3$) δ 8.27 (bs, 1H), 7.95 (dd, 1H, J=3.5, 8.5 Hz), 7.84 (m, 3H), 7.72 (s, 1H), 7.55 (t, 1H, J=9.0 Hz), 7.46 (m, 3H), 4.01 (s, 1H), 3.72 (m, 2H), 3.64 (s, 3H), 3.49 (m, 1H), 3.40 (m, 1H), 3.38 (m, 1H), 3.24 (m, 1H), 2.83 (t, 2H, J=6.0 Hz), 2.67 (m, 3H), 1.86 (m, 4H), 1.16 (t, 3H, J=7.5 Hz); MS (ESI+) m/z 616.3 (M+H).

EXAMPLE 8
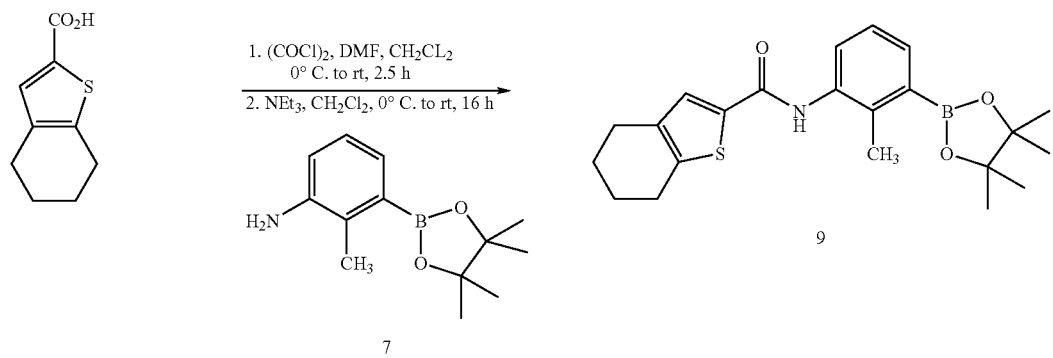
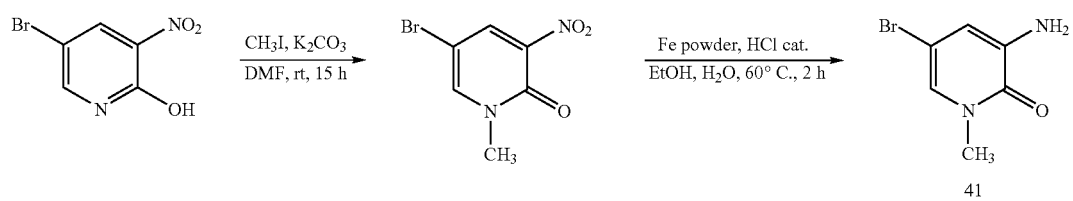
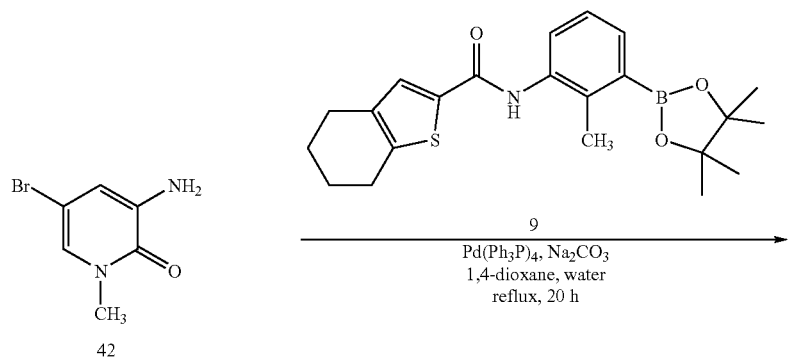
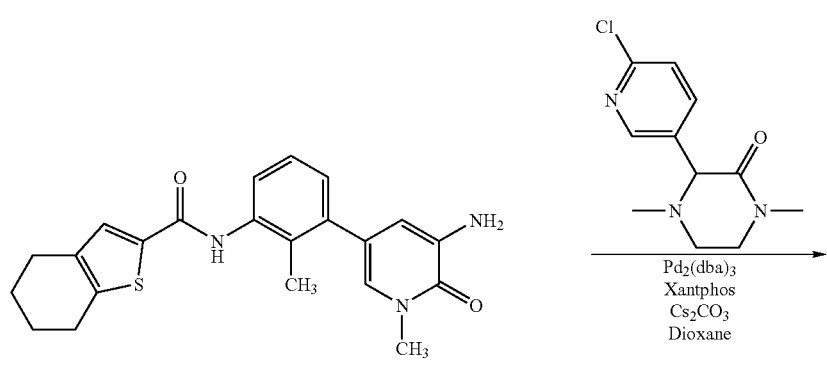

-continued

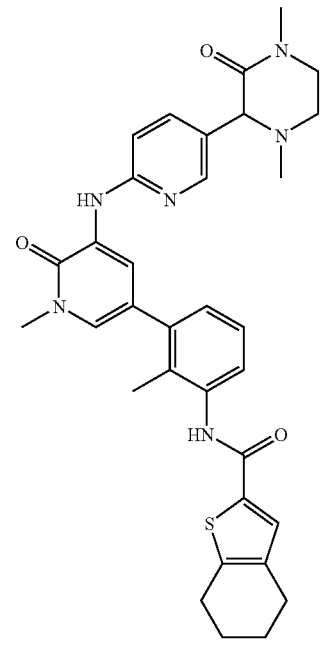

44

5-Bromo-1-methyl-3-nitropyridin-2-one (41)

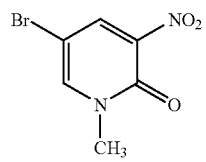

A 1-L round-bottomed flask equipped with a magnetic stirrer was purged with nitrogen and charged with 5-bromo-3-nitro-2-hydroxypyridine (24.0 g, 0.11 mol), anhydrous DMF (280 mL) and powdered potassium carbonate (−350 mesh, 33.4 g, 0.24 mol), and the suspension stirred for 15 min at ambient temperature. After this time methyl iodide (17.1 g, 0.124 mol) was added, and the mixture stirred at room temperature for 18 h. The reaction mixture was then diluted with water (750 mL) and extracted with ethyl acetate (3×1.0 L). The organic extracts were combined, washed with brine (500 mL) and dried over sodium sulfate. After removing the drying agent by filtration, the filtrate was evaporated to dryness under reduced pressure. The resulting residue was purified by flash chromatography on silica to afford an 85% yield (21.7 g) of 41 as a yellow solid: mp 122-123° C.; $^1$H NMR (300 MHz, CDCl$_3$) δ 8.37 (d, 1H, J=2.7 Hz), 7.26 (s, 1H), 3.68 (s, 3H); MS (ESI+) m/z 234 (M+H).

3-Amino-5-bromo-1-methylpyridin-2-one (42)

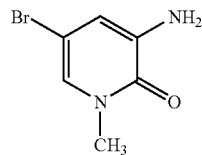

A 1-L three-neck round-bottomed flask equipped with a mechanical stirrer and reflux condenser was purged with nitrogen and charged with 41 (21.7 g, 93.3 mmol), ethanol (305 mL), iron powder (−325 mesh, 52.1 g, 933 mmol) and 2N hydrochloric acid (50 mL, 100 mmol), and the mixture was heated for 2 h at 60° C. After this time, the reaction was cooled to room temperature, and potassium carbonate was added to pH 8 as determined by a pH paper. The resulting suspension was filtered and the filter cake washed with ethanol (4×100 mL). The filtrate was concentrated under reduced pressure to yield a brown solid. This solid was purified by column chromatography on silica gel to afford 42 in 77% yield (14.5 g) as an off-white powder: mp 104-105° C.; $^1$H NMR (500 MHz, DMSO-d$_6$) δ 7.15 (d, 1H, J=2.5 Hz), 6.46 (d, 1H, J=2.5 Hz), 5.45 (bs, 2H), 3.40 (s, 3H); MS (ESI+) m/z 203 (M+H).

N-(3-(5-Amino-1-methyl-6-oxo-1,6-dihydropyridin-3-yl)-2-methylphenyl)-4,5,6,7-tetrahydrobenzo[b]thiophene-2-carboxamide (43)

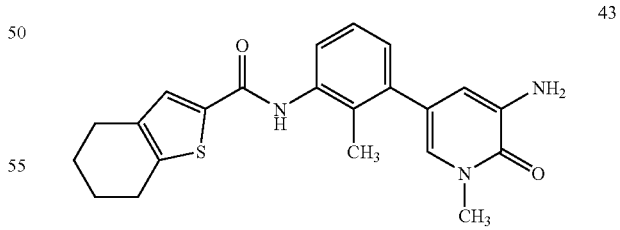

Using the same general procedure as described for the preparation of 10, 42 (3.67 g) gave a 28% yield (2.10 g) of 43 as a yellow solid: mp 210-211° C.; $^1$H NMR (500 MHz, DMSO-d$_6$) δ 9.78 (bs, 1H), 7.65 (s, 1H), 7.25 (dd, 1H, J=1.5, 8.0 Hz), 7.21 (t, 1H, J=7.5 Hz), 7.09 (dd, 1H, J=1.0, 7.0 Hz), 6.89 (d, 1H, J=2.0 Hz), 6.43 (d, 1H, J=2.5 Hz), 5.19 (bs, 2H), 3.49 (s, 3H), 2.75 (m, 2H), 2.62 (m, 2H), 2.12 (s, 3H), 1.77 (m, 4H); MS (ESI+) m/z 394 (M+H).

77

N-[3-(5-{[5-(1,4-dimethyl-3-oxopiperazin-2-yl)pyridin-2-yl]amino}-1-methyl-6-oxo-1,6-dihydropyridin-3-yl)-2-methylphenyl]-4,5,6,7-tetrahydro-1-benzothiophene-2-carboxamide (44)

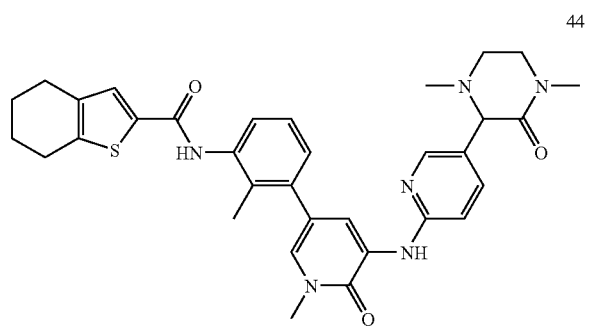

A 48-mL sealed tube equipped with a magnetic stirring bar was charged with 43 (0.20 g, 0.5 mmol), 3-(6-chloropyridin-3-yl)-1,4-dimethylpiperazin-2-one (0.185 g, 0.8 mmol), $Pd_2(dba)_3$ (0.032 g, 0.035 mmol), 9,9-dimethyl-4,5-bis(diphenylphosphino)xanthene (0.030 g, 0.05 mmol), and $Cs_2CO_3$ (0.326 g, 1.0 mmol) in dioxane (10 mL). After the mixture was degassed for 15 min., it was heated at 95° C. for 16 h. Then, the reaction mixture was cooled to room temperature and poured into $H_2O$ (10 mL). To this was added dichloromethane (10 mL) and the layers were separated. The aqueous phase was extracted with dichloromethane (3×10 mL), and the combined organic extracts were washed with $H_2O$ (5 mL) and brine (5 mL), dried ($Na_2SO_4$), and concentrated. The crude mixture was purified by column chromatography, gradient 0-10%, MeOH in dichloromethane/ether (1/1), to afford 0.10 g (34%) of 44 as a solid; MS (ESI+) m/z 596 (M+H).

EXAMPLE 9

Scheme 9

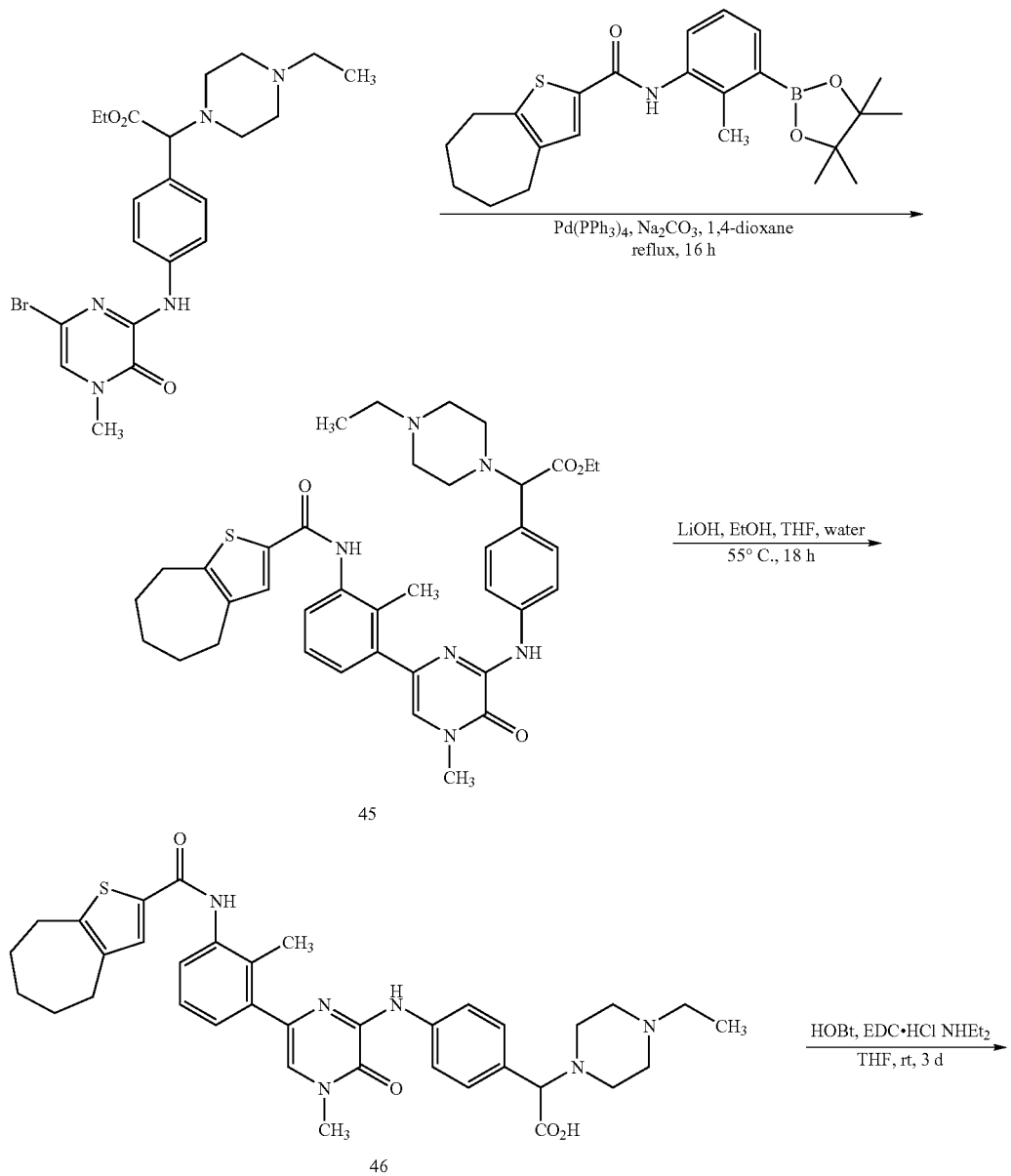

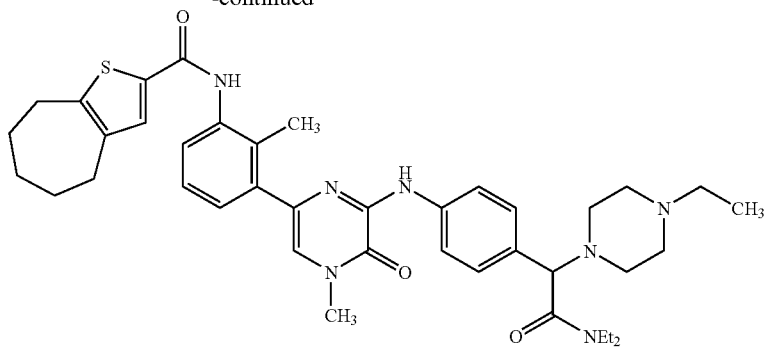

47

Ethyl 2-(4-Ethylpiperazin-1-yl)-2-(4-(4-methyl-6-(2-methyl-3-(5,6,7,8-tetrahydro-4H-cyclohepta[b]thiophene-2-carboxamido)phenyl)-3-oxo-3,4-dihydropyrazin-2-ylamino)phenyl)acetate (45)

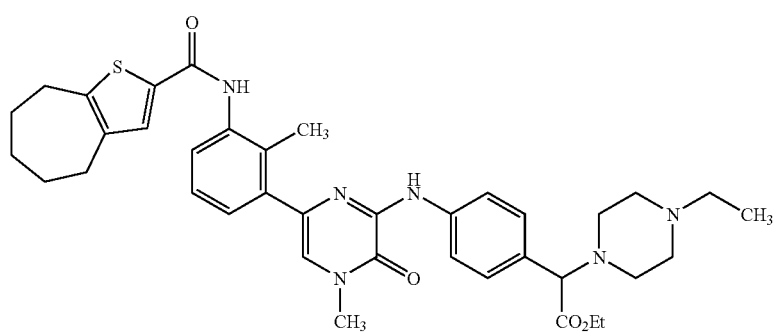

45

Using the same procedure as described for the preparation of 10, the reaction of ethyl 2-(4-(6-Bromo-4-methyl-3-oxo-3,4-dihydropyrazin-2-ylamino)phenyl)-2-(4-ethylpiperazin-1-yl)acetate (1.33 g) with N-(2-methyl-3-(4,4,5,5-tetramethyl-1,3-dioxolan-2-yl)phenyl)-5,6,7,8-tetrahydro-4H-cyclohepta[b]thiophene-2-carboxamide (1.26 g) gave a 73% yield (1.39 g) of 45 as a tan foam: mp 168-170° C.; $^1$H NMR (300 MHz, CDCl$_3$) δ 8.34 (s, 1H), 7.92 (d, 1H, J=7.8 Hz), 7.80 (d, 2H, J=8.7 Hz), 7.54 (s, 1H), 7.39 (d, 2H, J=8.7 Hz), 7.39 (s, 1H), 7.27 (t, 1H, J=8.1 Hz), 7.18 (dd, 1H, J=7.8, 1.2 Hz), 6.74 (s, 1H), 4.14 (m, 2H), 3.91 (s, 1H), 3.60 (s, 3H), 2.87 (t, 2H, J=5.7 Hz), 2.76 (t, 2H, J=5.7 Hz), 2.61 (br s, 8H), 2.32 (s, 3H), 1.88 (m, 2H), 1.77 (m, 4H), 1.17 (t, 3H, J=7.2 Hz), 1.05 (t, 3H, J=7.2 Hz); MS (ESI+) m/z 683 (M+H).

2-(4-Ethylpiperazin-1-yl)-2-(4-(4-methyl-6-(2-methyl-3-(5,6,7,8-tetrahydro-4H-cyclohepta[b]thiophene-2-carboxamido)phenyl)-3-oxo-3,4-dihydropyrazin-2-ylamino)phenyl)acetic Acid (46)

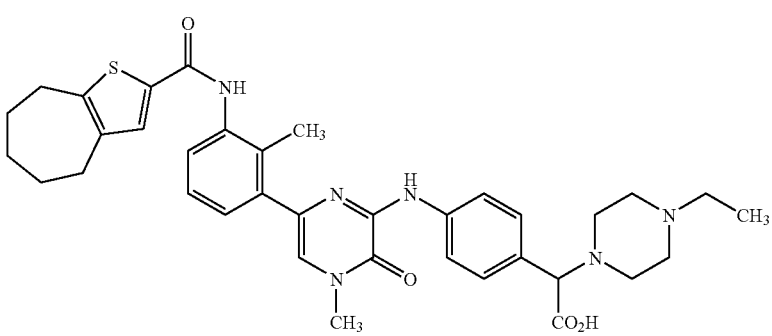

46

Using the same procedure as described for the preparation of 29, saponification of 45 (1.29 g) gave a 97% yield (1.20 g) of 46 as an off-white solid: mp 168-170° C.; $^1$H NMR (300 MHz, DMSO-d$_6$) δ 9.79 (s, 1H), 9.25 (s, 1H), 7.96 (d, 2H, J=7.5 Hz), 7.70 (s, 1H), 7.29 (m, 6H), 3.86 (m, 1H), 3.71 (s, 3H), 3.37 (q, 2H, J=7.2 Hz), 2.81 (m, 2H), 2.69 (m, 2H), 2.42 (br s, 8H), 2.19 (s, 3H), 1.83 (br s, 2H), 1.61 (br s, 4H), 0.95 (t, 3H, J=7.2 Hz); MS (ESI+) m/z 655 (M+H).

N-(3-(6-(4-(1-(4-Ethylpiperazin-1-yl)-2-((2-hydroxyethyl)(methyl)amino)-2-oxoethyl)phenylamino)-4-methyl-5-oxo-4,5-dihydropyrazin-2-yl)-2-methylphenyl)-5,6,7,8-tetrahydro-4H-cyclohepta[b]thiophene-2-carboxamide (47)

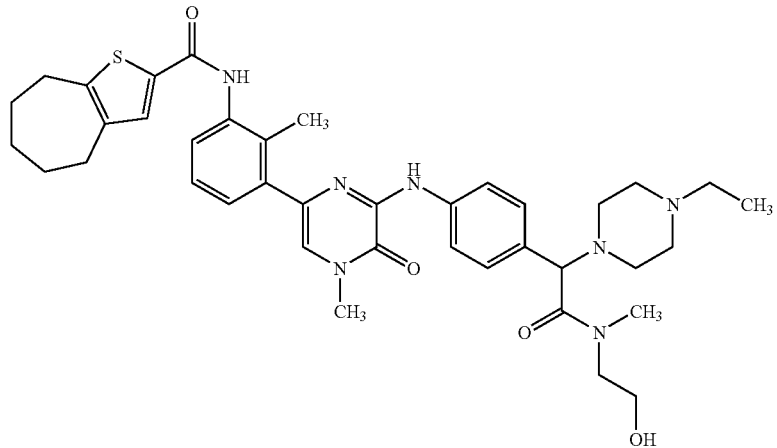

Using the same procedure as described for the preparation of 30, the reaction of 46 (307 mg) with 2-(methylamino)ethanol (71 mg) gave a 37% yield (125 mg) of 47 as a white solid: mp 163-165° C.; $^1$H NMR (500 MHz, CDCl$_3$) δ 8.33 (s, 1H), 7.90 (d, 1H, J=8.0 Hz), 7.80 (d, 2H, J=9.0 Hz), 7.62 (s, 1H), 7.48 (m, 1H), 7.41 (s, 1H), 7.35 (d, 2H, J=8.5 Hz), 7.27 (t, 1H, J=8.0 Hz), 7.17 (d, 1H, J=7.5 Hz), 6.74 (s, 1H), 4.15 (s, 1H), 3.72 (m, 2H), 3.62 (m, 1H), 3.61 (s, 3H), 3.50 (m, 2H), 3.02 (s, 3H), 2.87 (t, 2H, J=5.5 Hz), 2.75 (t, 2H, J=5.5 Hz), 2.56 (m, 8H), 2.40 (s, 3H), 1.88 (m, 2H), 1.74 (m, 2H), 1.65 (m, 2H), 1.09 (t, 3H, J=7.0 Hz); MS (ESI+) m/z 712 (M+H).

EXAMPLE 10

The following compounds were prepared using procedures similar to those described in Examples 1-9.

| Structure | Name | MW calc | MH+ m/z obs |
|---|---|---|---|
| 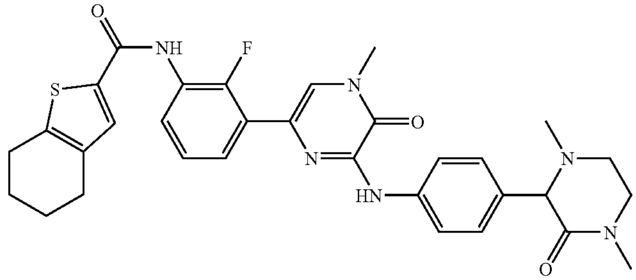 | N-(3-(6-(4-(1,4-dimethyl-3-oxopiperazin-2-yl)phenylamino)-4-methyl-5-oxo-4,5-dihydropyrazin-2-yl)-2-fluorophenyl)-4,5,6,7-tetrahydrobenzo[b]thiophene-2-carboxamide | 600.23 | 601.3 |

-continued

| Structure | Name | MW calc | MH+ m/z obs |
|---|---|---|---|
| 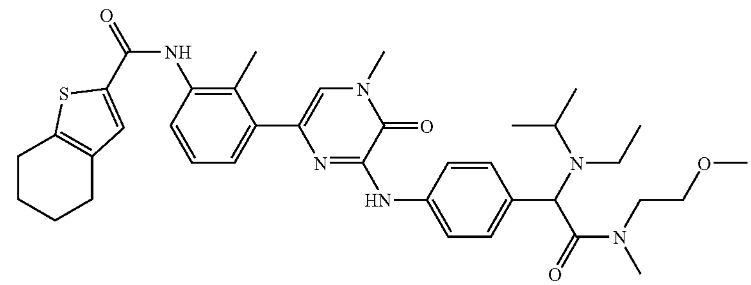 | N-(3-(6-(4-(1-(ethyl(isopropyl)amino)-2-((2-methoxyethyl)(methyl)amino)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide | 684.35 | 685.0 |
| 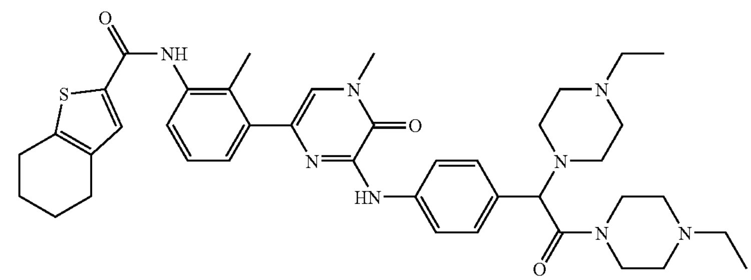 | N-(3-(6-(4-(1,2-bis(4-ethylpiperazin-1-yl)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide | 736.39 | 737.4 |
| 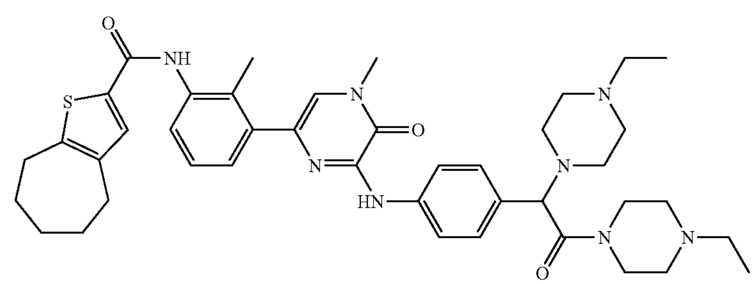 | N-(3-(6-(4-(1,2-bis(4-ethylpiperazin-1-yl)-2-oxoethyl)phenylamino)-4-methyl-5-oxo-4,5-dihydropyrazin-2-yl)-2-methylphenyl)-5,6,7,8-tetrahydro-4H-cyclohepta[b]thiophene-2-carboxamide | 750.40 | 751.4 |
| 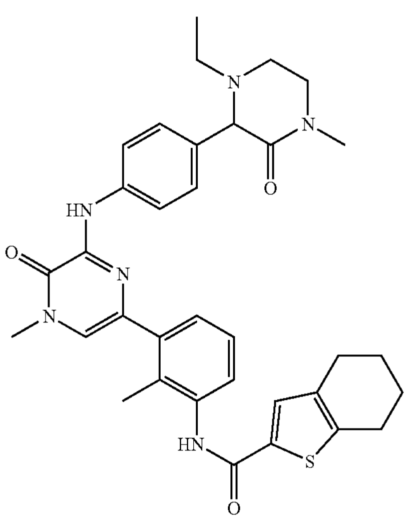 | N-(3-(6-(4-(1-ethyl-4-methyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide | 610.27 | 611.5 |

-continued

| Structure | Name | MW calc | MH+ m/z obs |
|---|---|---|---|
| 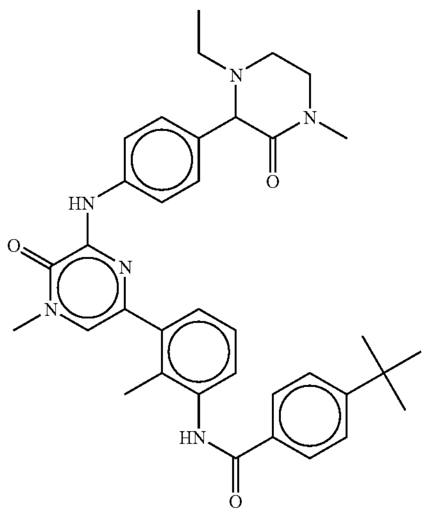 | 4-tert-butyl-N-(3-(6-(4-(1-ethyl-4-methyl-3-oxo piperazin-2-yl)phenylamino)-4-methyl-5-oxo-4,5-dihydro pyrazin-2-yl)-2-methylphenyl) benzamide | 606.33 | 607.3 |
| 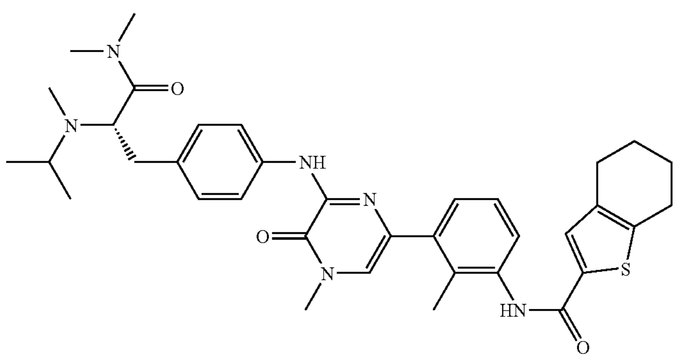 | (S)-N-(3-(6-(4-(3-(dimethyl amino)-2-(isopropyl (methyl)amino)-3-oxopropyl) phenylamino)-4-methyl-5-oxo-4,5-dihydropyrazin-2-yl)-2-methylphenyl)-4,5,6,7-tetrahydrobenzo[b]thiophene-2-carboxamide | 640.32 | 641.6 |
| 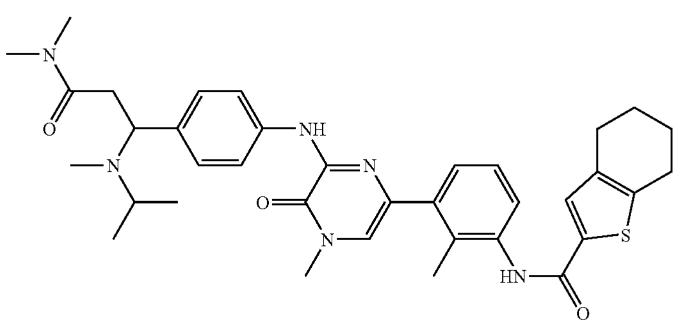 | N-(3-(6-(4-(3-(dimethylamino)-1-(isopropyl(methyl)amino)-3-oxopropyl)phenylamino)-4-methyl-5-oxo-4,5-dihydro pyrazin-2-yl)-2-methyl phenyl)-4,5,6,7-tetrahydro benzo[b]thiophene-2-carboxamide | 640.32 | 641.6 |
| 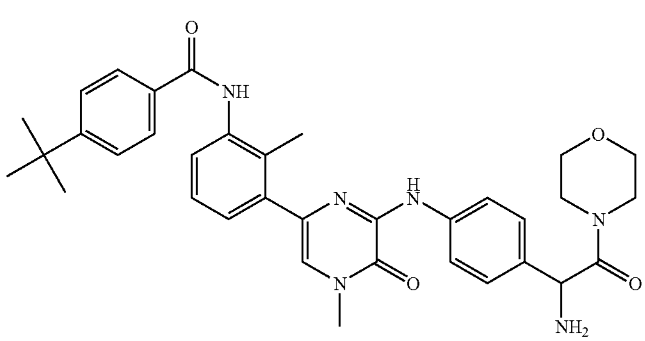 | N-(3-(6-(4-(1-amino-2-morpholino-2-oxoethyl)phenylamino)-4-methyl-5-oxo-4,5-dihydropyrazin-2-yl)-2-methylphenyl)-4-tert-butylbenzamide | 608.31 | 609.25 |

-continued

| Structure | Name | MW calc | MH+ m/z obs |
|---|---|---|---|
| 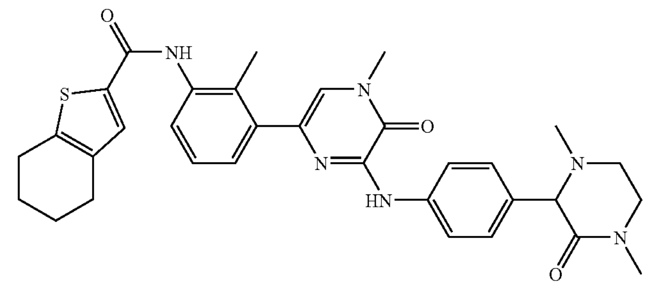 | N-(3-(6-(4-(1,4-dimethyl-3-oxopiperazin-2-yl)phenyl amino)-4-methyl-5-oxo-4,5-dihydropyrazin-2-yl)-2-methylphenyl)-4,5,6,7-tetra hydrobenzo[b]thiophene-2-carboxamide | 596.26 | 597.2 |
| 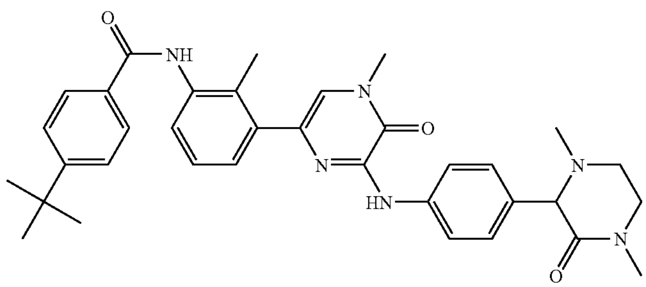 | 4-tert-butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide | 592.32 | 593.3 |
| 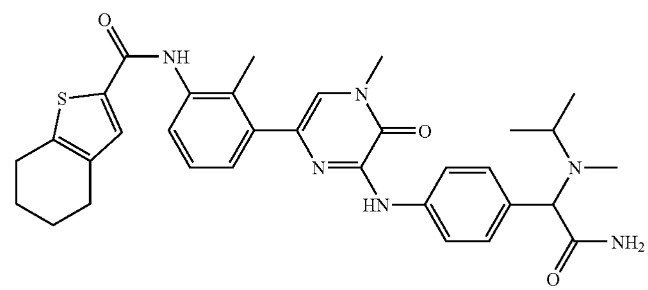 | N-(3-(6-(4-(2-amino-1-(isopropyl(methyl)amino)-2-oxoethyl)phenylamino)-4-methyl-5-oxo-4,5-dihydro pyrazin-2-yl)-2-methylphenyl)-4,5,6,7-tetrahydrobenzo[b]thiophene-2-carboxamide | 598.27 | 599.3 |
| 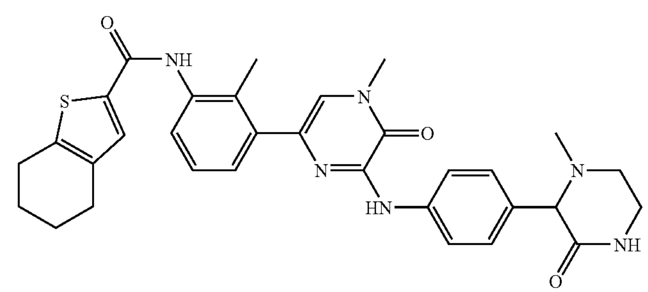 | N-(2-methyl-3-(4-methyl-6-(4-(1-methyl-3-oxopiperazin-2-yl)phenylamino)-5-oxo-4,5-dihydropyrazin-2-yl)phenyl)-4,5,6,7-tetrahydrobenzo[b]thiophene-2-carboxamide | 582.24 | 583.3 |
| | N-(3-(6-(4-(2-(dimethylamino)-1-(isopropyl(methyl)amino)-2-oxoethyl)phenylamino)-4-methyl-5-oxo-4,5-dihydro pyrazin-2-yl)-2-methylphenyl)-4,5,6,7-tetrahydrobenzo[b]thiophene-2-carboxamide | 626.3 | 627.1 |

-continued

| Structure | Name | MW calc | MH+ m/z obs |
|---|---|---|---|
| 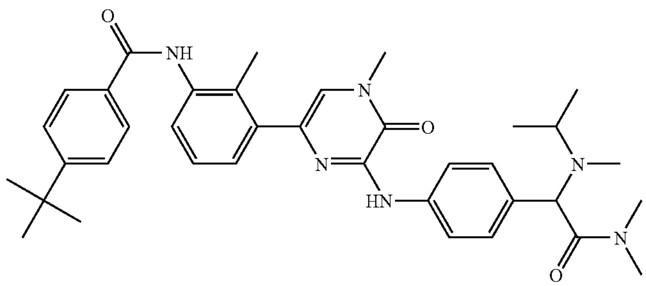 | 4-tert-butyl-N-(3-(6-(4-(2-(dimethylamino)-1-(isopropyl(methyl)amino)-2-oxoethyl)phenylamino)-4-methyl-5-oxo-4,5-dihydropyrazin-2-yl)-2-methylphenyl)benzamide | 622.36 | 623.21 |
| 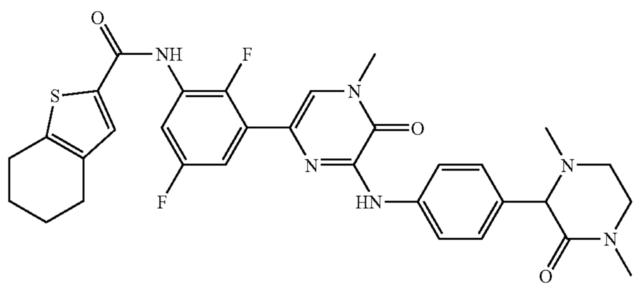 | N-(3-(6-(4-(1,4-dimethyl-3-oxopiperazin-2-yl)phenyl amino)-4-methyl-5-oxo-4,5-dihydropyrazin-2-yl)-2,5-difluorophenyl)-4,5,6,7-tetrahydrobenzo[b]thiophene-2-carboxamide | 618.22 | 619.4 |
| 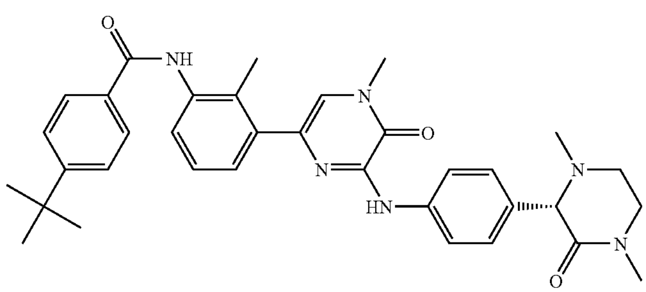 | (S)-4-tert-butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide | 592.32 | 593.3 |
| 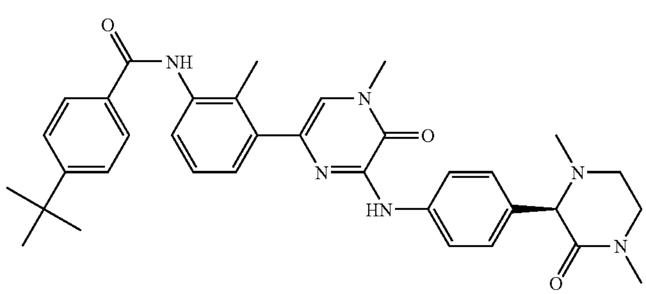 | (R)-4-tert-butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide | 592.32 | 593.3 |
| 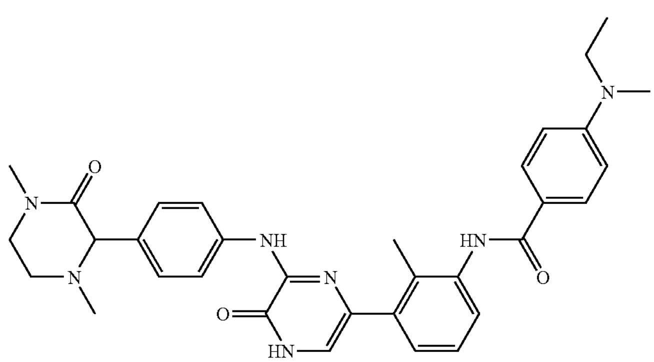 | N-(3-(6-(4-(1,4-dimethyl-3-oxopiperazin-2-yl)phenyl amino)-5-oxo-4,5-dihydro pyrazin-2-yl)-2-methylphenyl)-4-(ethyl(methyl)amino)benzamide | 579.30 | 580.2 |

-continued

| Structure | Name | MW calc | MH+ m/z obs |
|---|---|---|---|
| 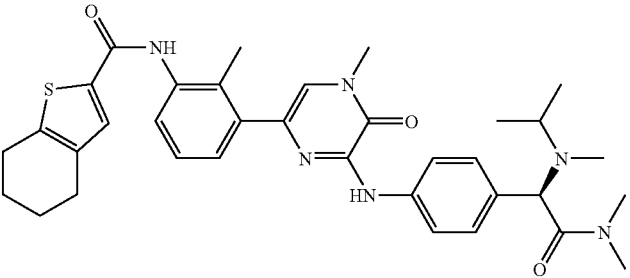 | (R)-N-(3-(6-(4-(2-(dimethyl amino)-1-(isopropyl(methyl) amino-2-oxoethyl)phenyl amino)-4-methyl-5-oxo-4,5-dihydropyrazin-2-yl)-2-methylphenyl)-4,5,6,7-tetrahydrobenzo[b]thiophene-2-carboxamide | 626.30 | 627.5 |
| 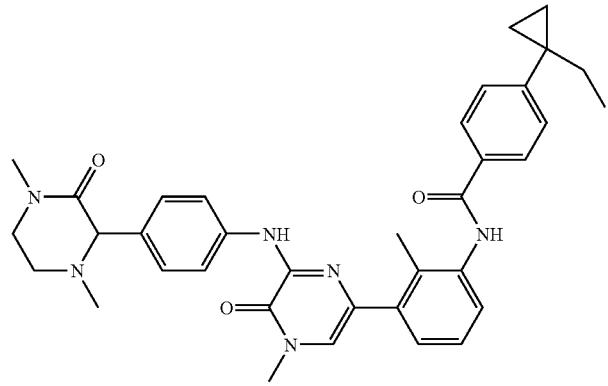 | N-(3-(6-(4-(1,4-dimethyl-3-oxopiperazin-2-yl)phenyl amino)-4-methyl-5-oxo-4,5-dihydropyrazin-2-yl)-2-methylphenyl)-4-(1-ethyl cyclopropyl)benzamide | 604.32 | 605.3 |
| 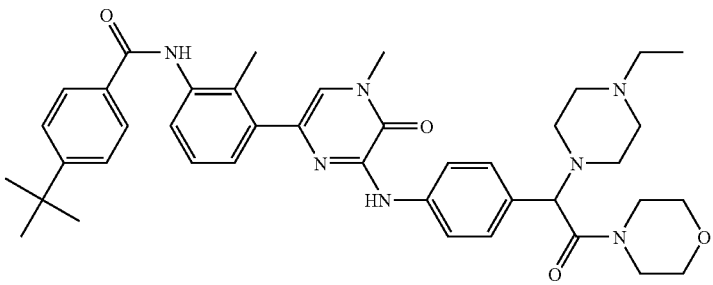 | 4-tert-butyl-N-(3-(6-(4-(1-(4-ethylpiperazin-1-yl)-2-morpholino-2-oxoethyl) phenylamino)-4-methyl-5-oxo-4,5-dihydropyrazin-2-yl)-2-methylphenyl)benzamide | 705.40 | 706.3 |
| 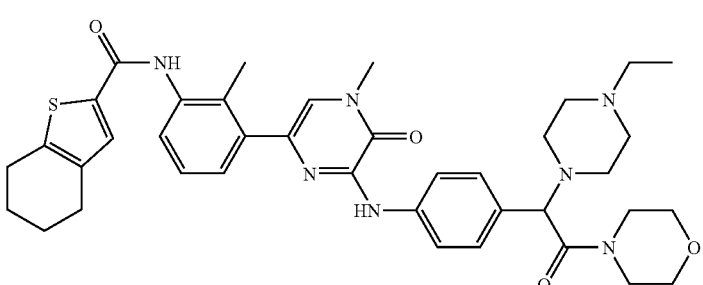 | N-(3-(6-(4-(1-(4-ethyl piperazin-1-yl)-2-morpholino-2-oxoethyl)phenylamino)-4-methyl-5-oxo-4,5-dihydro pyrazin-2-yl)-2-methylphenyl)-4,5,6,7-tetrahydrobenzo[b] thiophene-2-carboxamide | 709.34 | 710.3 |
| 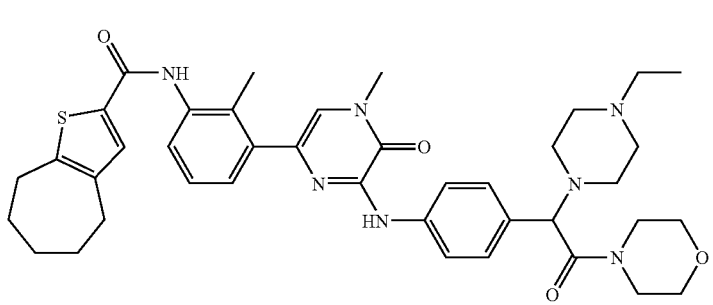 | N-(3-(6-(4-(1-(4-ethyl piperazin-1-yl)-2-morpholino-2-oxoethyl)phenylamino)-4-methyl-5-oxo-4,5-dihydro pyrazin-2-yl)-2-methyl phenyl)-5,6,7,8-tetrahydro-4H-cyclohepta[b]thiophene-2-carboxamide | 732.36 | 724.3 |

-continued

| Structure | Name | MW calc | MH+ m/z obs |
|---|---|---|---|
| 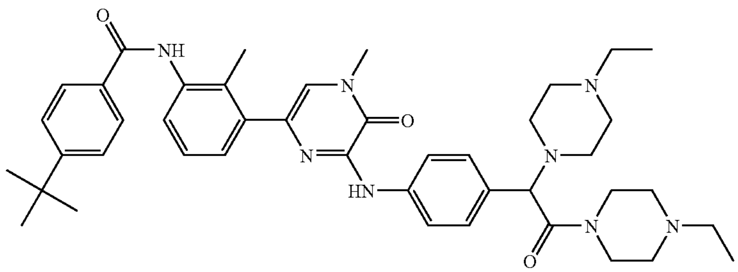 | N-(3-(6-(4-(1,2-bis(4-ethyl piperazin-1-yl)-2-oxoethyl) phenylamino)-4-methyl-5-oxo-4,5-dihydropyrazin-2-yl)-2-methylphenyl)-4-tert-butylbenzamide | 732.45 | 733.5 |
| 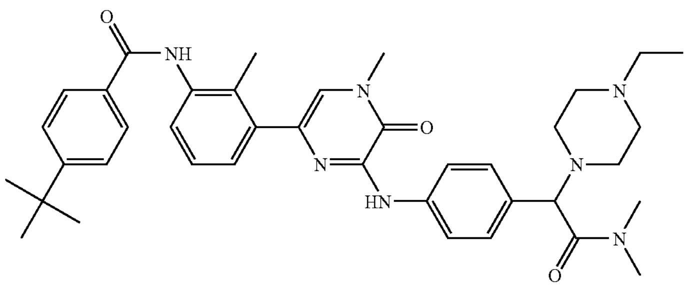 | 4-tert-butyl-N-(3-(6-(4-(2-(dimethylamino)-1-(4-ethylpiperazin-1-yl)-2-oxoethyl)phenylamino)-4-methyl-5-oxo-4,5-dihydropyrazin-2-yl)-2-methylphenyl)benzamide | 663.39 | 664.4 |
| 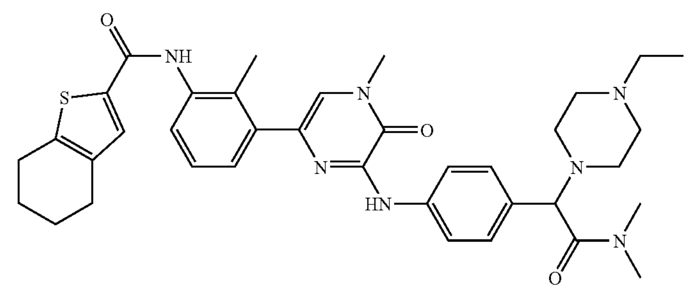 | N-(3-(6-(4-(2-(dimethyl amino)-1-(4-ethylpiperazin-1-yl)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide | 667.33 | 668.4 |
| 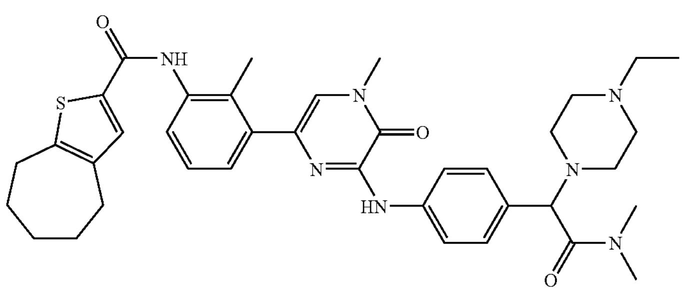 | N-(3-(6-(4-(2-(dimethyl amino)-1-(4-ethylpiperazin-1-yl)-2-oxoethyl)phenylamino)-4-methyl-5-oxo-4,5-dihydro pyrazin-2-yl)-2-methyl phenyl)-5,6,7,8-tetrahydro-4H-cyclohepta[b]thiophene-2-carboxamide | 681.35 | 682.4 |
| 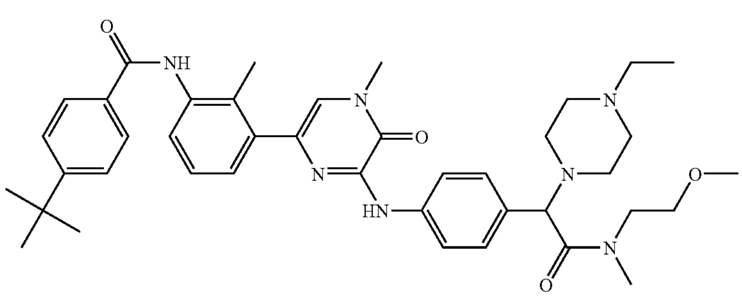 | 4-tert-butyl-N-(3-(6-(4-(1-(4-ethylpiperazin-1-yl)-2-((2-methoxyethyl)(methyl)amino)-2-oxoethyl)phenylamino)-4-methyl-5-oxo-4,5-dihydro pyrazin-2-yl)-2-methylphenyl) benzamide | 707.42 | 708.4 |

-continued

| Structure | Name | MW calc | MH+ m/z obs |
|---|---|---|---|
| 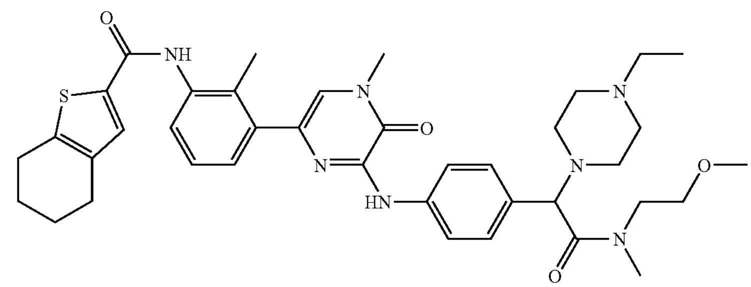 | N-(3-(6-(4-(1-(4-ethyl piperazin-1-yl)-2-((2-methoxyethyl)(methyl)amino)-2-oxoethyl)phenylamino)-4-methyl-5-oxo-4,5-dihydro pyrazin-2-yl)-2-methyl phenyl)-4,5,6,7-tetrahydro benzo[b]thiophene-2-carboxamide | 711.36 | 712.3 |
| 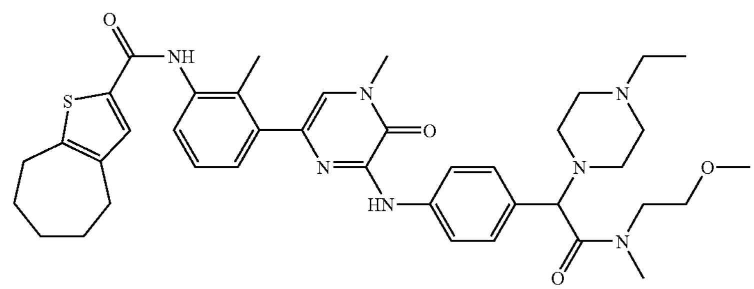 | N-(3-(6-(4-(1-(4-ethyl piperazin-1-yl)-2-((2-methoxy ethyl)(methyl)amino)-2-oxoethyl)phenylamino)-4-methyl-5-oxo-4,5-dihydro pyrazin-2-yl)-2-methylphenyl)-5,6,7,8-tetrahydro-4H-cyclohepta[b]thiophene-2-carboxamide | 725.37 | 726.3 |
| 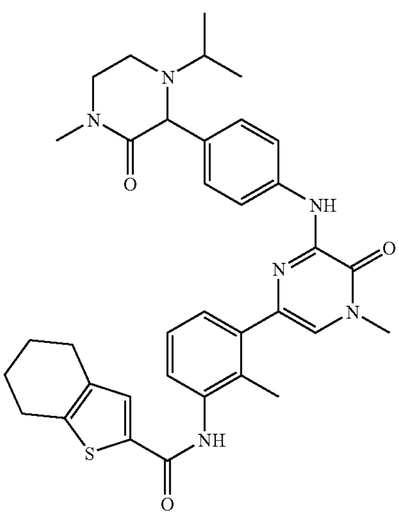 | N-(3-(6-(4-(1-isopropyl-4-methyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide | 624.29 | 625.5 |
| 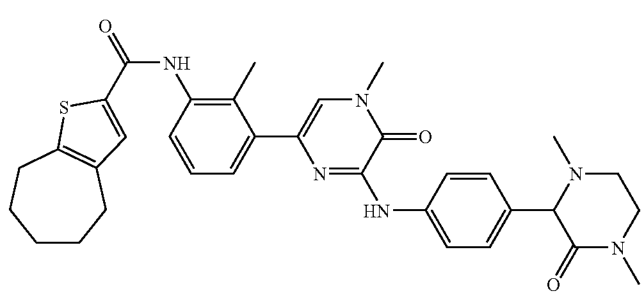 | N-(3-(6-(4-(1,4-dimethyl-3-oxopiperazin-2-yl)phenyl-amino)-4-methyl-5-oxo-4,5-dihydropyrazin-2-yl)-2-methylphenyl)-5,6,7,8-tetrahydro-4H-cyclohepta[b]thiophene-2-carboxamide | 610.27 | 610.9 |

-continued

| Structure | Name | MW calc | MH+ m/z obs |
|---|---|---|---|
| 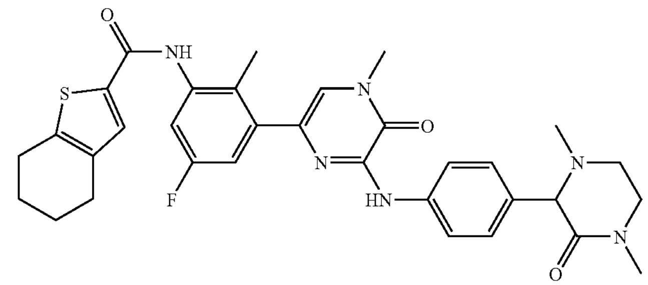 | N-(3-(6-(4-(1,4-dimethyl-3-oxopiperazin-2-yl)phenyl-amino)-4-methyl-5-oxo-4,5-dihydropyrazin-2-yl)-5-fluoro-2-methylphenyl)-4,5,6,7-tetrahydrobenzo[b]thiophene-2-carboxamide | 614.25 | 614.9 |
| 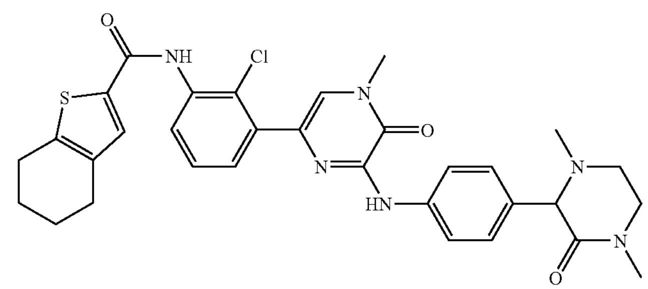 | N-(2-chloro-3-(6-(4-(1,4-dimethyl-3-oxopiperazin-2-yl)phenylamino)-4-methyl-5-oxo-4,5-dihydropyrazin-2-yl)phenyl)-4,5,6,7-tetrahydrobenzo[b]thiophene-2-carboxamide | 616.20 | 616.9 |
| 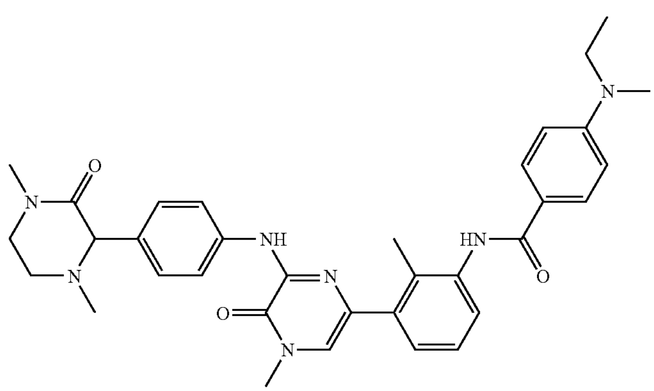 | N-(3-(6-(4-(1,4-dimethyl-3-oxopiperazin-2-yl)phenyl-amino)-4-methyl-5-oxo-4,5-dihydropyrazin-2-yl)-2-methylphenyl)-4-(ethyl(methyl)amino)benzamide | 593.31 | 594.0 |
| 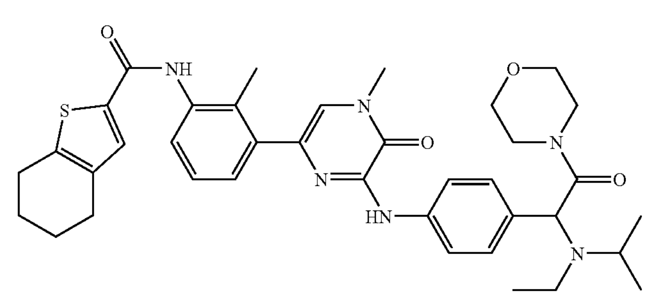 | N-(3-(6-(4-(1-(ethyl(isopropyl)amino)-2-morpholino-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide | 682.33 | 683.3 |

-continued

| Structure | Name | MW calc | MH+ m/z obs |
|---|---|---|---|
| 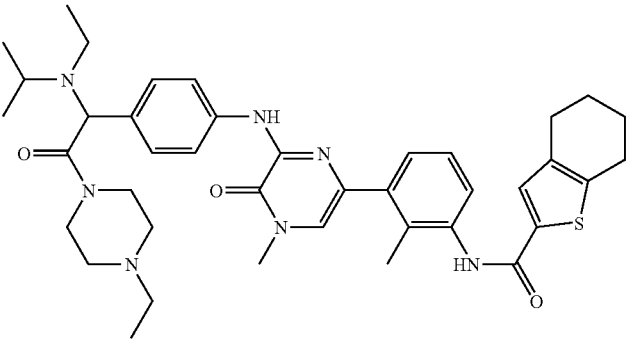 | N-(3-(6-(4-(1-(ethyl(isopropyl) amino)-2-(4-ethylpiperazin-1-yl)-2-oxoethyl)phenylamino)-4-methyl-5-oxo-4,5-dihydro pyrazin-2-yl)-2-methyl phenyl)-4,5,6,7-tetrahydro benzo[b]thiophene-2-carboxamide | 709.38 | 711.5 |
| 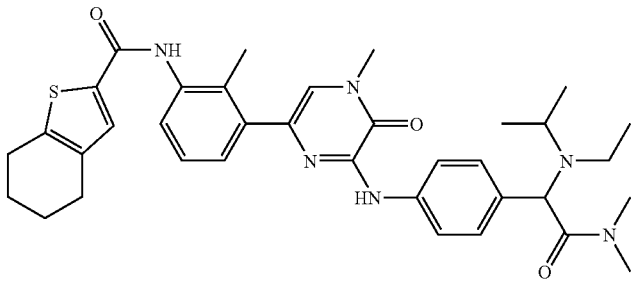 | N-(3-(6-(4-(2-(dimethyl amino)-1-(ethyl(isopropyl) amino)-2-oxoethyl)phenyl-mino)-4-methyl-5-oxo-4,5-dihydropyrazin-2-yl)-2-methylphenyl)-4,5,6,7-tetrahydrobenzo[b]thiophene-2-carboxamide | 640.32 | 641.3 |
| 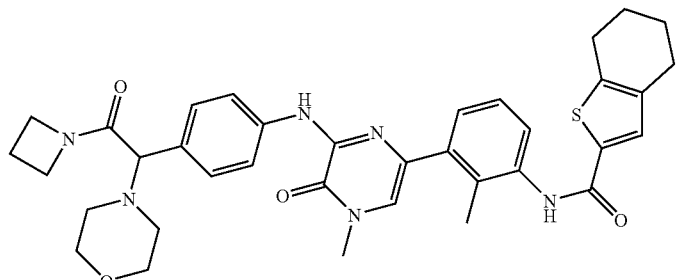 | N-{3-[6-({4-[2-(azetidin-1-yl)-1-(morpholin-4-yl)-2-oxo-ethyl]phenyl}amino)-4-methyl-5-oxo-4,5-dihydro pyrazin-2-yl]-2-methyl phenyl}-4,5,6,7-tetrahydro-1-benzothiophene-2-carboxamide | 652.28 | 653.2 |
| 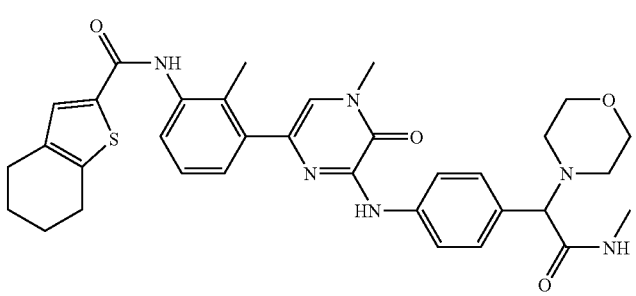 | N-{2-methyl-3-[4-methyl-6-({4-[(methylcarbamoyl) (morpholin-4-yl)methyl] phenyl}amino)-5-oxo-4,5-dihydropyrazin-2-yl]phenyl}-4,5,6,7-tetrahydro-1-benzothiophene-2-carboxamide | 626.27 | 627.2 |
| 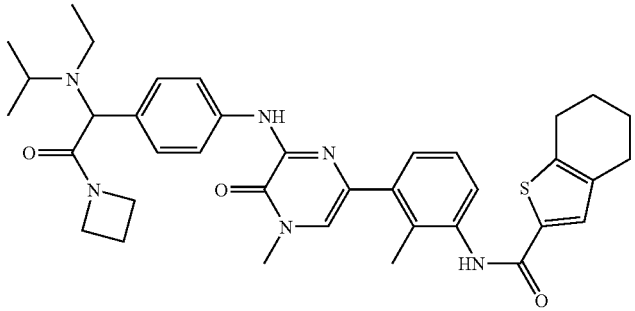 | N-{3-[6-({4-[2-(azetidin-1-yl)-1-[ethyl(propan-2-yl)amino]-2-oxoethyl]phenyl}amino)-4-methyl-5-oxo-4,5-dihydro pyrazin-2-yl]-2-methylphenyl}-4,5,6,7-tetrahydro-1-benzothiophene-2-carboxamide | 652.32 | 653.2 |

-continued

| Structure | Name | MW calc | MH+ m/z obs |
|---|---|---|---|
| 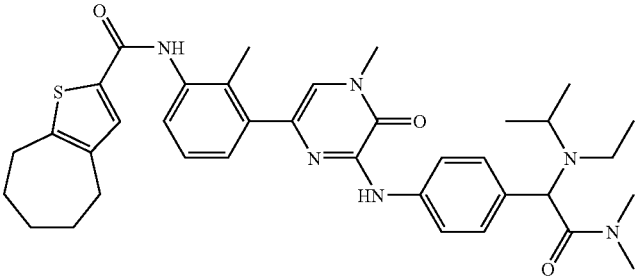 | N-{3-[6-({4-[(dimethyl carbamoyl)[ethyl(propan-2-yl)amino]methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide | 654.86 | 655.6 |
| 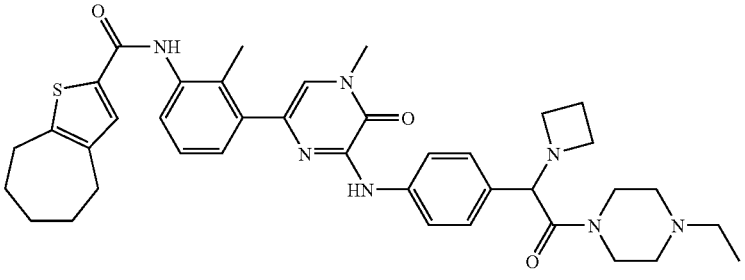 | N-{3-[6-({4-[1-(azetidin-1-yl)-2-(4-ethylpiperazin-1-yl)-2-oxoethyl]phenyl}amino)-4-methyl-5-oxo-4,5-dihydro pyrazin-2-yl]-2-methyl phenyl}-4H,5H,6H,7H,8H-cyclohepta[b]thiophene-2-carboxamide | 693.35 | 694.3 |
| 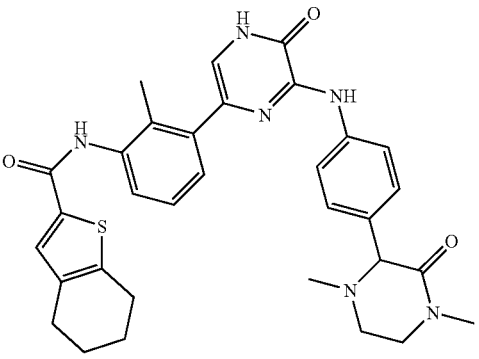 | N-[3-(6-{[4-(1,4-dimethyl-3-oxopiperazin-2-yl)phenyl]amino}-5-oxo-4,5-dihydropyrazin-2-yl)-2-methylphenyl]-4,5,6,7-tetrahydro-1-benzothiophene-2-carboxamide | 582.24 | 583.0 |
| 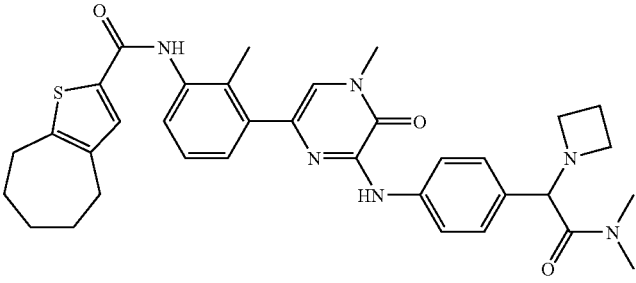 | N-{3-[6-({4-[azetidin-1-yl(dimethylcarbamoyl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide | 624.29 | 625.4 |

-continued

| Structure | Name | MW calc | MH+ m/z obs |
|---|---|---|---|
| 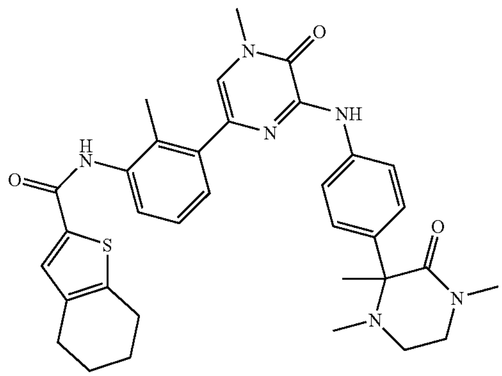 | N-[2-methyl-3-(4-methyl-5-oxo-6-{[4-(1,2,4-trimethyl-3-oxopiperazin-2-yl)phenyl]amino}-4,5-dihydropyrazin-2-yl)phenyl]-4,5,6,7-tetrahydro-1-benzothiophene-2-carboxamide | 610.27 | 611.3 |
| 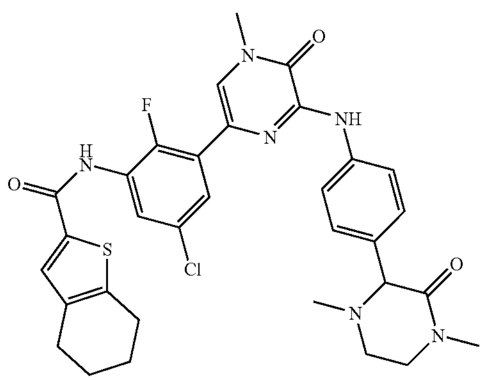 | N-[5-chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 634.19 | 635.6 |
| 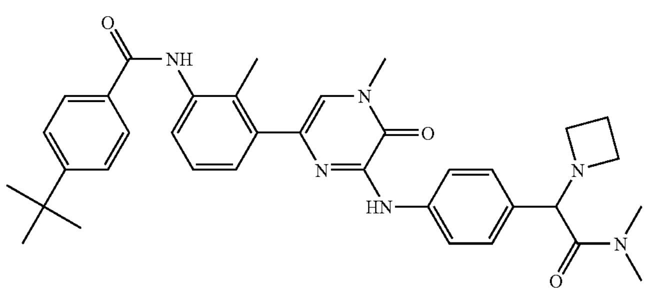 | N-{3-[6-({4-[azetidin-1-yl(dimethylcarbamoyl)methyl]phenyl}amino)-4-methyl-5-oxo-4,5-dihydropyrazin-2-yl]-2-methylphenyl}-4-tert-butylbenzamide | 606.33 | 607.6 |
| 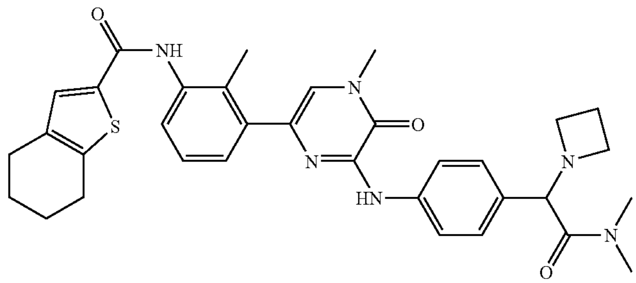 | N-{3-[6-({4-[azetidin-1-yl(dimethylcarbamoyl)methyl]phenyl}amino)-4-methyl-5-oxo-4,5-dihydropyrazin-2-yl]-2-methylphenyl}-4,5,6,7-tetrahydro-1-benzothiophene-2-carboxamide | 610.27 | 611.5 |

-continued

| Structure | Name | MW calc | MH+ m/z obs |
|---|---|---|---|
| 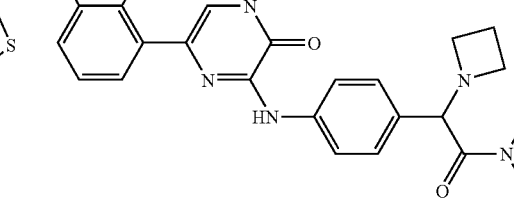 | N-(3-{6-[(4-{azetidin-1-yl[(2-hydroxyethyl)(methyl)carbamoyl]methyl}phenyl)amino]-4-methyl-5-oxo-4,5-dihydropyrazin-2-yl}-2-methylphenyl)-4,5,6,7-tetrahydro-1-benzothiophene-2-carboxamide | 640.28 | 641.6 |
| 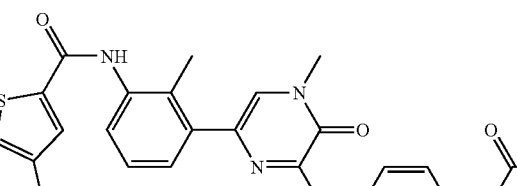 | N-{2-methyl-3-[4-methyl-6-({4-[4-methyl-3-oxo-1-(propan-2-yl)piperazin-2-yl]phenyl}amino)-5-oxo-4,5-dihydropyrazin-2-yl]phenyl}-4H,5H,6H,7H,8H-cyclohepta[b]thiophene-2-carboxamide | 638.3 | 639.7 |
| 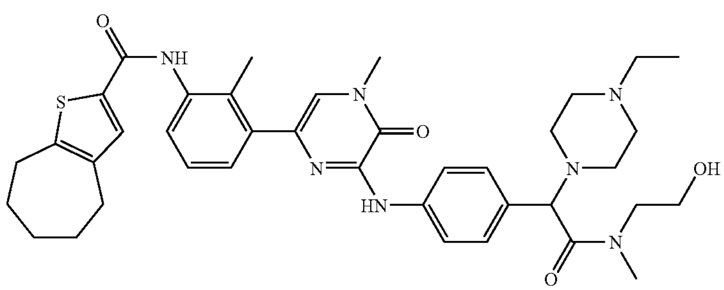 | N-{3-[6-({4-[(4-ethyl-piperazin-1-yl)[(2-hydroxy-ethyl)(methyl)carbamoyl]methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide | 711.36 | 712.4 |
| 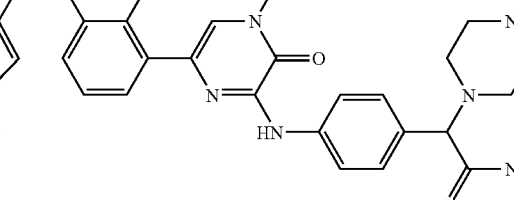 | N-{3-[6-({4-[(diethyl-carbamoyl)(4-ethylpiperazin-1-yl)methyl]phenyl}amino)-4-methyl-5-oxo-4,5-dihydro-pyrazin-2-yl]-2-methyl-phenyl}-4H,5H,6H,7H,8H-cyclohepta[b]thiophene-2-carboxamide | 709.38 | 710.4 |
| 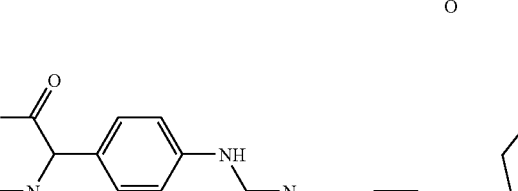 | 4-tert-butyl-N-(3-{6-[(4-{[ethyl(methyl)carbamoyl](4-ethylpiperazin-1-yl)methyl}phenyl)amino]-4-methyl-5-oxo-4,5-dihydropyrazin-2-yl}-2-methylphenyl)benzamide | 677.41 | 678.4 |

-continued

| Structure | Name | MW calc | MH+ m/z obs |
|---|---|---|---|
| 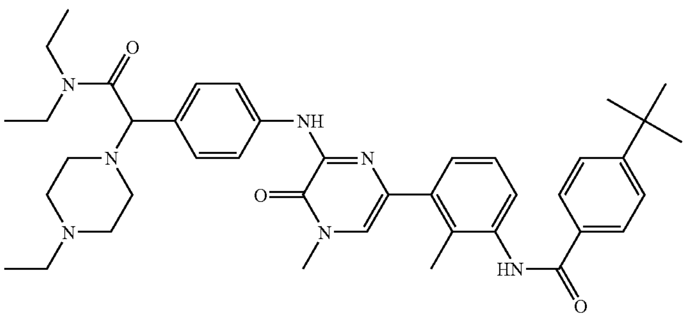 | 4-tert-butyl-N-{3-[6-({4-[(diethylcarbamoyl)(4-ethylpiperazin-1-yl)methyl]phenyl}amino)-4-methyl-5-oxo-4,5-dihydropyrazin-2-yl]-2-methylphenyl}benzamide | 691.42 | 692.4 |
| 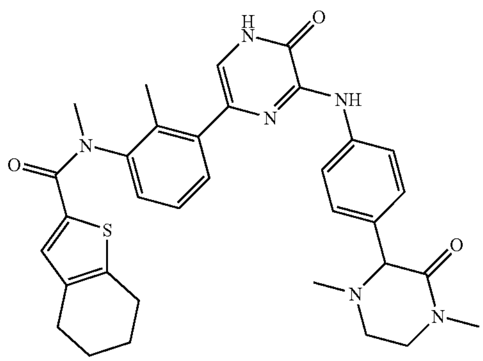 | N-[3-(6-{[4-(1,4-dimethyl-3-oxopiperazin-2-yl)phenyl]amino}-5-oxo-4,5-dihydropyrazin-2-yl)-2-methylphenyl]-N-methyl-4,5,6,7-tetrahydro-1-benzothiophene-2-carboxamide | 596.26 | 597.0 |
| 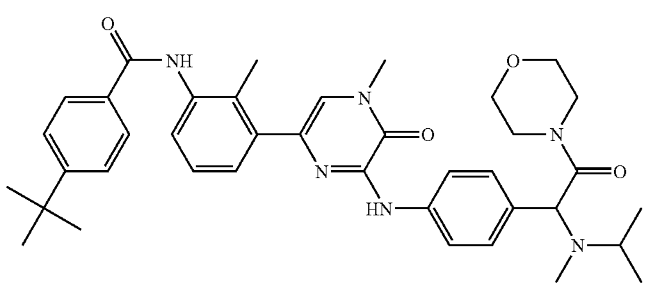 | 4-tert-butyl-N-(2-methyl-3-{4-methyl-6-[(4-{1-[methyl(propan-2-yl)amino]-2-(morpholin-4-yl)-2-oxoethyl}phenyl)amino]-5-oxo-4,5-dihydropyrazin-2-yl}phenyl)benzamide | 664.37 | 665.1 |
| 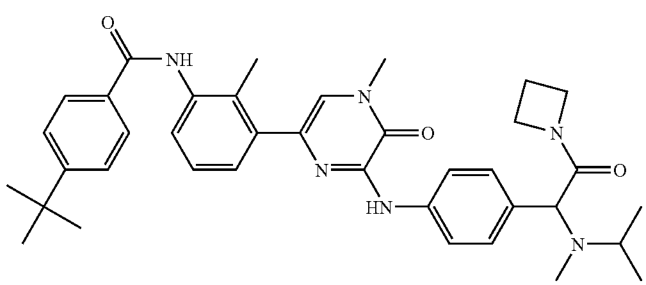 | N-{3-[6-({4-[2-(azetidin-1-yl)-1-[methyl(propan-2-yl)amino]-2-oxoethyl]phenyl}amino)-4-methyl-5-oxo-4,5-dihydropyrazin-2-yl]-2-methylphenyl}-4-tert-butylbenzamide | 634.36 | 635.1 |
| 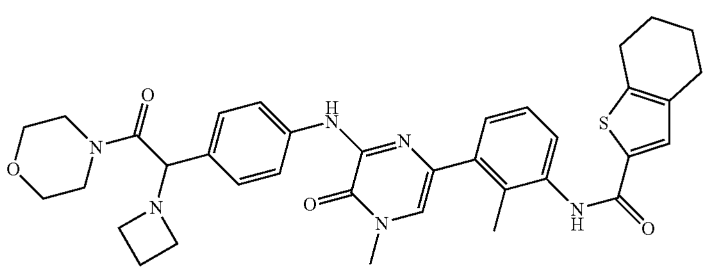 | N-{3-[6-({4-[1-(azetidin-1-yl)-2-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide | 652.28 | 653.7 |

-continued

| Structure | Name | MW calc | MH+ m/z obs |
|---|---|---|---|
| 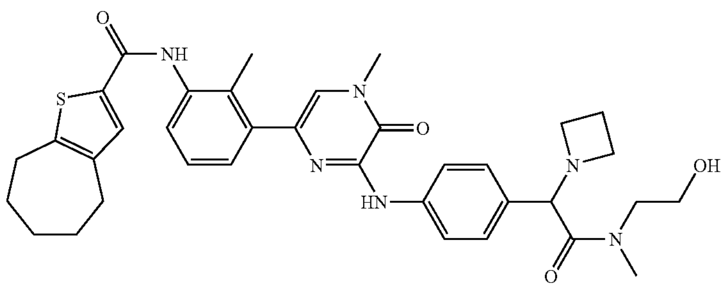 | N-(3-{6-[(4-{azetidin-1-yl[(2-hydroxyethyl)(methyl)carbamoyl]methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide | 654.3 | 655.3 |
| 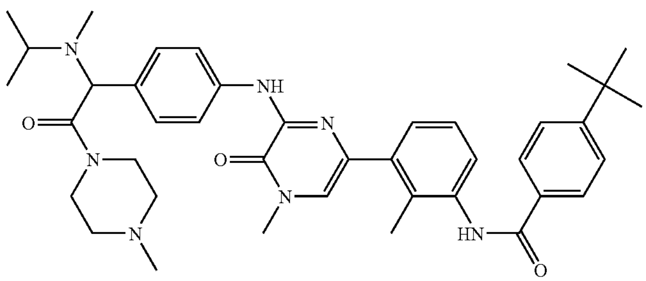 | 4-tert-butyl-N-(2-methyl-3-{4-methyl-6-[(4-{1-[methyl(propan-2-yl)amino]-2-(4-methylpiperazin-1-yl)-2-oxoethyl}phenyl)amino]-5-oxo-4,5-dihydropyrazin-2-yl}phenyl)benzamide | 677.41 | 678.2 |
| 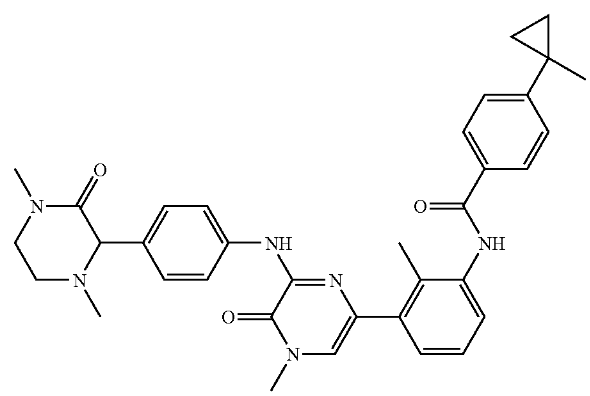 | N-(3-(6-(4-(1,4-dimethyl-3-oxopiperazin-2-yl)phenylamino)-4-methyl-5-oxo-4,5-dihydropyrazin-2-yl)-2-methylphenyl)-4-(1-methylcyclopropyl)benzamide | 590.30 | 591.2 |
| 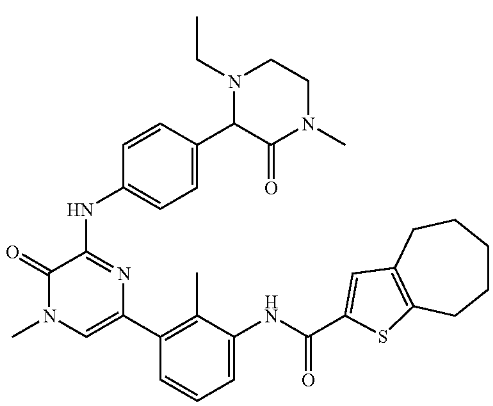 | N-(3-(6-(4-(1-ethyl-4-methyl-3-oxopiperazin-2-yl)phenylamino)-4-methyl-5-oxo-4,5-dihydropyrazin-2-yl)-2-methylphenyl)-5,6,7,8-tetrahydro-4H-cyclohepta[b]thiophene-2-carboxamide | 624.29 | 625.7 |

-continued

| Structure | Name | MW calc | MH+ m/z obs |
|---|---|---|---|
| 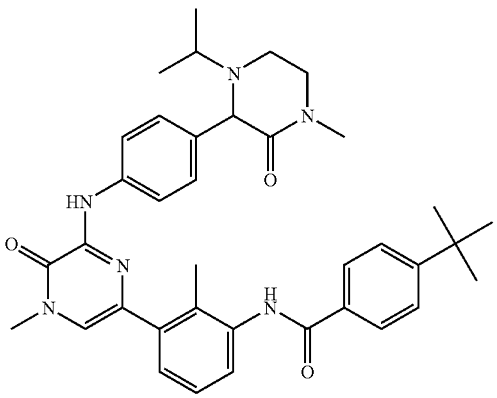 | 4-tert-butyl-N-(3-(6-(4-(1-isopropyl-4-methyl-3-oxopiperazin-2-yl)phenyl-amino)-4-methyl-5-oxo-4,5-dihydropyrazin-2-yl)-2-methylphenyl)benzamide | 620.35 | 621.7 |
| | N-[3-(6-{[4-(1,4-dimethyl-3-oxopiperazin-2-yl)phenyl]amino}-4-methyl-5-oxo-4,5-dihydropyrazin-2-yl)-2-methylphenyl]-N-methyl-4,5,6,7-tetrahydro-1-benzothio-phene-2-carboxamide | 610 | 611.1 |
| 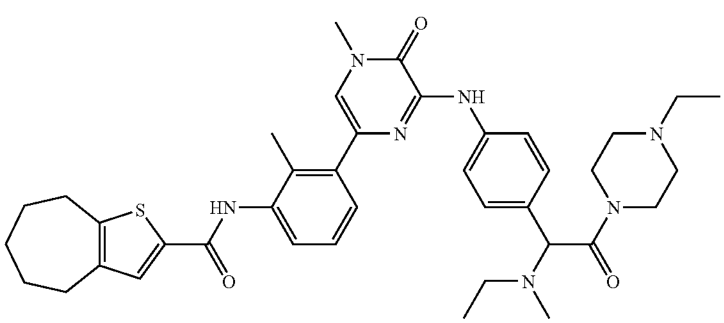 | N-(3-{6-[(4-{1-[ethyl(methyl)amino]-2-(4-ethylpiperazin-1-yl)-2-oxoethyl}phenyl)amino]-4-methyl-5-oxo-4,5-dihydropyrazin-2-yl}-2-methylphenyl)-4H,5H,6H,7H,8H-cyclohepta[b]thiophene-2-carboxamide | 695 | 696.4 |
| 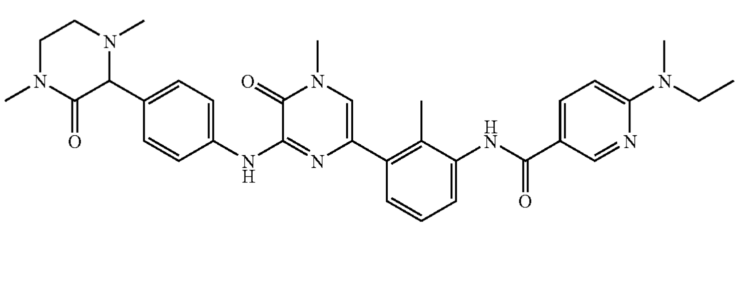 | N-[3-(6-{[4-(1,4-dimethyl-3-oxopiperazin-2-yl)phenyl]amino}-4-methyl-5-oxo-4,5-dihydropyrazin-2-yl)-2-methylphenyl]-6-[ethyl(methyl)amino]pyridine-3-carboxamide | 594 | 595.1 |

| Structure | Name | MW calc | MH+ m/z obs |
|---|---|---|---|
| 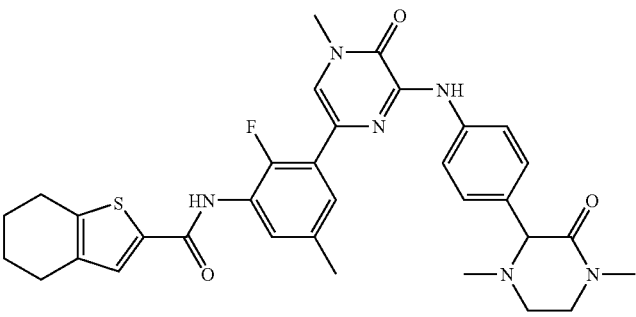 | N-[3-(6-{[4-(1,4-dimethyl-3-oxopiperazin-2-yl)phenyl]amino}-4-methyl-5-oxo-4,5-dihydropyrazin-2-yl)-2-fluoro-5-methylphenyl]-4,5,6,7-tetrahydro-1-benzothiophene-2-carboxamide | 614 | 615.3 |
| 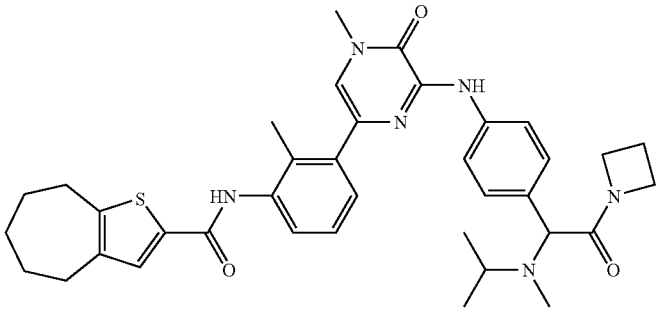 | N-{3-[6-({4-[2-(azetidin-1-yl)-1-[methyl(propan-2-yl)amino]-2-oxoethyl]phenyl}amino)-4-methyl-5-oxo-4,5-dihydropyrazin-2-yl]-2-methylphenyl]-4H,5H,6H,7H,8H-cyclohepta[b]thiophene-2-carboxamide | 652 | 653 |
| 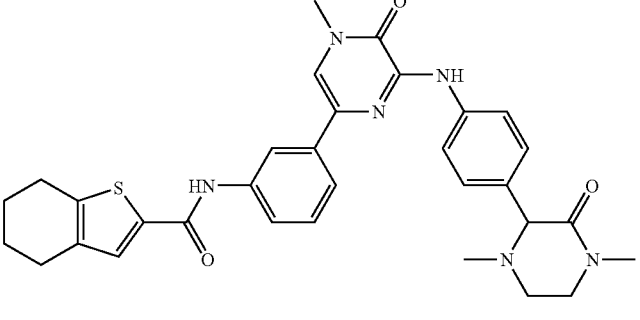 | N-[3-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide | 582 | 583 |
| 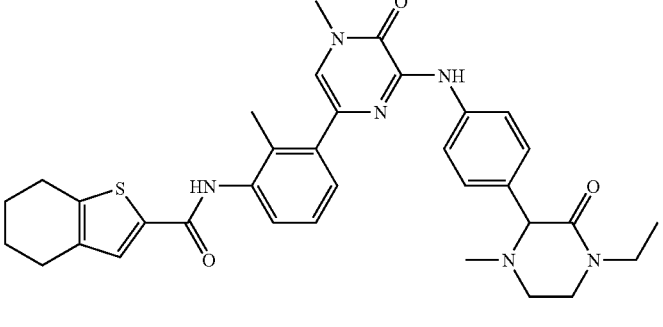 | N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide | 610 | 611.5 |

-continued

| Structure | Name | MW calc | MH+ m/z obs |
|---|---|---|---|
| 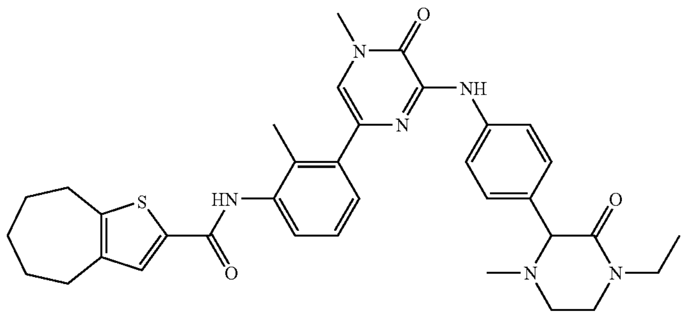 | N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4H,5H,6H,7H,8H-cyclohepta[b]thiophene-2-carboxamide | 624 | 625.3 |
| 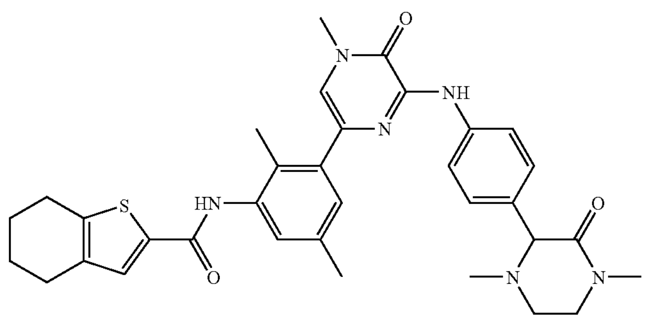 | N-[3-(6-{[4-(1,4-dimethyl-3-oxopiperazin-2-yl)phenyl]amino}-4-methyl-5-oxo-4,5-dihydropyrazin-2-yl)-2,5-dimethylphenyl]-4,5,6,7-tetrahydro-1-benzothiophene-2-carboxamide | 610 | 611.2 |
| 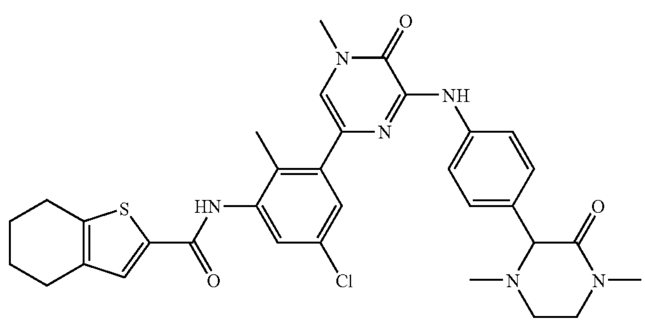 | N-[5-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide | 630 | 631.4 |
| 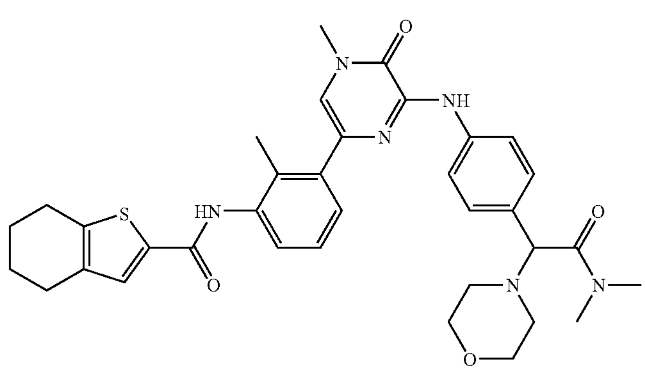 | N-{3-[6-({4-[(dimethylcarbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide | 640 | 640.9 |

-continued

| Structure | Name | MW calc | MH+ m/z obs |
|---|---|---|---|
| 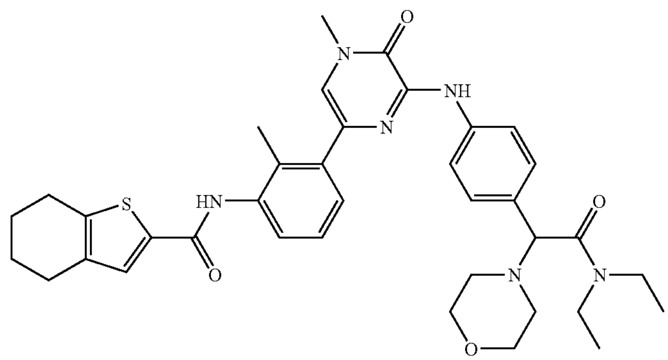 | N-{3-[6-({4-[(diethyl-carbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide | 668 | 668.9 |
| 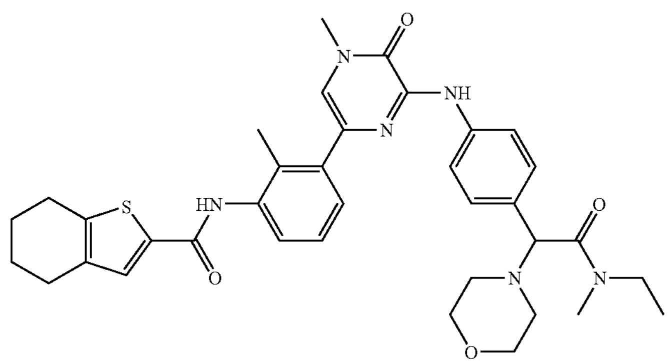 | N-(3-{6-[(4-{[ethyl(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide | 654 | 654.9 |
| 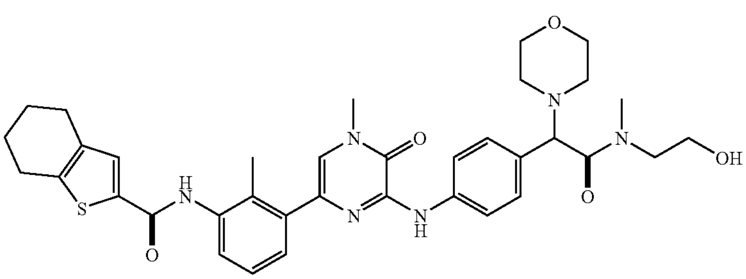 | N-(3-{6-[(4-{[(2-hydroxy-ethyl)(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide | 670 | 670.9 |
| 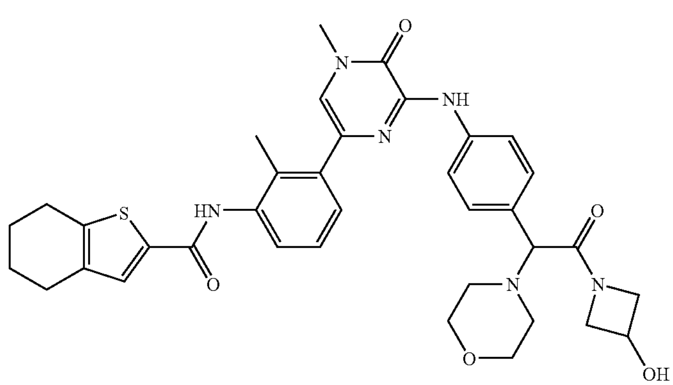 | N-{3-[6-({4-[2-(3-hydroxy-azetidin-1-yl)-1-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide | 668 | 669 |

-continued

| Structure | Name | MW calc | MH+ m/z obs |
|---|---|---|---|
| 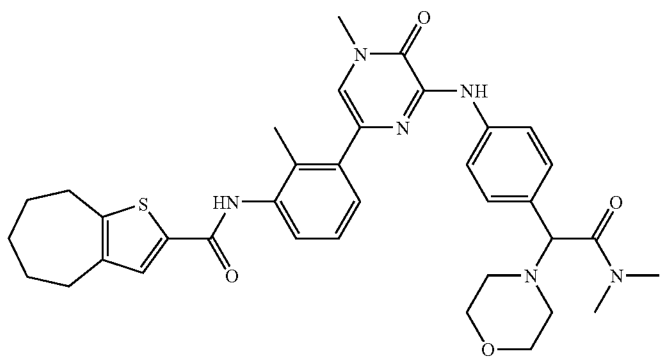 | N-{3-[6-({4-[(dimethyl-carbamoyl)(morpholin-4-yl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide | 654 | 654.9 |
| 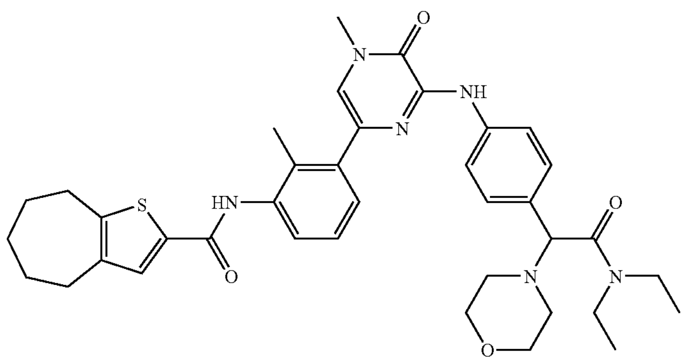 | N-{3-[6-({4-[(diethyl-carbamoyl)(morpholin-4-yl)methyl]phenyl}amino)-4-methyl-5-oxo-4,5-dihydro-pyrazin-2-yl]-2-methyl-phenyl}-4H,5H,6H,7H,8H-cyclohepta[b]thiophene-2-carboxamide | 682 | 683 |
| 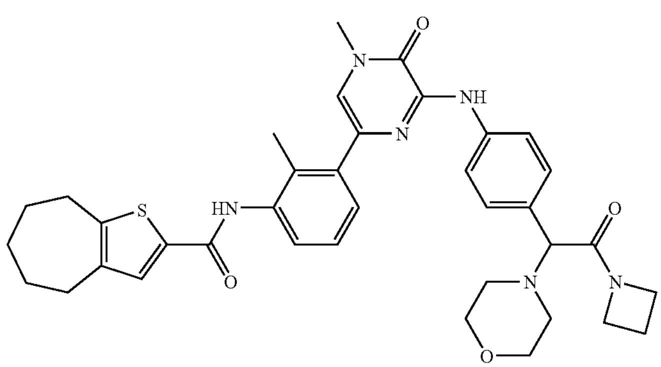 | N-{3-[6-({4-[2-(azetidin-1-yl)-1-(morpholin-4-yl)-2-oxo-ethyl]phenyl}amino)-4-methyl-5-oxo-4,5-dihydro-pyrazin-2-yl]-2-methyl-phenyl}-4H,5H,6H,7H,8H-cyclohepta[b]thiophene-2-carboxamide | 666 | 666.9 |
| 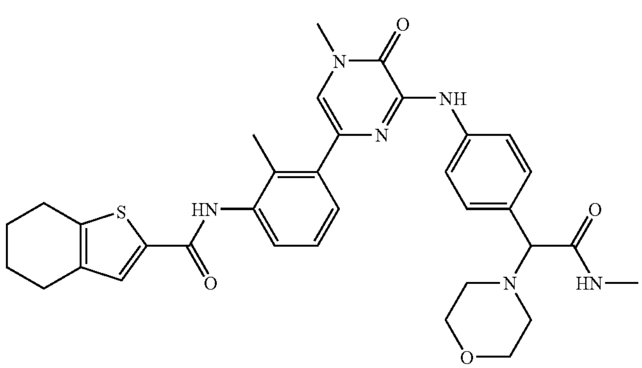 | N-{2-methyl-3-[4-methyl-6-({4-(methylcarbamoyl)(morpholin-4-yl)methyl]phenyl}amino)-5-oxo-4,5-dihydropyrazin-2-yl]phenyl}-4H,5H,6H,7H,8H-cyclohepta[b]thiophene-2-carboxamide | 640 | 640.9 |

-continued

| Structure | Name | MW calc | MH+ m/z obs |
|---|---|---|---|
| 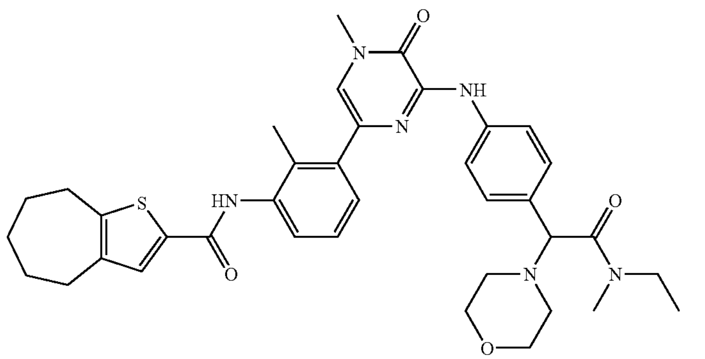 | N-(3-{6-[(4-{[ethyl(methyl)carbamoyl](morpholin-4-yl)methyl}phenyl)amino]-4-methyl-5-oxo-4,5-dihydro-pyrazin-2-yl}-2-methyl-phenyl)-4H,5H,6H,7H,8H-cyclohepta[b]thiophene-2-carboxamide | 668 | 669 |
| | N-(3-{6-[(4-{[(2-hydroxy-ethyl)(methyl)carbamoyl](morpholin-4-yl)methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide | 684 | 685 |
| 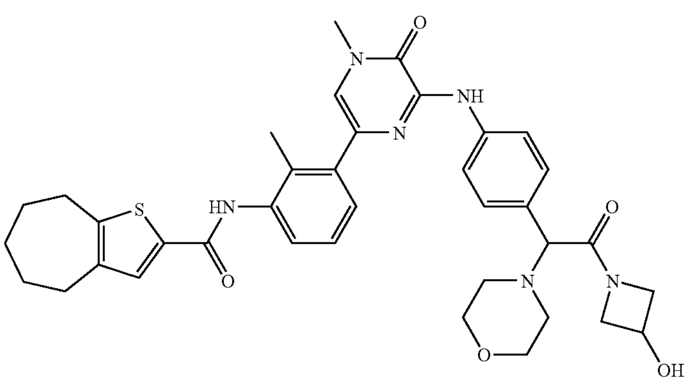 | N-{3-[6-({4-[2-(3-hydroxy-azetidin-1-yl)-1-(morpholin-4-yl)-2-oxoethyl]phenyl}amino)-4-methyl-5-oxo-4,5-dihydro-pyrazin-2-yl]-2-methyl-phenyl}-4H,5H,6H,7H,8H-cyclohepta[b]thiophene-2-carboxamide | 682 | 682.9 |
| 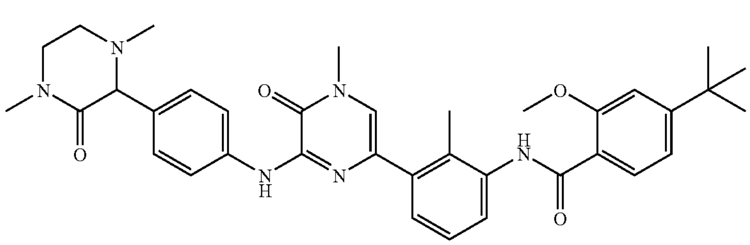 | 4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methoxybenzamide | 622 | 623 |

-continued

| Structure | Name | MW calc | MH+ m/z obs |
|---|---|---|---|
| 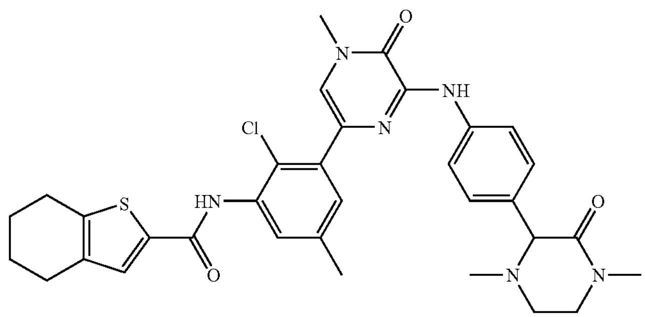 | N-[2-chloro-3-(6-{[4-(1,4-dimethyl-3-oxopiperazin-2-yl)phenyl]amino}-4-methyl-5-oxo-4,5-dihydropyrazin-2-yl)-5-methylphenyl]-4,5,6,7-tetrahydro-1-benzothiophene-2-carboxamide | 630 | 631.5 |
| 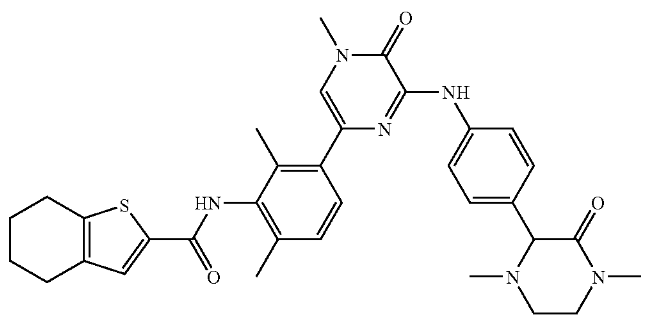 | N-[3-(6-{[4-(1,4-dimethyl-3-oxopiperazin-2-yl)phenyl]amino}-4-methyl-5-oxo-4,5-dihydropyrazin-2-yl)-2,6-dimethylphenyl]-4,5,6,7-tetrahydro-1-benzothiophene-2-carboxamide | 610 | 611.4 |
| 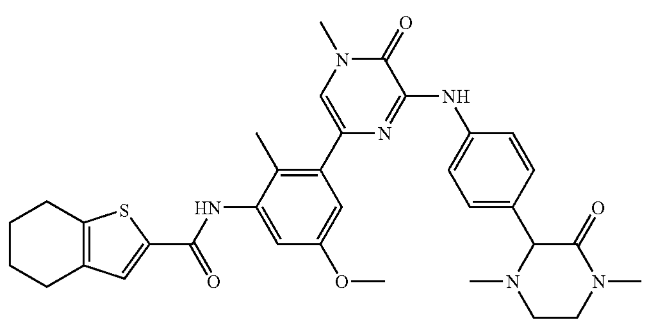 | N-[3-(6-{[4-(1,4-dimethyl-3-oxopiperazin-2-yl)phenyl]amino}-4-methyl-5-oxo-4,5-dihydropyrazin-2-yl)-5-methoxy-2-methylphenyl]-4,5,6,7-tetrahydro-1-benzothiophene-2-carboxamide | 626 | 627.3 |
| 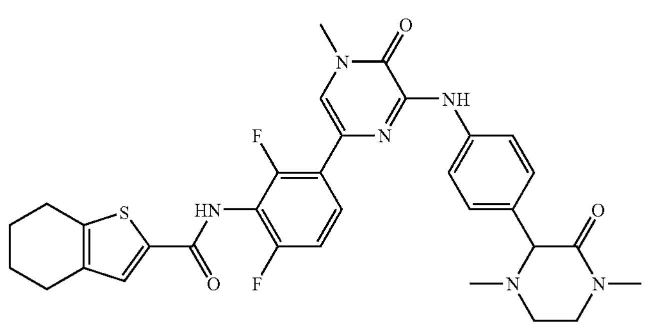 | N-[3-(6-{[4-(1,4-dimethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide | 618 | 619.2 |

-continued

| Structure | Name | MW calc | MH+ m/z obs |
|---|---|---|---|
| 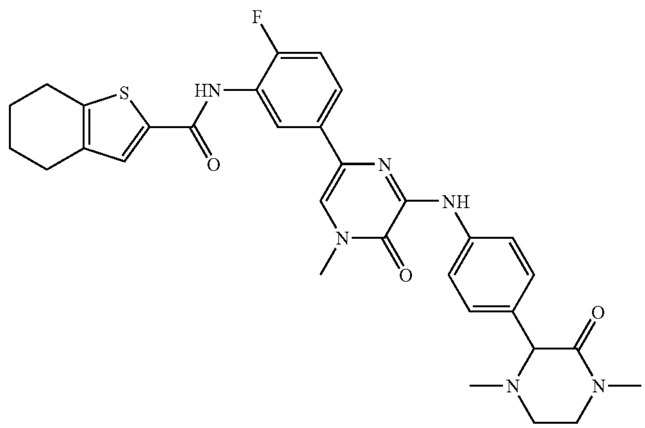 | N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 600 | 601.3 |
| 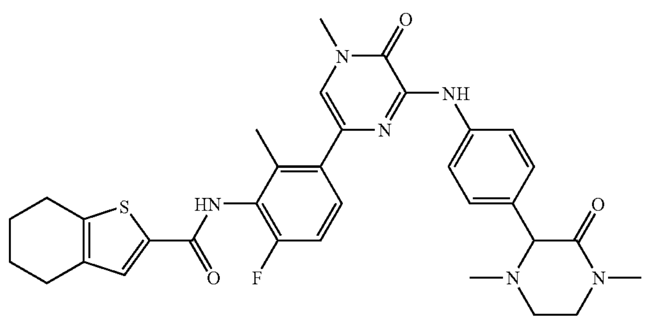 | N-[3-(6-{[4-(1,4-dimethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide | 614 | 615.3 |
| 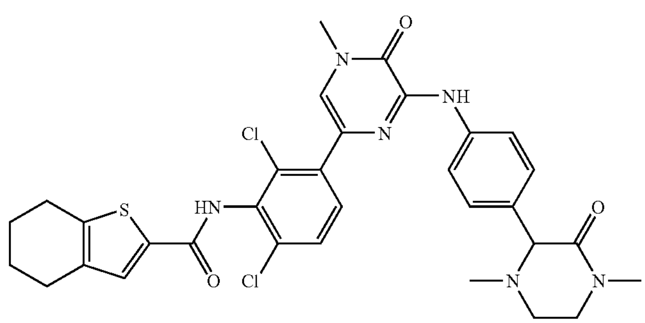 | N-[2,6-dichloro-3-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide | 650 | 651.4 |
| 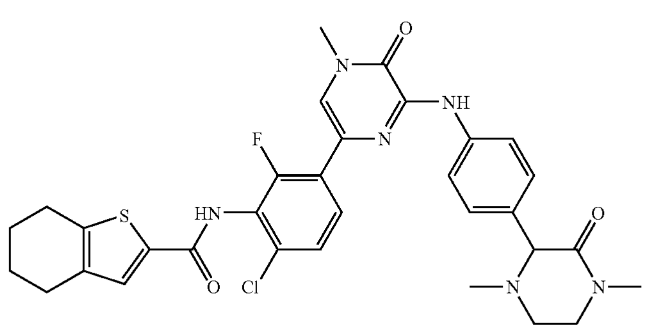 | N-[6-chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 634 | 635.2 |

| Structure | Name | MW calc | MH+ m/z obs |
|---|---|---|---|
| 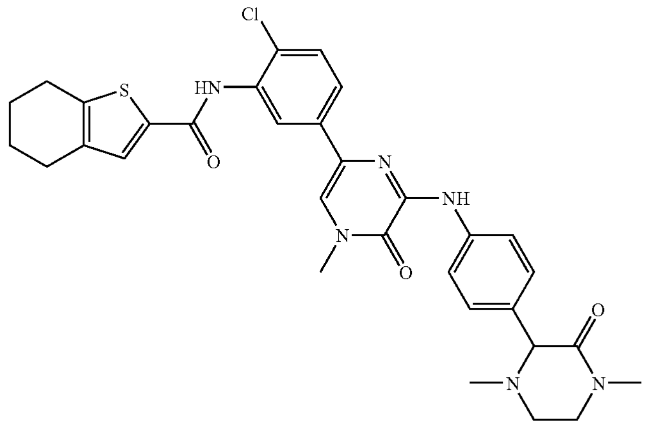 | N-[2-chloro-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide | 616 | 617.2 |
| 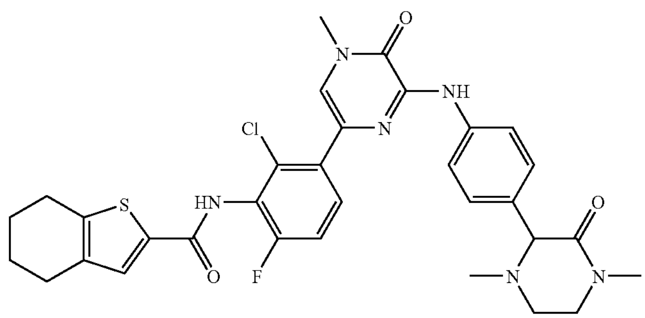 | N-[2-chloro-3-(6-{[4-(1,4-dimethyl-3-oxopiperazin-2-yl)phenyl]amino}-4-methyl-5-oxo-4,5-dihydropyrazin-2-yl)-6-fluorophenyl]-4,5,6,7-tetrahydro-1-benzothiophene-2-carboxamide | 634 | 635.2 |
| 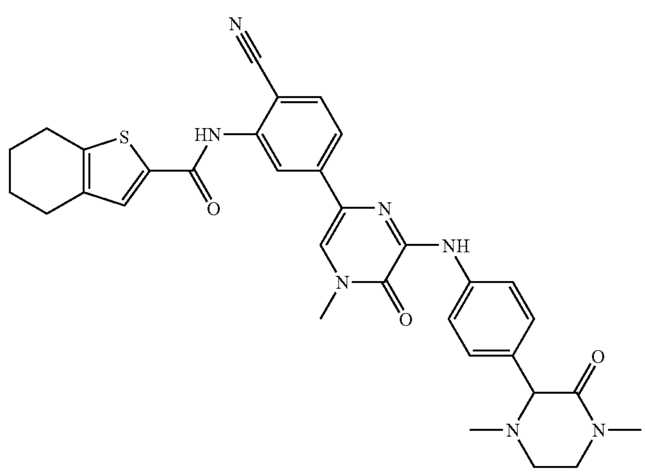 | N-[2-cyano-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide | 607 | 608.2 |
| 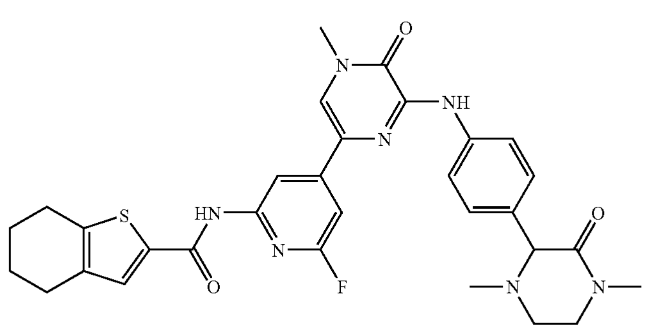 | N-[4-(6-{[4-(1,4-dimethyl-3-oxopiperazin-2-yl)phenyl]amino}-4-methyl-5-oxo-4,5-dihydropyrazin-2-yl)-6-fluoropyridin-2-yl]-4,5,6,7-tetrahydro-1-benzothiophene-2-carboxamide | 601 | 602.2 |

-continued

| Structure | Name | MW calc | MH+ m/z obs |
|---|---|---|---|
| 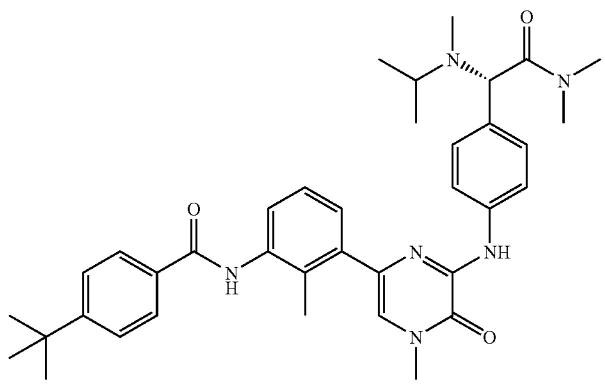 | 4-tert-butyl-N-{3-[6-({4-[(S)-(dimethylcarbamoyl)[methyl(propan-2-yl)amino]methyl]phenyl}amino)-4-methyl-5-oxo-4,5-dihydropyrazin-2-yl]-2-methylphenyl}benzamide | 622 | 623.4 |
| 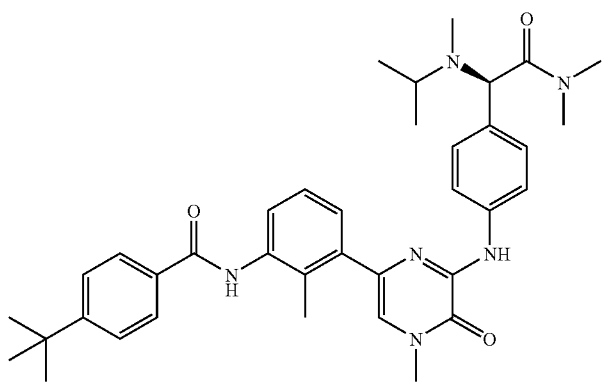 | 4-tert-butyl-N-{3-[6-({4-[(R)-(dimethylcarbamoyl)[methyl(propan-2-yl)amino]methyl]phenyl}amino)-4-methyl-5-oxo-4,5-dihydropyrazin-2-yl]-2-methylphenyl}benzamide | 622 | 623.4 |
| 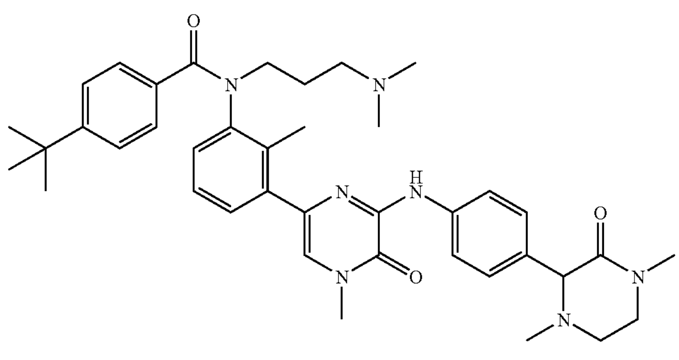 | 4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-N-[3-(dimethylamino)propyl]benzamide | 677 | 678.4 |
| 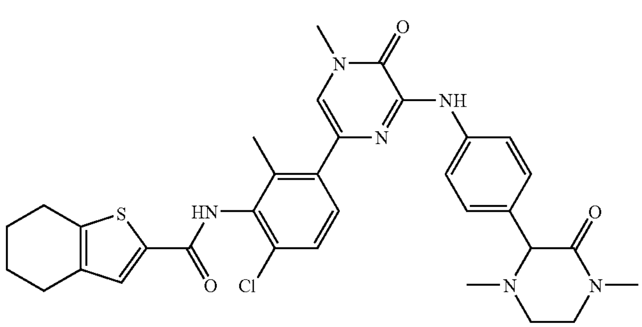 | N-[6-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide | 630 | 631.3 |

-continued

| Structure | Name | MW calc | MH+ m/z obs |
|---|---|---|---|
| 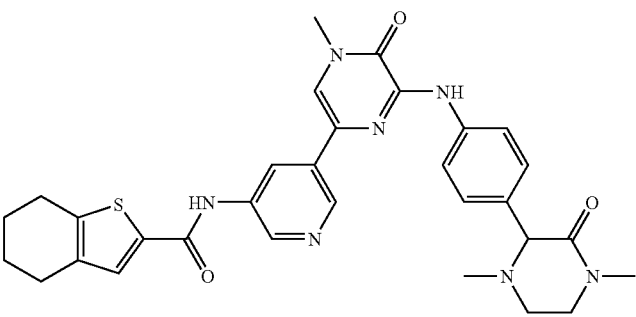 | N-[5-(6-{[4-(1,4-dimethyl-3-oxopiperazin-2-yl)phenyl]amino}-4-methyl-5-oxo-4,5-dihydropyrazin-2-yl)pyridin-3-yl]-4,5,6,7-tetrahydro-1-benzothiophene-2-carboxamide | 583 | 584.2 |
| 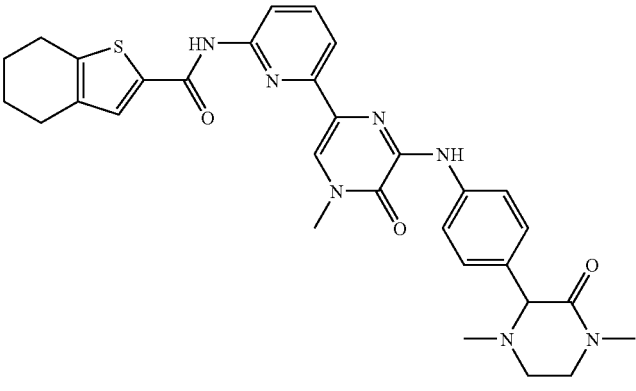 | N-[6-(6-{[4-(1,4-dimethyl-3-oxopiperazin-2-yl)phenyl]amino}-4-methyl-5-oxo-4,5-dihydropyrazin-2-yl)pyridin-2-yl]-4,5,6,7-tetrahydro-1-benzothiophene-2-carboxamide | 583 | 584.2 |
| 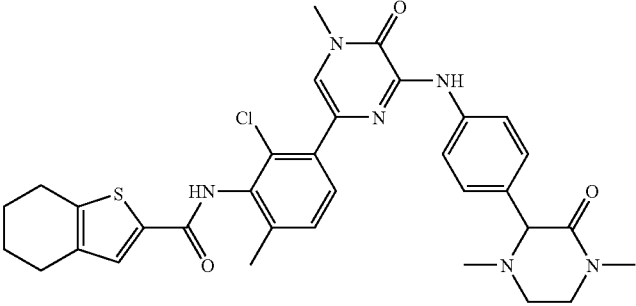 | N-[2-chloro-3-(6-{[4-(1,4-dimethyl-3-oxopiperazin-2-yl)phenyl]amino}-4-methyl-5-oxo-4,5-dihydropyrazin-2-yl)-6-methylphenyl]-4,5,6,7-tetrahydro-1-benzothiophene-2-carboxamide | 630 | 631.3 |
| 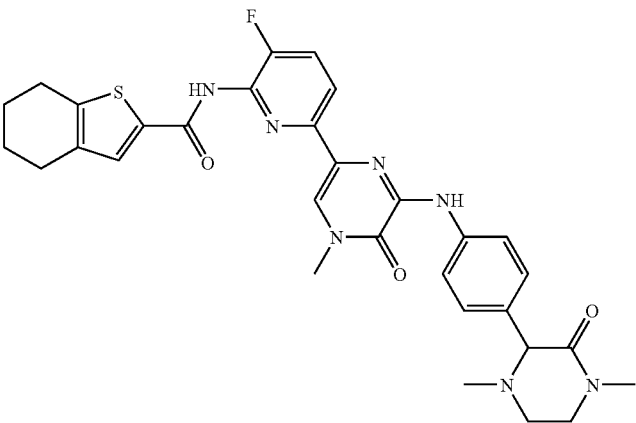 | N-[6-(6-{[4-(1,4-dimethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide | 601 | 602.2 |

-continued

| Structure | Name | MW calc | MH+ m/z obs |
|---|---|---|---|
| 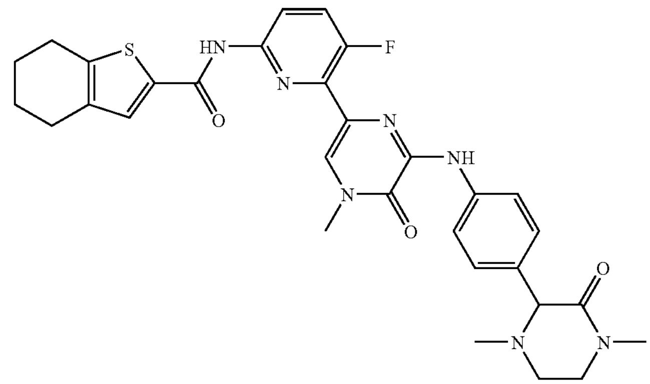 | N-[6-(6-{[4-(1,4-dimethyl-3-oxopiperazin-2-yl)phenyl]amino}-4-methyl-5-oxo-4,5-dihydropyrazin-2-yl)-5-fluoropyridin-2-yl]-4,5,6,7-tetrahydro-1-benzothiophene-2-carboxamide | 601 | 602.2 |
| 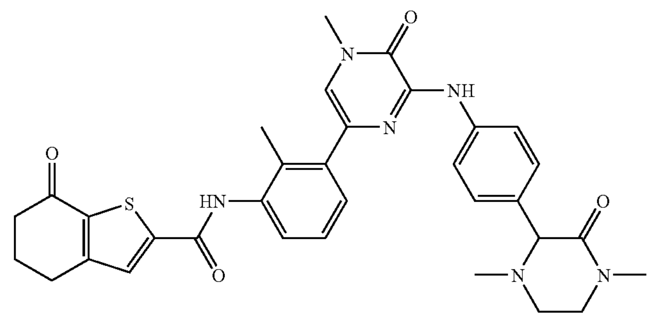 | N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-oxo-4,5,6,7-tetrahydro-1-benzothiophene-2-carboxamide | 610 | 611.2 |
| 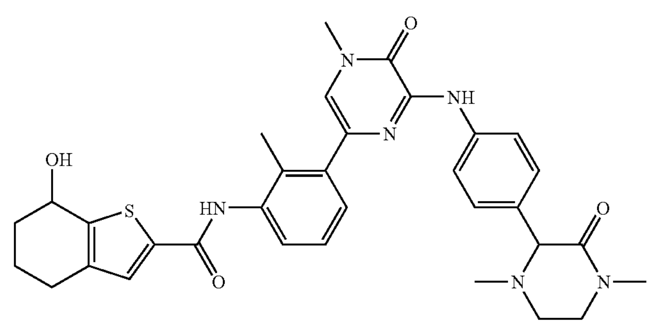 | N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-hydroxy-4,5,6,7-tetrahydro-1-benzothiophene-2-carboxamide | 612 | 613.3 |
| 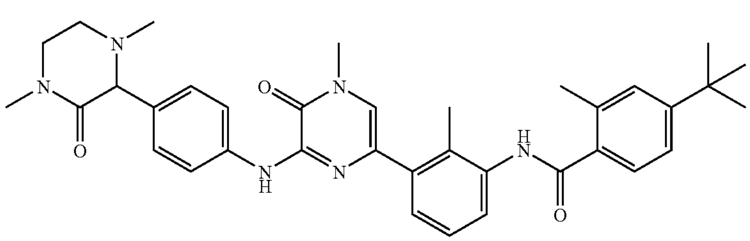 | 4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methylbenzamide | 606 | 607.3 |

-continued

| Structure | Name | MW calc | MH+ m/z obs |
|---|---|---|---|
| 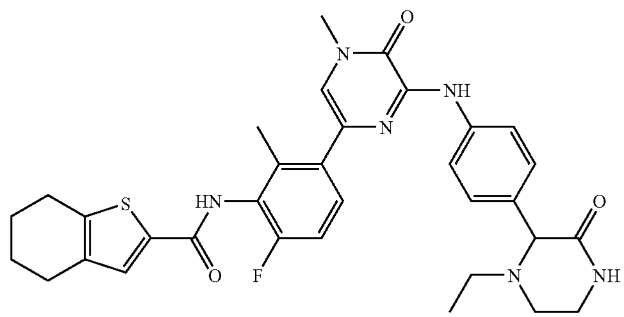 | N-[3-(6-{[4-(1-ethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide | 614 | 615.3 |
| 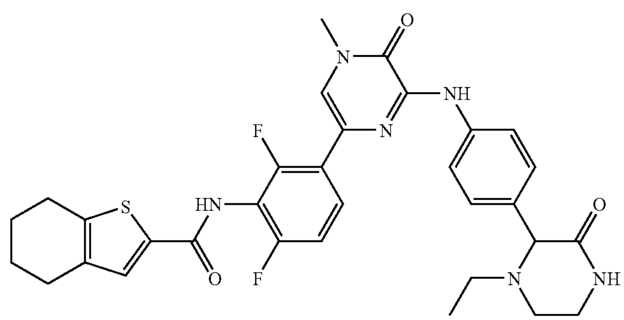 | N-[3-(6-{[4-(1-ethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide | 618 | 619.3 |
| 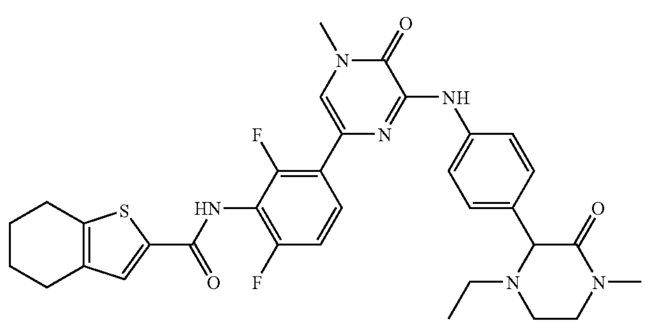 | N-[3-(6-{[4-(1-ethyl-4-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide | 632 | 633.3 |
| 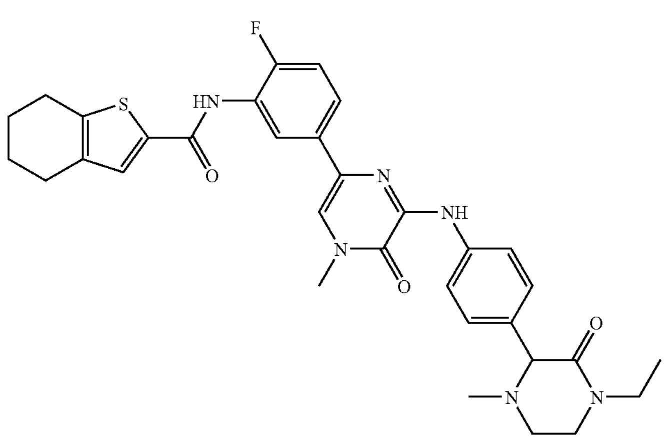 | N-[5-(6-{[4-(4-ethyl-1-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 614 | 615.2 |

-continued

| Structure | Name | MW calc | MH+ m/z obs |
|---|---|---|---|
| 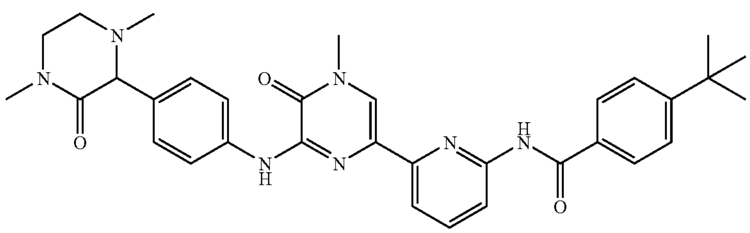 | 4-tert-butyl-N-[6-(6-{[4-(1,4-dimethyl-3-oxopiperazin-2-yl)phenyl]amino}-4-methyl-5-oxo-4,5-dihydropyrazin-2-yl)pyridin-2-yl]benzamide | 579 | 580.3 |
| 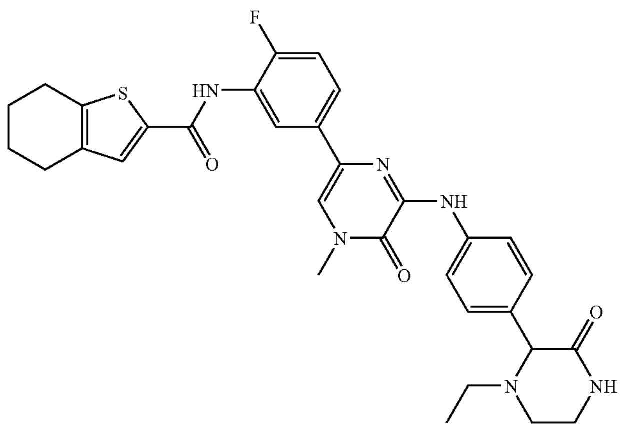 | N-[5-(6-{[4-(1-ethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 600 | 601.3 |
| 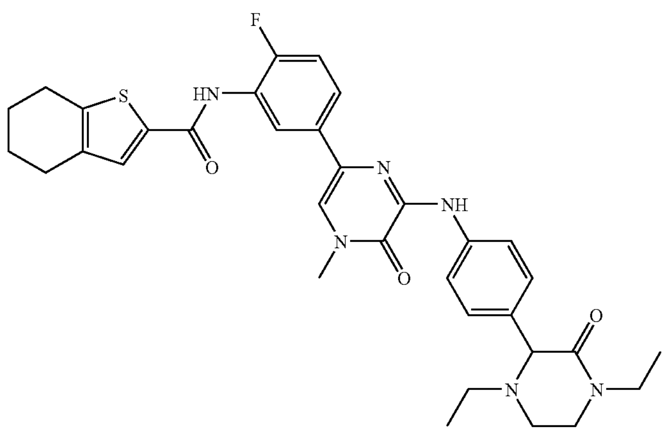 | N-[5-(6-{[4-(1,4-diethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 628 | 629.3 |
| 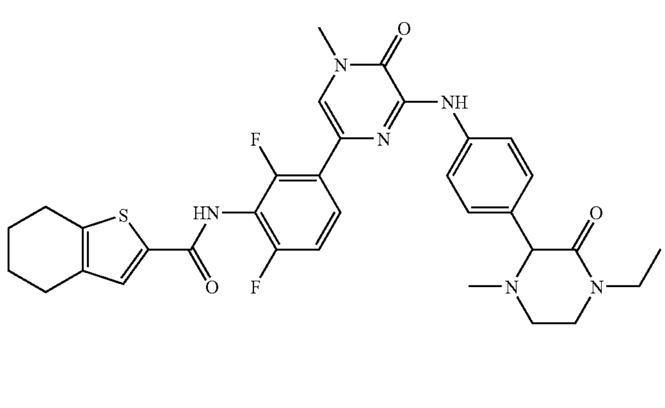 | N-[3-(6-{[4-(4-ethyl-1-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide | 632 | 633.3 |

-continued

| Structure | Name | MW calc | MH+ m/z obs |
|---|---|---|---|
| 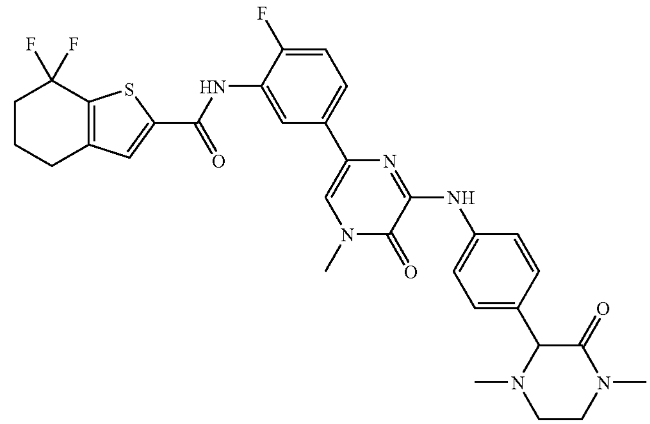 | N-[5-(6-{[4-(1,4-dimethyl-3-oxopiperazin-2-yl)phenyl]amino}-4-methyl-5-oxo-4,5-dihydropyrazin-2-yl)-2-fluorophenyl]-7,7-difluoro-4,5,6,7-tetrahydro-1-benzothiophene-2-carboxamide | 636 | 637.3 |
| 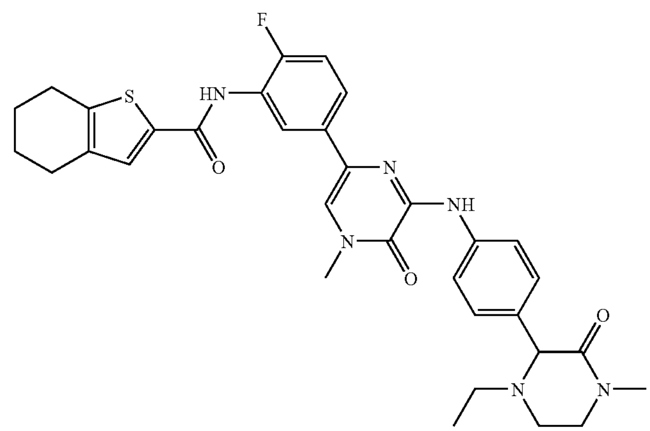 | N-[5-(6-{[4-(1-ethyl-4-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 614 | 615.3 |
| 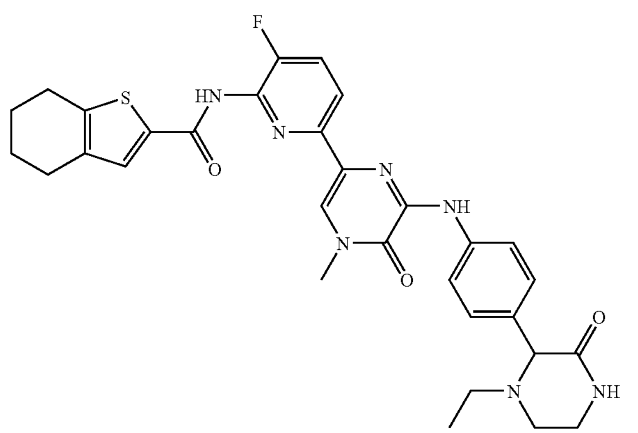 | N-[6-(6-{[4-(1-ethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide | 601 | 602.2 |

-continued

| Structure | Name | MW calc | MH+ m/z obs |
|---|---|---|---|
| 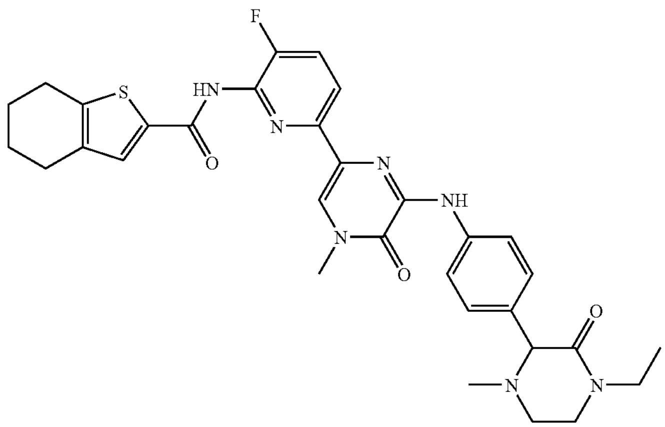 | N-[6-(6-{[4-(4-ethyl-1-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide | 615 | 616.3 |
| 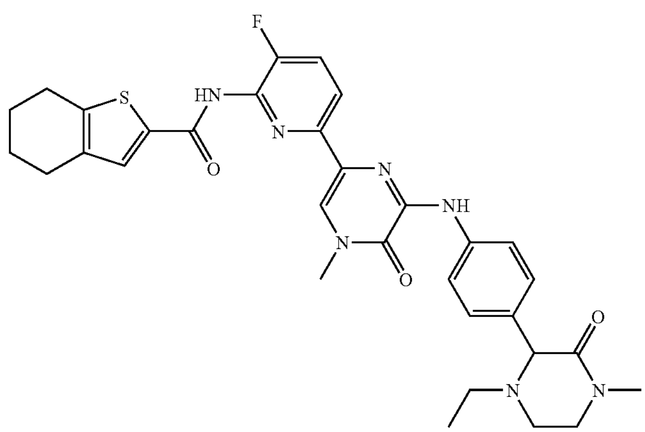 | N-[6-(6-{[4-(1-ethyl-4-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide | 615 | 616.3 |
| 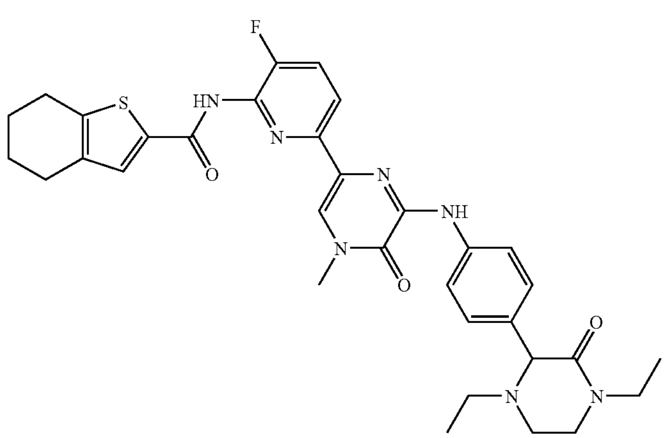 | N-[6-(6-{[4-(1,4-diethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide | 629 | 630.3 |

-continued

| Structure | Name | MW calc | MH+ m/z obs |
|---|---|---|---|
| 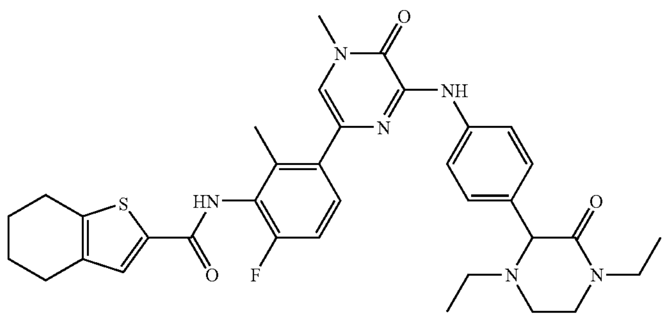 | N-[3-(6-{[4-(1,4-diethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide | 642 | 643.3 |
| 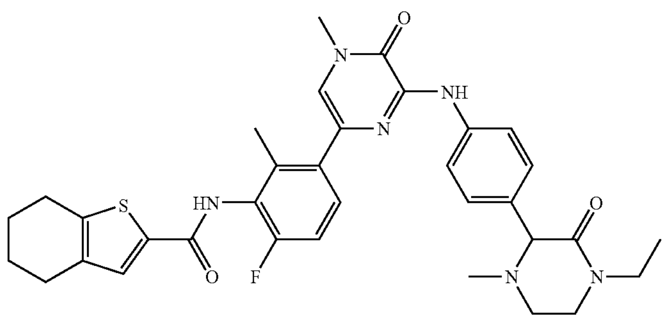 | N-[3-(6-{[4-(4-ethyl-1-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide | 628 | 629.4 |
| 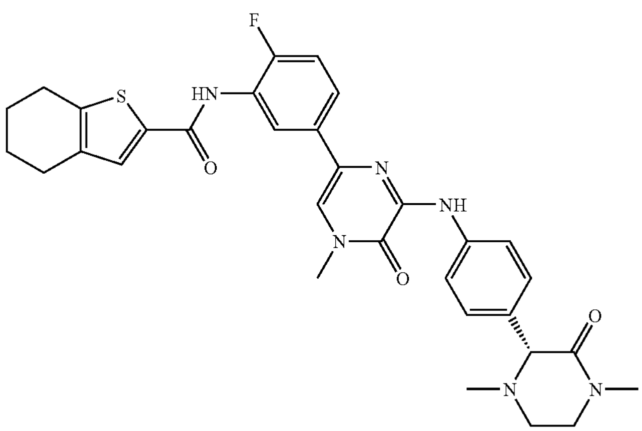 | N-{5-[6-({4-[(2R)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide | 600 | 601.2 |
| 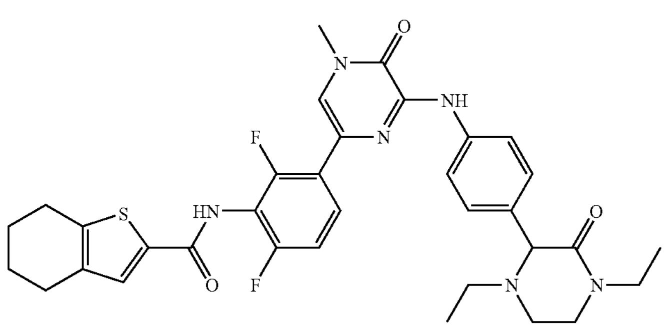 | N-[3-(6-{[4-(1,4-diethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide | 646 | 647.3 |

-continued

| Structure | Name | MW calc | MH+ m/z obs |
|---|---|---|---|
| 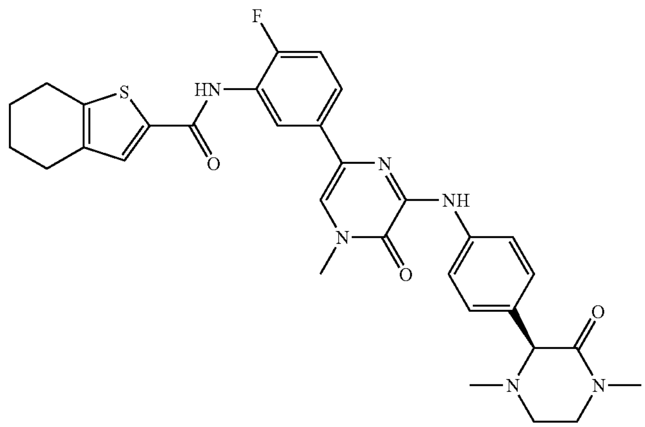 | N-{5-[6-({4-[(2S)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide | 600 | 601.5 |
| 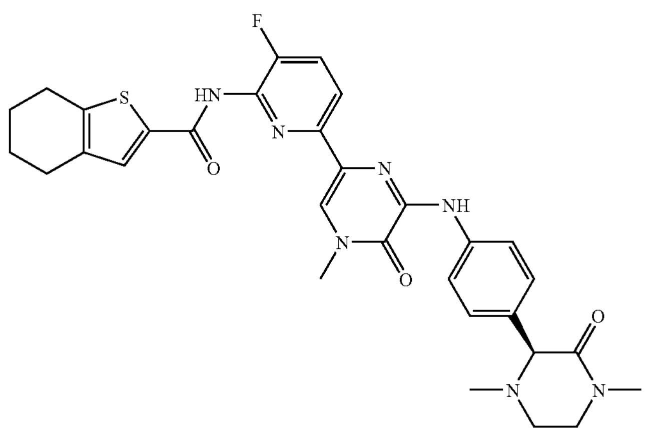 | N-{6-[6-({4-[(2S)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide | 601 | 602.3 |
| 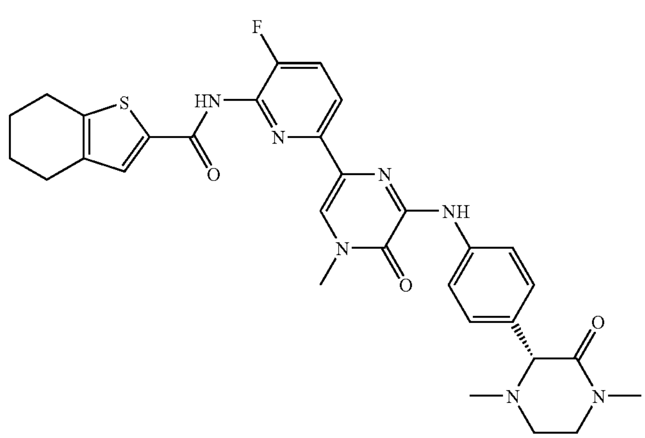 | N-{6-[6-({4-[(2R)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide | 601 | 602.2 |

-continued

| Structure | Name | MW calc | MH+ m/z obs |
|---|---|---|---|
| 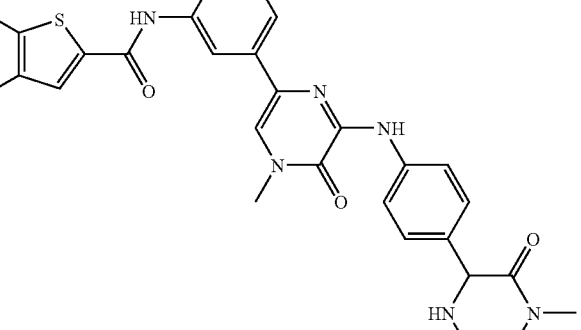 | N-[2-fluoro-5-(4-methyl-6-{[4-(4-methyl-3-oxopiperazin-2-yl)phenyl]amino}-5-oxo-4,5-dihydropyrazin-2-yl)phenyl]-4,5,6,7-tetrahydro-1-benzothiophene-2-carboxamide | 586 | 587.2 |
| 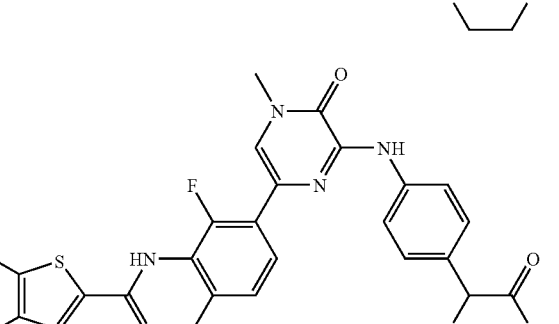 | N-[3-(6-{[4-(1,4-dimethyl-3-oxopiperazin-2-yl)phenyl]amino}-4-methyl-5-oxo-4,5-dihydropyrazin-2-yl)-2-fluoro-6-methylphenyl]-4,5,6,7-tetrahydro-1-benzothiophene-2-carboxamide | 614 | 615.3 |
| 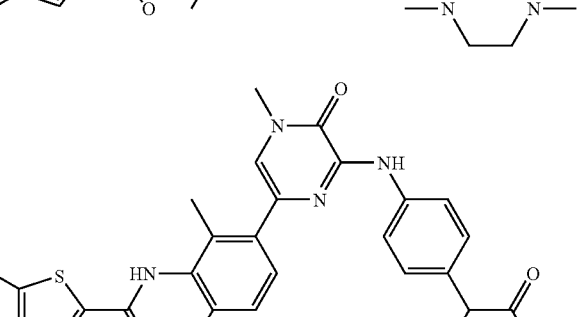 | N-[3-(6-{[4-(1-ethyl-4-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide | 628 | 629.3 |
| 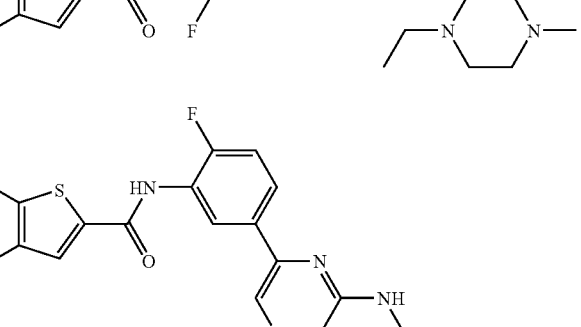 | N-[5-(6-{[4-(2,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide | 600 | 601.6 |

| Structure | Name | MW calc | MH+ m/z obs |
|---|---|---|---|
| 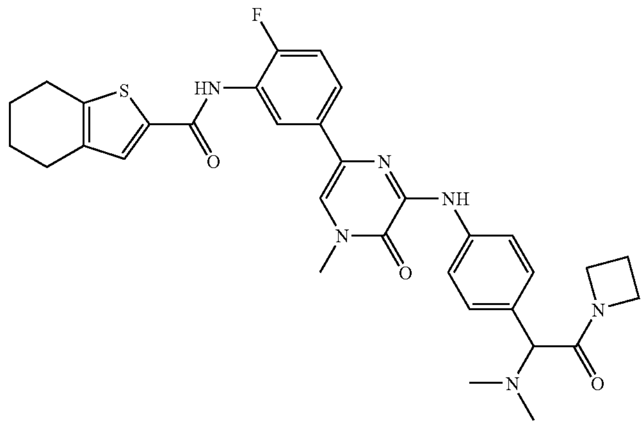 | N-{5-[6-({4-[2-(azetidin-1-yl)-1-(dimethylamino)-2-oxoethyl]phenyl}amino)-4-methyl-5-oxo-4,5-dihydropyrazin-2-yl]-2-fluorophenyl}-4,5,6,7-tetrahydro-1-benzothiophene-2-carboxamide | 614 | 615.22 |
| 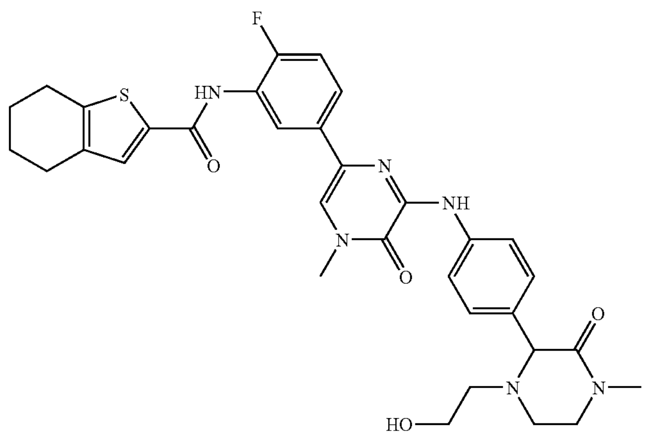 | N-{2-fluoro-5-[6-({4-[1-(2-hydroxyethyl)-4-methyl-3-oxopiperazin-2-yl]phenyl}amino)-4-methyl-5-oxo-4,5-dihydropyrazin-2-yl]phenyl}-4,5,6,7-tetrahydro-1-benzothiophene-2-carboxamide | 630 | 631.3 |
| 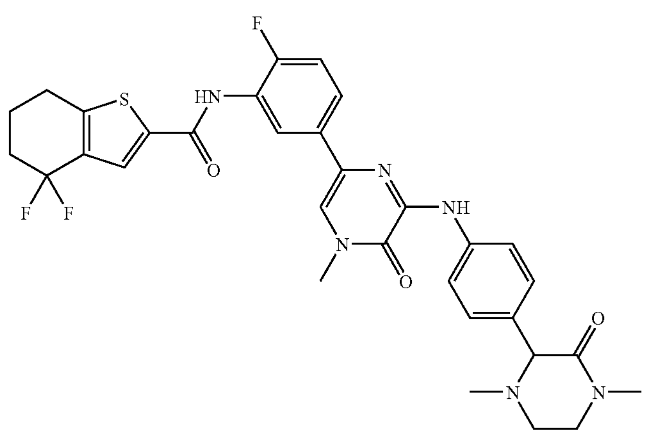 | N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,4-difluoro-4,5,6,7-tetrahydro-1-benzothiophene-2-carboxamide | 636 | 637.3 |

-continued

| Structure | Name | MW calc | MH+ m/z obs |
|---|---|---|---|
| 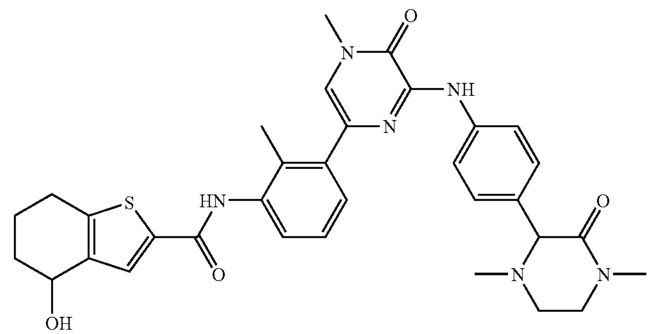 | N-[3-(6-{[4-(1,4-dimethyl-3-oxopiperazin-2-yl)phenyl]amino}-4-methyl-5-oxo-4,5-dihydropyrazin-2-yl)-2-methylphenyl]-4-hydroxy-4,5,6,7-tetrahydro-1-benzothiophene-2-carboxamide | 612 | 613.3 |
| 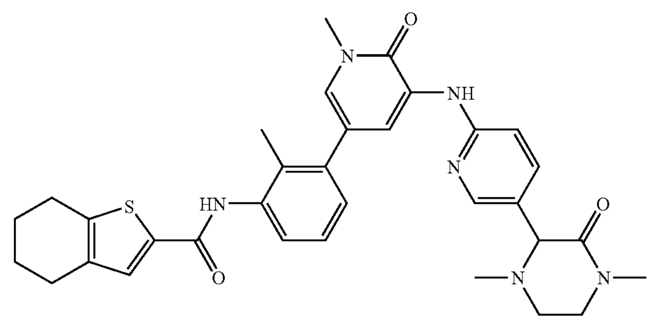 | N-[3-(5-{[5-(1,4-dimethyl-3-oxopiperazin-2-yl)pyridin-2-yl]amino}-1-methyl-6-oxo-1,6-dihydropyridin-3-yl)-2-methylphenyl]-4,5,6,7-tetrahydro-1-benzothiophene-2-carboxamide | 596 | 597 |

EXAMPLE 11

Biochemical Btk Assay

A generalized procedure for one standard biochemical Btk Kinase Assay that can be used to test compounds disclosed in this application is as follows.

A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6× His tag was subcloned into pFastBac vector for making baculovirus carrying this epitope-tagged Btk. Generation of baculovirus is done based on Invitrogen's instructions detailed in its published protocol "Bac-toBac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 μM ATP is prepared in water and adjusted to pH 7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM MgCl2, 2 mM $MnCl_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 and 520 nm.

EXAMPLE 12

Ramos Cell Btk Assay

Another generalized procedure for a standard cellular Btk Kinase Assay that can be used to test compounds disclosed in this application is as follows.

Ramos cells are incubated at a density of $0.5 \times 10^7$ cells/ml in the presence of test compound for 1 hr at 37° C. Cells are then stimulated by incubating with 10 µg/ml anti-human IgM $F(ab)_2$ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

EXAMPLE 13

B-Cell Proliferation Assay

A generalized procedure for a standard cellular B-cell proliferation assay that can be used to test compounds disclosed in this application is as follows.

B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

EXAMPLE 14

T Cell Proliferation Assay

A generalized procedure for a standard T cell proliferation assay that can be used to test compounds disclosed in this application is as follows.

T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

EXAMPLE 15

CD86 Inhibition Assay

A generalized procedure for a standard assay for the inhibition of B cell activity that can be used to test compounds disclosed in this application is as follows.

Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration.

EXAMPLE 16

B-ALL Cell Survival Assay

The following is a procedure for a standard B-ALL cell survival study using an XTT readout to measure the number of viable cells. This assay can be used to test compounds disclosed in this application for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution (Roche) is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

EXAMPLE 17

The compounds disclosed in the examples above were tested in the Btk biochemical assay described herein (Example 11) and all of those compounds of Formula I disclosed in the examples above exhibited an $IC_{50}$ value less than or equal to 2 micromolar and certain of those compounds exhibited an $IC_{50}$ value less than or equal to 1 micromolar. Certain of those compounds exhibited an $IC_{50}$ value less than or equal to 25 nM. Certain of those compounds exhibited an $IC_{50}$ value less than or equal to 5 nM.

Some of the compounds disclosed in the examples above were tested in the B-cell proliferation assay (as described in Example 13) and exhibited an $IC_{50}$ value less than or equal to 10 micromolar. Certain of those compounds exhibited an $IC_{50}$ value less than or equal to 500 nM. Certain of those compounds exhibited an $IC_{50}$ value less than or equal to 50 nM in this assay.

Certain compounds disclosed herein exhibited $IC_{50}$ values for inhibition of T-cell proliferation that were at least 3-fold, and in some instances 10-fold, or even 100-fold greater than the $IC_{50}$ values of those compounds for inhibition of B-cell proliferation.

Some of the compounds disclosed herein were tested in an assay for inhibition of B cell activity (under the conditions described in Example 15), and exhibited an $IC_{50}$ value less than or equal to 10 micromolar. Certain of those compounds exhibited an $IC_{50}$ value less than or equal to 0.5 micromolar. Certain of those compounds exhibited an $IC_{50}$ value less than or equal to 100 nM in this assay.

Some of the compounds disclosed herein were tested in a B-cell leukemia cell survival assay (under the conditions described in Example 16), and exhibit an $IC_{50}$ value less than or equal to 10 micromolar.

Some of the compounds disclosed herein exhibited both biochemical and cell-based activity. For example, some of the compounds disclosed herein exhibited an $IC_{50}$ value less than or equal to 1 micromolar in the Btk biochemical assay described herein (Example 11) and an $IC_{50}$ value less than or equal to 10 micromolar in at least one of the cell-based assays (other than the T-cell assay) described herein (Examples 12, 13, 15 or 16). Certain of those compounds exhibited an $IC_{50}$ value less than or equal to 50 nM in the Btk biochemical assay described herein (Example 11) and an $IC_{50}$ value less than or equal to 500 nM in at least one of the cell-based assays (other than the T-cell assay) described herein (Examples 12, 13, 15 or 16). Certain of those compounds exhibited an $IC_{50}$ value less than or equal to 10 nM and an $IC_{50}$ value less than or equal to 100 nM in at least one of the cell-based assays (other than the T-cell assay) described herein (Examples 12, 13, 15 or 16).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed is:

1. A compound of Formula I, or a pharmaceutically acceptable salt thereof or mixture thereof, wherein (Formula I)

X is chosen from N and $CR^2$;

Y is chosen from N and $CR^3$;

Z is chosen from N and $CR^3$; provided that only one of X, Y and Z is N at a time;

W is N;

V is CH;

$R^1$ is chosen from:

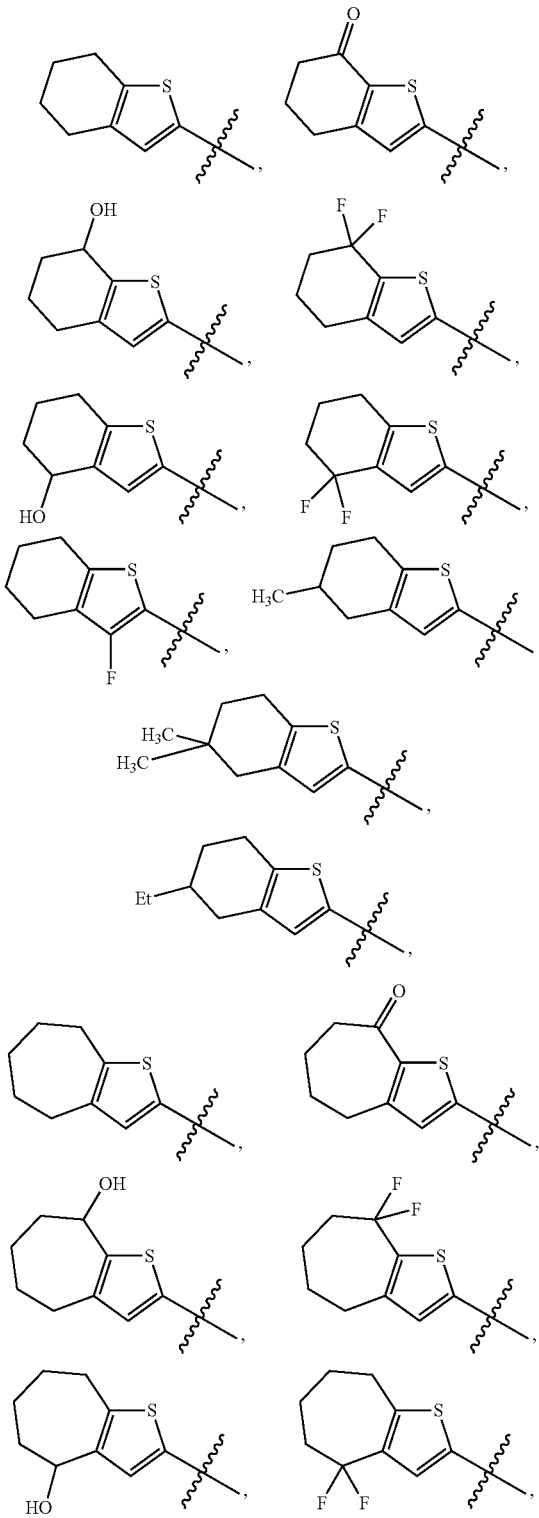

-continued

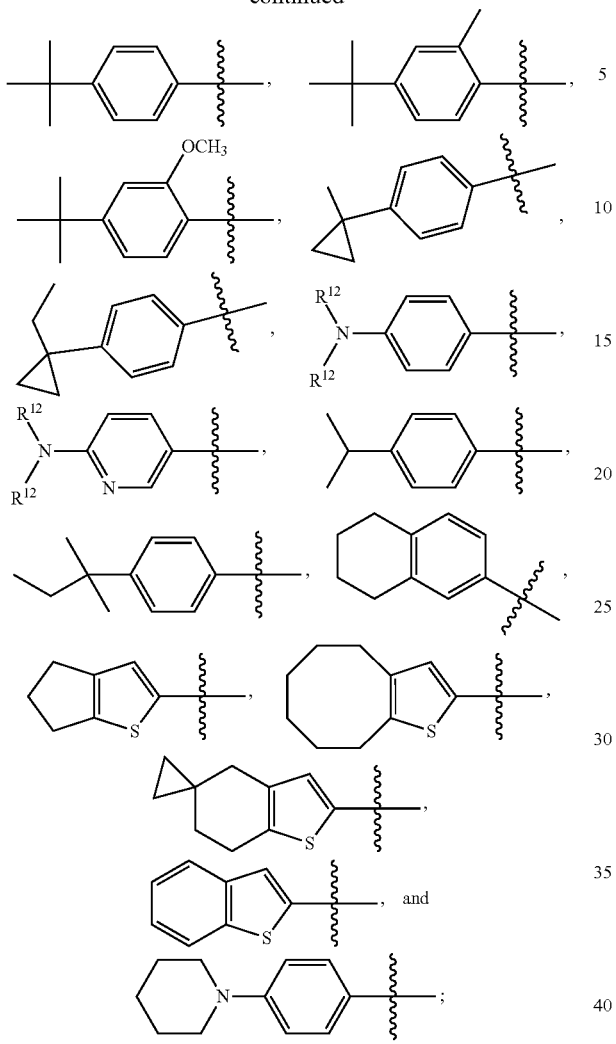

$R^2$ is chosen from H, $CH_3$, F, Cl, CN, $OCH_3$, OH and $CF_3$;
$R^{2'}$ is chosen from H and F;
$R^3$ is chosen from H, $CH_3$, $CF_3$, F, Cl, CN and $OCH_3$;
$R^{3'}$ is chosen from H, $CH_3$, F, Cl, CN and $OCH_3$;
$R^4$ is

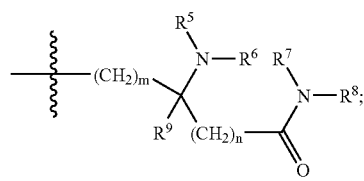

m is chosen from 0 and 1;
n is chosen from 0 and 1;
$R^5$ is chosen from H, $C_1$-$C_6$ alkyl, and $C_3$-$C_6$ cycloalkyl, wherein said alkyl is optionally substituted with one or more substituents chosen from OH, F, and $OCH_3$;
$R^6$ is chosen from H and $C_1$-$C_6$ alkyl; or $R^5$ and $R^6$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl and said cyclic ring is optionally substituted with OH;
$R^7$ is chosen from H, $C_1$-$C_6$ alkyl, and $C_3$-$C_6$ cycloalkyl, wherein said alkyl is optionally substituted with one or more substituents chosen from OH and O($C_1$-$C_4$ alkyl); or $R^6$ and $R^7$ are optionally taken together with the —N($R^5$)C($R^9$)($CH_2$)$_n$C(=O)N($R^8$)— group through the respective nitrogen atoms to which they are directly attached to form a 6-membered cyclic ring;
$R^8$ is chosen from H and $C_1$-$C_6$ alkyl, wherein said alkyl is optionally substituted with one or more substituents chosen from OH, F, and $OCH_3$; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl and said cyclic ring is optionally substituted with OH;
$R^9$ is chosen from H and $CH_3$;
$R^{10}$ is chosen from OH, H and $C_1$-$C_3$ alkyl optionally substituted with N($R^9$)$_2$;
$R^{11}$ is chosen from H, $CH_3$ and $CF_3$; and
$R^{12}$ is $C_1$-$C_3$ alkyl.

2. The compound of claim 1 wherein $R^{11}$ is $CH_3$.
3. The compound of claim 2 wherein W is N and V is CH.
4. The compound of claim 3 wherein X is $CR^2$.
5. The compound of claim 3 wherein X is N.
6. The compound of claim 3 wherein Y is $CR^{3'}$.
7. The compound of claim 3 wherein Y is N.
8. The compound of claim 3 wherein Z is $CR^3$.
9. The compound of claim 3, wherein Z is N.
10. The compound of claim 3, wherein the compound is:

(Formula VIII)

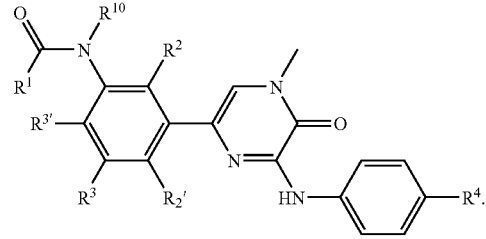

11. The compound of claim 1, wherein $R^{2'}$ is F.
12. The compound of claim 1, wherein $R^{2'}$ is H.
13. The compound of claim 12, wherein $R^1$ is chosen from:

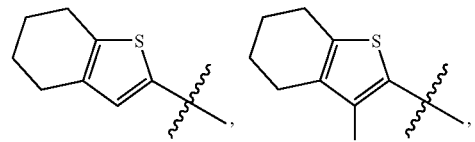

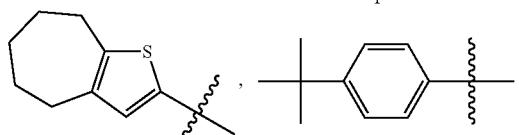

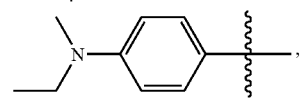

-continued

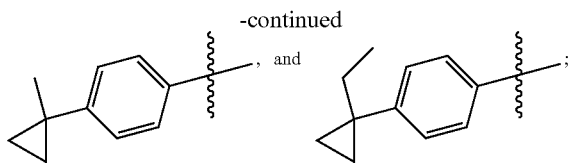, and

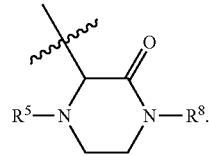

$R^2$ is chosen from H, $CH_3$, F, and Cl;
$R^3$ is chosen from H, $CH_3$, F, and Cl;
$R^{3'}$ is chosen from H, $CH_3$, F and Cl;
$R^5$ is chosen from H and $C_1$-$C_6$ alkyl;
$R^6$ is chosen from H and $C_1$-$C_6$ alkyl; or $R^5$ and $R^6$ are optionally taken together with the nitrogen atom to which they are attached to form a 6-membered cyclic ring having 0-1 additional N, S or O, wherein the optional additional ring nitrogen is optionally substituted with $C_1$-$C_3$ alkyl;
$R^8$ is chosen from H and $C_1$-$C_6$ alkyl; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl;
$R^{10}$ is chosen from H or $C_1$-$C_3$ alkyl; and
$R^{11}$ is $CH_3$.

14. The compound of claim 12, wherein m is 0 and n is 0.
15. The compound of claim 14, wherein $R^1$ is chosen from:

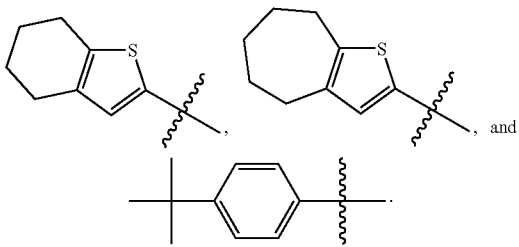

16. The compound of claim 1, wherein $R^2$ is chosen from H, $CH_3$, F and Cl.
17. The compound of claim 1, wherein $R^2$ is chosen from $CH_3$, F, and Cl.
18. The compound of claim 17, wherein $R^2$ is $CH_3$.
19. The compound of claim 16, wherein $R^3$ is chosen from H, $CH_3$, F and Cl.
20. The compound of claim 19, wherein $R^3$ is H.
21. The compound of claim 19, wherein $R^{3'}$ is chosen from H, $CH_3$, F, Cl, CN.
22. The compound of claim 21, wherein $R^{3'}$ is H.
23. The compound of claim 21, wherein $R^5$ is chosen from H and $C_1$-$C_3$ alkyl optionally substituted with OH.
24. The compound of claim 21, wherein $R^5$ is chosen from H and $C_1$-$C_6$ alkyl.
25. The compound of claim 23, wherein $R^6$ is chosen from H and $C_1$-$C_3$ alkyl.
26. The compound of claim 21, wherein $R^5$ and $R^6$ are taken together with the nitrogen atom to which they are attached to form azetidinyl, N-methylpiperazinyl, N-ethylpiperazinyl or morpholinyl.
27. The compound of claim 23, wherein $R^7$ is chosen from H, methyl, ethyl, —$(CH_2)_2$OH and —$(CH_2)_2$$OCH_3$.
28. The compound of claim 23, wherein $R^6$ and $R^7$ are taken together with —N($R^5$)C($R^9$)($CH_2$)$_n$C(=O)N($R^8$)— group through the respective nitrogen atoms to which they are directly attached to form 29. The compound of claim 1, wherein $R^8$ is chosen from H and $C_1$-$C_3$ alkyl.
30. The compound of claim 1, wherein $R^7$ and $R^8$ are taken together with the nitrogen atom to which they are attached to form a 4- to 6-membered cyclic ring having 0-1 additional N, S or O, wherein the optional additional ring nitrogen is optionally substituted with $C_1$-$C_3$ alkyl.
31. The compound of claim 1, wherein $R^7$ and $R^8$ are taken together with the nitrogen atom to which they are attached to form a 4-or 6-membered cyclic ring having 0-1 additional N or O, wherein the optional additional ring nitrogen is optionally substituted with methyl or ethyl and said cyclic ring is optionally substituted with OH.
32. The compound of claim 31, wherein $R^7$ and $R^8$ are taken together with the nitrogen atom to which they are attached to form N-methylpiperazinyl, N-ethylpiperazinyl, morpholinyl, or azetidinyl optionally substituted with OH.
33. The compound of claim 1, wherein $R^9$ is H.
34. The compound of claim 1, wherein $R^{10}$ is chosen from H and $CH_3$.
35. The compound of claim 34, wherein $R^{10}$ is H.
36. The compound of claim 1 chosen from:
N-(3-(6-(4-(1,4-Dimethyl-3-oxopiperazin-2-yl)phenyl amino)-4-methyl-5-oxo-4,5-dihydropyrazin-2-yl)-2-fluorophenyl)-4,5,6,7-tetrahydrobenzo[b]thiophene-2-carboxamide;
N-(3-(6-(4-(1-(Ethyl(isopropyl) amino)-2-((2-methoxyethyl)(methyl)amino)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;
N-(3-(6-(4-(1,2-Bis(4-ethylpiperazin-1-yl)-2-oxoethyl) phenylamino)-4-methyl-5-oxo-4,5-dihydropyrazin-2-yl)-2-methylphenyl)-4,5,6,7-tetrahydrobenzo[b] thiophene-2-carboxamide;
N-(3-(6-(4-(1,2-Bis(4-ethyl piperazin-1-yl)-2-oxoethyl) phenylamino)-4-methyl-5-oxo-4,5-dihydropyrazin-2-yl)-2-methylphenyl)-5,6,7,8-tetrahydro-4H-cyclohepta [b] thiophene-2-carboxamide;
N-(3-(6-(4-(1-Ethyl-4-methyl-3-oxopiperazin-2-yl)phenylamino)-4-methyl-5-oxo-4,5-dihydropyrazin-2-yl)-2-methylphenyl)-4,5,6,7-tetra hydrobenzo[b] thiophene-2-carboxamide;
4-tert-Butyl-N-(3-(6-(4-(1-ethyl-4-methyl-3-oxopiperazin-2-yl)phenylamino)-4-methyl-5-oxo-4,5-dihydro pyrazin-2-yl)-2-methylphenyl)benzamide;
(S)-N-(3-(6-(4-(3-(Dimethyl amino)-2-(isopropyl(methyl)amino)-3-oxopropyl) phenylamino)-4-methyl-5-oxo-4,5-dihydropyrazin-2-yl)-2-methylphenyl)-4,5,6, 7-tetrahydrobenzo[b]thiophene-2-carboxamide;
N-(3-(6-(4-(3-(Dimethylamino)-1-(isopropyl(methyl) amino)-3-oxopropyl)phenyl amino)-4-methyl-5-oxo-4, 5-dihydropyrazin-2-yl)-2-methyl phenyl)-4,5,6,7-tetrahydro benzo [b] thiophene-2-carboxamide;
N-(3-(6-(4-(1-Amino-2-morpholino-2-oxoethyl)phenylamino)-4-methyl-5-oxo-4,5-dihydropyrazin-2-yl)-2-methylphenyl)-4-tert-butylbenzamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4,5,6,7-tetra hydrobenzo[b]thiophene-2-carboxamide;

4-tert-Butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide;

N-(3-(6-(4-(2-Amino-1-(isopropyl(methyl)amino)-2-oxoethyl)phenylamino)-4-methyl-5-oxo-4,5-dihydro pyrazin-2-yl)-2-methylphenyl)-4,5,6,7-tetrahydrobenzo [b]thiophene-2-carboxamide;

N-(2-Methyl-3-(4-methyl-6-(4-(1-methyl-3-oxopiperazin-2-yl)phenylamino)-5-oxo-4,5-dihydropyrazin-2-yl)phenyl)-4,5,6,7-tetrahydrobenzo[b]thiophene-2-carboxamide;

N-(3-(6-(4-(2-(Dimethylamino)-1-(isopropyl(methyl)amino)-2-oxoethyl)phenyl amino)-4-methyl-5-oxo-4,5-dihydro pyrazin-2-yl)-2-methyphenyl)-4,5,6,7-tetrahydrobenzo[b]thiophene-2-carboxamide;

4-tert-Butyl-N-(3-(6-(4-(2-(dimethylamino)-1-(isopropyl(methyl)amino)-2-oxoethyl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenyl amino)-4-methyl-5-oxo-4,5-dihydropyrazin-2-yl)-2,5-difluorophenyl)-4,5,6,7-tetrahydrobenzo[b] thiophene-2-carboxamide;

(S)-4-tert-Butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide;

(R)-4-tert-Butyl-N-(3-(6-(4-(1,4-dimethyl-3-oxopiperazin-2-yl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenylamino)-5-oxo-4,5-dihydro pyrazin-2-yl)-2-methylphenyl)-4-(ethyl(methyl)amino)benzamide;

(R)-N-(3-(6-(4-(2-(Dimethylamino)-1-(isopropyl(methyl)amino)-2-oxoethyl)phenyl amino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(1-ethylcyclopropyl)benzamide;

4-tert-Butyl-N-(3-(6-(4-(1-(4-ethylpiperazin-1-yl)-2-morpholino-2-oxoethyl) phenylamino)-4-methyl-5-oxo-4,5-dihydropyrazin-2-yl)-2-methylphenyl) benzamide;

N-(3-(6-(4-(1-(4-Ethylpiperazin-1-yl)-2-morpholino-2-oxoethyl)phenylamino)-4-methyl-5-oxo-4,5-dihydro pyrazin-2-yl)-2-methylphenyl)-4,5,6,7-tetrahydrobenzo[b] thiophene-2-carboxamide;

N-(3-(6-(4-(1-(4-ethylpiperazin-1-yl)-2-morpholino-2-oxoethyl)phenylamino)-4-methyl-5-oxo-4,5-dihydropyrazin-2-yl)-2-methyl phenyl)-5,6,7,8-tetrahydro-4H-cyclohepta[b]thiophene-2-carboxamide;

N-(3-(6-(4-(1,2-Bis(4-ethyl piperazin-1-yl)-2-oxoethyl) phenylamino)-4-methyl-5-oxo-4,5-dihydropyrazin-2-yl)-2-methylphenyl)-4-tert-butylbenzamide;

4-tert-Butyl-N-(3-(6-(4-(2-(dimethylamino)-1-(4-ethylpiperazin-1-yl)-2-oxoethyl) phenylamino)-4-methyl-5-oxo-4,5-dihydropyrazin-2-yl)-2-methylphenyl) benzamide;

N-(3-(6-(4-(2-(Dimethylamino)-1-(4-ethylpiperazin-1-yl)-2-oxoethyl)phenylamino)-4-methyl-5-oxo-4,5-dihydropyrazin-2-yl)-2-methylphenyl)-4,5,6,7-tetrahydrobenzo[b]thiophene-2-carboxamide;

N-(3-(6-(4-(2-(Dimethylamino)-1-(4-ethylpiperazin-1-yl)-2-oxoethyl)phenylamino)-4-methyl-5-oxo-4,5-dihydro pyrazin-2-yl)-2-methylphenyl)-5,6,7,8-tetrahydro-4H-cyclohepta[b]thiophene-2-carboxamide;

4-tert-Butyl-N-(3-(6-(4-(1-(4-ethylpiperazin-1-yl)-2-((2-methoxyethyl)(methyl) amino)-2-oxoethyl)phenylamino)-4-methyl-5-oxo-4,5-dihydropyrazin-2-yl)-2-methylphenyl)benzamide;

N-(3-(6-(4-(1-(4-Ethylpiperazin-1-yl)-2-((2-methoxyethyl)(methyl)amino)-2-oxoethyl)phenylamino)-4-methyl-5-oxo-4,5-dihydropyrazin-2-yl)-2-methyl phenyl)-4,5,6,7-tetrahydrobenzo[b]thiophene-2-carboxamide;

N-(3-(6-(4-(1-(4-Ethylpiperazin-1-yl)-2-((2-methoxyethyl)(methyl)amino)-2-oxoethyl)phenylamino)-4-methyl-5-oxo-4,5-dihydro pyrazin-2-yl)-2-methylphenyl)-5,6,7,8-tetrahydro-4H-cyclohepta[b]thiophene-2-carboxamide;

N-(3-(6-(4-(1-Isopropyl-4-methyl-3-oxopiperazin-2-yl) phenylamino)-4-methyl-5-oxo-4,5-dihydropyrazin-2-yl)-2-methylphenyl)-4,5,6,7-tetrahydrobenzo[b] thiophene-2-carboxamide;

N-(3-(6-(4-(1,4-Dimethyl-3-oxopiperazin-2-yl)phenylamino)-4-methyl-5-oxo-4,5-dihydropyrazin-2-yl)-2-methylphenyl)-5,6,7,8-tetrahydro-4H-cyclohepta[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-5-fluoro-2-methylphenyl)-4,5,6,7-tetrahydrobenzo[b] thiophene-2-carboxamide;

N-(2-Chloro-3-(6-(4-(1,4-dimethyl-3-oxopiperazin-2-yl) phenylamino)-4-methyl-5-oxo-4,5-dihydropyrazin-2-yl)phenyl)-4,5,6,7-tetrahydrobenzo[b]thiophene-2-carboxamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(ethyl(methyl)amino)benzamide;

N-(3-(6-(4-(1-(Ethyl(isopropyl)amino)-2-morpholino-2-oxoethyl)phenylamino)-4-methyl-5-oxo-4,5-dihydro pyrazin-2-yl)-2-methylphenyl)-4,5,6,7-tetrahydrobenzo[b] thiophene-2-carboxamide;

N-(3-(6-(4-(1-(Ethyl(isopropyl)amino)-2-(4-ethylpiperazin-1-yl)-2-oxoethyl)phenylamino)-4-methyl-5-oxo-4,5-dihydropyrazin-2-yl)-2-methyl phenyl)-4,5,6,7-tetrahydrobenzo[b]thiophene-2-carboxamide;

N-(3-(6-(4-(2-(Dimethylamino)-1-(ethyl(isopropyl) amino)-2-oxoethyl)phenyl mino)-4-methyl-5-oxo-4,5-dihydropyrazin-2-yl)-2-methylphenyl)-4,5,6,7-tetrahydrobenzo[b]thiophene-2-carboxamide;

N-{3-[6-({4-[2-(Azetidin-1-yl)-1-(morpholin-4-yl)-2-oxo ethyl]phenyl }amino)-4-methyl-5-oxo-4,5-dihydro pyrazin-2-yl]-2-methylphenyl }-4,5,6,7-tetrahydro-1-benzothiophene-2-carboxamide;

N-{2-Methyl-3-[4-methyl-6-({4-[(methylcarbamoyl) (morpholin-4-yl)methyl]phenyl}amino)-5-oxo-4,5-dihydropyrazin-2-yl]phenyl}-4,5,6,7-tetrahydro-1-benzothiophene-2-carboxamide;

N-{3-[6-({4-[2-(Azetidin-1-yl)-1-[ethyl(propan-2-yl) amino]-2-oxoethyl]phenyl}amino)-4-methyl-5-oxo-4,5-dihydro pyrazin-2-yl]-2-methylphenyl}-4,5,6,7-tetrahydro-1-benzothiophene-2-carboxamide;

N-{3-[6-({4-[(Dimethyl carbamoyl)[ethyl(propan-2-yl) amino]methyl]phenyl}amino)-4-methyl-5-oxo-4,5-dihydropyrazin-2-yl]-2-methylphenyl}-4H,5H,6H,7H, 8H-cyclohepta[b]thiophene-2-carboxamide;

N-{3-[6-({4-[1-(azetidin-1-yl)-2-(4-ethylpiperazin-1-yl)-2-oxoethyl]phenyl}amino)-4-methyl-5-oxo-4,5-dihydro pyrazin-2-yl]-2-methyl phenyl}-4H,5H,6H,7H, 8H-cyclohepta[b]thiophene-2-carboxamide;

N-[3-(6-{[4-(1,4-Dimethyl-3-oxopiperazin-2-yl)phenyl] amino}-5-oxo-4,5-dihydro pyrazin-2-yl)-2-methylphenyl]-4,5,6,7-tetrahydro-1-benzothiophene-2-carboxamide;

N-{3-[6-({4-[Azetidin-1-yl(dimethylcarbamoyl)methyl] phenyl}amino)-4-methyl-5-oxo-4,5-dihydropyrazin-2-yl]-2-methylphenyl}-4H,5H,6H, 7H,8H-cyclohepta[b]thiophene-2-carboxamide;

N-[2-Methyl-3-(4-methyl-5-oxo-6-{[4-(1,2,4-trimethyl-3-oxopiperazin-2-yl)phenyl]amino}-4,5-dihydropyrazin-2-yl)phenyl]-4,5,6,7-tetrahydro-1-benzothiophene-2-carboxamide;

N-[5-Chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-{3-[6-({4-[Azetidin-1-yl(dimethylcarbamoyl)methyl] phenyl}amino)-4-methyl-5-oxo-4,5-dihydropyrazin-2-yl]-2-methylphenyl}-4-tert-butylbenzamide;

N-{3-[6-({4-[Azetidin-1-yl(dimethylcarbamoyl)methyl] phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{Azetidin-1-yl[(2-hydroxyethyl)(methyl) carbamoyl]methyl}phenyl) amino]-4-methyl-5-oxo-4,5-dihydropyrazin-2-yl}-2-methylphenyl)-4,5,6,7-tetrahydro-1-benzothiophene-2-carboxamide;

N-{2-Methyl-3-[4-methyl-6-({4-[4-methyl-3-oxo-1-(propan-2-yl)piperazin-2-yl]phenyl}amino)-5-oxo-4,5-dihydropyrazin-2-yl]phenyl}-4H,5H,6H,7H,8H-cyclohepta[b]thiophene-2-carboxamide;

N-{3-[6-({4-[(4-Ethyl piperazin-1-yl)[(2-hydroxy ethyl)(methyl)carbamoyl]methyl]phenyl}amino)-4-methyl-5-oxo-4,5-dihydropyrazin-2-yl]-2-methylphenyl}-4H, 5H,6H,7H,8H-cyclohepta[b] thiophene-2-carboxamide;

N-{3-[6-({4-[(Diethyl carbamoyl)(4-ethylpiperazin-1-yl) methyl]phenyl}amino)-4-methyl-5-oxo-4,5-dihydro pyrazin-2-yl]-2-methyl phenyl}-4H,5H,6H,7H,8H-cyclohepta[b]thiophene-2-carboxamide;

4-tert-Butyl-N-(3-{6-[(4-{[ethyl(methyl)carbamoyl](4-ethylpiperazin-1-yl)methyl}phenyl)amino]-4-methyl-5-oxo-4,5-dihydropyrazin-2-yl}-2-methylphenyl) benzamide;

4-tert-Butyl-N-{3-[6-({4-[(diethylcarbamoyl)(4-ethylpiperazin-1-yl)methyl] phenyl} amino)-4-methyl-5-oxo-4, 5-dihydropyrazin-2-yl]-2-methylphenyl}benzamide;

N-[3-(6-{[4-(1,4-Dimethyl-3-oxopiperazin-2-yl)phenyl] amino }-5-oxo-4,5-dihydropyrazin-2-yl)-2-methylphenyl]-N-methyl-4,5,6,7-tetrahydro-1-benzothiophene-2-carboxamide;

4-tert-Butyl-N-(2-methyl-3-{4-methyl-6-[(4-{1-[methyl (propan-2-yl)amino]-2-(morpholin-4-yl)-2-oxoethyl } phenyl)amino]-5-oxo-4,5-dihydropyrazin-2-yl}phenyl)benzamide;

N-{3-[6-({4-[2-(Azetidin-1-yl)-1-[methyl(propan-2-yl) amino]-2-oxoethyl]phenyl}amino)-4-methyl-5-oxo-4, 5-dihydropyrazin-2-yl]-2-methylphenyl}-4-tert-butylbenzamide;

N-{3-[6-({4-[1-(Azetidin-1-yl)-2-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{Azetidin-1-yl[(2-hydroxyethyl)(methyl) carbamoyl]methyl}phenyl) amino]-4-methyl-5-oxo-4, 5-dihydropyrazin-2-yl}-2-methylphenyl)-4H,5H,6H, 7H, 8H-cyclohepta[b]thiophene-2-carboxamide;

4-tert-Butyl-N-(2-methyl-3-{4-methyl-6-[(4-{1-[methyl (propan-2-yl)amino]-2-(4-methylpiperazin-1-yl)-2-oxoethyl}phenyl)amino]-5-oxo-4,5-dihydropyrazin-2-yl}phenyl)benzamide;

N-(3-(6-(4-(1,4-Dimethyl-3-oxopiperazin-2-yl)phenyl amino)-4-methyl-5-oxo-4,5-dihydropyrazin-2-yl)-2-methylphenyl)-4-(1-methylcyclopropyl)benzamide;

N-(3-(6-(4-(1-Ethyl-4-methyl-3-oxopiperazin-2-yl)phenyl amino)-4-methyl-5-oxo-4,5-dihydropyrazin-2-yl)-2-methylphenyl)-5,6,7,8-tetrahydro-4H-cyclohepta[b]thiophene-2-carboxamide;

4-tert-Butyl-N-(3-(6-(4-(1-isopropyl-4-methyl-3-oxopiperazin-2-yl)phenylamino)-4-methyl-5-oxo-4,5-dihydropyrazin-2-yl)-2-methylphenyl)benzamide;

N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo [b]thiophene-2-carboxamide;

(S)-N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo [b]thiophene-2-carboxamide;

(R)-N-(3-(6-(4-(1,4-Dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide; and (S)-(+)-N-(3-(6-(4-(2-(Dimethylamino)-1-(isopropyl(methyl)amino)-2-oxoethyl)phenylamino)-4-methyl-5-oxo-4,5-dihydropyrazin-2-yl)-2-methylphenyl)-4,5,6, 7-tetrahydrobenzo[b]thiophene-2-carboxamide;

N-[3-(6-{[4-(1,4-dimethyl-3-oxopiperazin-2-yl)phenyl] amino}-4-methyl-5-oxo-4,5-dihydropyrazin-2-yl)-2-methylphenyl]-N-methyl-4,5,6,7-tetrahydro-1-benzothiophene-2-carboxamide;

N-(3-{6-[(4-{1-[ethyl(methyl)amino]-2-(4-ethylpiperazin-1-yl)-2-oxoethyl}phenyl)amino]-4-methyl-5-oxo-4,5-dihydropyrazin-2-yl}-2-methylphenyl)-4H,5H,6H, 7H,8H-cyclohepta[b]thiophene-2-carboxamide;

N-[3-(6-{[4-(1,4-dimethyl-3-oxopiperazin-2-yl)phenyl] amino}-4-methyl-5-oxo-4,5-dihydropyrazin-2-yl)-2-methylphenyl]-6-[ethyl(methyl)amino]pyridine-3-carboxamide;

N-[3-(6-{[4-(1,4-dimethyl-3-oxopiperazin-2-yl)phenyl] amino}-4-methyl-5-oxo-4,5-dihydropyrazin-2-yl)-2-fluoro-5-methylphenyl]-4,5,6,7-tetrahydro-1-benzothiophene-2-carboxamide;

N-{3-[6-({4-[2-(azetidin-1-yl)-1-[methyl(propan-2-yl) amino]-2-oxoethyl]phenyl}amino)-4-methyl-5-oxo-4, 5-dihydropyrazin-2-yl]-2-methylphenyl}-4H,5H,6H, 7H,8H-cyclohepta[b]thiophene-2-carboxamide;

N-[3-(6-{[4-(1,4-dimethyl-3-oxopiperazin-2-yl)phenyl] amino}-4-methyl-5-oxo-4,5-dihydropyrazin-2-yl)phenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2-methylphenyl]-4H,5H,6H,7H,8H-cyclohepta[b] thiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,5-dimethylphenyl]-4,5,6,7-tetrahydro-1-benzothiophene-2-carboxamide;

N-[5-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-{3-[6-({4-[(dimethylcarbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide;

N-{3-[6-({4-[(diethylcarbamoyl)(morpholin-4-yl)methyl]phenyl}amino)-4-methyl-5-oxo-4,5-dihydropyrazin-2-yl]-2-methylphenyl}-4,5,6,7-tetrahydro-1-benzothiophene-2-carboxamide;

N-(3-{6-[(4-{[ethyl(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide;

N-(3-{6-[(4-{[(2-hydroxyethyl)(methyl)carbamoyl](morpholin-4-yl)methyl}phenyl)amino]-4-methyl-5-oxo-4,5-dihydropyrazin-2-yl}-2-methylphenyl)-4,5,6,7-tetrahydro-1-benzothiophene-2-carboxamide;

N-{3-[6-({4-[2-(3-hydroxyazetidin-1-yl)-1-(morpholin-4-yl)-2-oxoethyl]phenyl}amino)-4-methyl-5-oxo-4,5-dihydropyrazin-2-yl]-2-methylphenyl}-4,5,6,7-tetrahydro-1-benzothiophene-2-carboxamide;

N-{3-[6-({4-[(dimethylcarbamoyl)(morpholin-4-yl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[(diethylcarbamoyl)(morpholin-4-yl)methyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{3-[6-({4-[2-(azetidin-1-yl)-1-(morpholin-4-yl)-2-oxoethyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

N-{2-methyl-3-[4-methyl-6-({4-[(methylcarbamoyl)(morpholin-4-yl)methyl]phenyl}amino)-5-oxo-4,5-dihydropyrazin-2-yl]phenyl}-4H,5H,6H,7H,8H-cyclohepta[b]thiophene-2-carboxamide;

N-(3-{6-[(4-{[ethyl(methyl)carbamoyl](morpholin-4-yl)methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

N-(3-{6-[(4-{[(2-hydroxyethyl)(methyl)carbamoyl](morpholin-4-yl)methyl}phenyl)amino]-4-methyl-5-oxo-4,5-dihydropyrazin-2-yl}-2-methylphenyl)-4H,5H,6H,7H,8H-cyclohepta[b]thiophene-2-carboxamide;

N-{3-[6-({4-[2-(3-hydroxyazetidin-1-yl)-1-(morpholin-4-yl)-2-oxoethyl]phenyl}amino)-4-methyl-5-oxo-4,5-dihydropyrazin-2-yl]-2-methylphenyl}-4H,5H,6H,7H,8H-cyclohepta[b]thiophene-2-carboxamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methoxybenzamide;

N-[2-chloro-3-(6-{[4-(1,4-dimethyl-3-oxopiperazin-2-yl)phenyl]amino}-4-methyl-5-oxo-4,5-dihydropyrazin-2-yl)-5-methylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,6-dimethylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-5-methoxy-2-methylphenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[2,6-dichloro-3-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[6-chloro-3-(6-{[4-(1,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[2-chloro-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[2-chloro-3-(6-{[4-(1,4-dimethyl-3-oxopiperazin-2-yl)phenyl]amino}-4-methyl-5-oxo-4,5-dihydropyrazin-2-yl)-6-fluorophenyl]-4,5,6,7-tetrahydro-1-benzothiophene-2-carboxamide;

N-[2-cyano-5-(6-{[4-(1,4-dimethyl-3-oxopiperazin-2-yl)phenyl]amino}-4-methyl-5-oxo-4,5-dihydropyrazin-2-yl)phenyl]-4,5,6,7-tetrahydro-1-benzothiophene-2-carboxamide;

N-[4-(6-{[4-(1,4-dimethyl-3-oxopiperazin-2-yl)phenyl]amino}-4-methyl-5-oxo-4,5-dihydropyrazin-2-yl)-6-fluoropyridin-2-yl]-4,5,6,7-tetrahydro-1-benzothiophene-2-carboxamide;

4-tert-butyl-N-{3-[6-({4-[(S)-(dimethylcarbamoyl)[methyl(propan-2-yl)amino]methyl]phenyl}amino)-4-methyl-5-oxo-4,5-dihydropyrazin-2-yl]-2-methylphenyl}benzamide;

4-tert-butyl-N-{3-[6-({4-[(R)-(dimethylcarbamoyl)[methyl(propan-2-yl)amino]methyl]phenyl}amino)-4-methyl-5-oxo-4,5-dihydropyrazin-2-yl]-2-methylphenyl}benzamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-N-[3-(dimethylamino)propyl]benzamide;

N-[6-chloro-3-(6-{[4-(1,4-dimethyl-3-oxopiperazin-2-yl)phenyl]amino}-4-methyl-5-oxo-4,5-dihydropyrazin-2-yl)-2-methylphenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)pyridin-3-yl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)pyridin-2-yl]-4,5,6,7-tetrahydro-1-benzothiophene-2-carboxamide;

N-[2-chloro-3-(6-{[4-(1,4-dimethyl-3-oxopiperazin-2-yl)phenyl]amino}-4-methyl-5-oxo-4,5-dihydropyrazin-2- yl)-6-methylphenyl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1,4-dimethyl-3-oxopiperazin-2-yl)phenyl]amino}-4-methyl-5-oxo-4,5-dihydropyrazin-2-yl)-5-fluoropyridin-2-yl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-oxo-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-methylphenyl]-7-hydroxy-4,5,6,7-tetrahydro-1-benzothiophene-2-carboxamide;

4-tert-butyl-N-[3-(6-{[4-(1,4-dimethyl-3-oxopiperazin-2-yl)phenyl]amino}-4-methyl-5-oxo-4,5-dihydropyrazin-2-yl)-2-methylphenyl]-2-methylbenzamide;

N-[3-(6-{[4-(1-ethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[3-(6-{[4-(1-ethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[3-(6-{[4-(1-ethyl-4-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(4-ethyl-1-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

4-tert-butyl-N-[6-(6-{[4-(1,4-dimethyl-3-oxopiperazin-2-yl)phenyl]amino}-4-methyl-5-oxo-4,5-dihydropyrazin-2-yl)pyridin-2-yl]benzamide;

N-[5-(6-{[4-(1-ethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[5-(6-{[4-(1,4-diethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-7,7-difluoro-4,5,6,7-tetrahydro-1-benzothiophene-2-carboxamide;

N-[5-(6-{[4-(1-ethyl-4-methyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-[6-(6-{[4-(1-ethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(4-ethyl-1-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1-ethyl-4-methyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[6-(6-{[4-(1,4-diethyl-3-oxopiperazin-2-yl)phenyl]amino}-4-methyl-5-oxo-4,5-dihydropyrazin-2-yl)-3-fluoropyridin-2-yl]-4,5,6,7-tetrahydro-1-benzothiophene-2-carboxamide;

N-[3-(6-{[4-(1,4-diethyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[3-(6-{[4-(4-ethyl-1-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-{5-[6-({4-[(2R)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide;

N-[3-(6-{[4-(1,4-diethyl-3-oxopiperazin-2-yl)phenyl]amino}-4-methyl-5-oxo-4,5-dihydropyrazin-2-yl)-2,6-difluorophenyl]-4,5,6,7-tetrahydro-1-benzothiophene-2-carboxamide;

N-{5-[6-({4-[(2S)-1,4-dimethyl-3-oxopiperazin-2-yl]phenyl}amino)-4-methyl-5-oxo-4,5-dihydropyrazin-2-yl]-2-fluorophenyl}-4,5,6,7-tetrahydro-1-benzothiophene-2-carboxamide;

N-{6-[6-({4-[(2S)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide;

N-{6-[6-({4-[(2R)-1,4-dimethyl-3-oxopiperazin-2-yl]phenyl}amino)-4-methyl-5-oxo-4,5-dihydropyrazin-2-yl]-3-fluoropyridin-2-yl}-4,5,6,7-tetrahydro-1-benzothiophene-2-carboxamide;

N-[2-fluoro-5-(4-methyl-6-{[4-(4-methyl-3-oxopiperazin-2-yl)phenyl]amino}-5-oxo-4,5-dihydropyrazin-2-yl)phenyl]-4,5,6,7-tetrahydro-1-benzothiophene-2-carboxamide;

N-[3-(6-{[4-(1,4-dimethyl-3-oxopiperazin-2-yl)phenyl]amino}-4-methyl-5-oxo-4,5-dihydropyrazin-2-yl)-2-fluoro-6-methylphenyl]-4,5,6,7-tetrahydro-1-benzothiophene-2-carboxamide;

N-[3-(6-{[4-(1-ethyl-4-methyl-3-oxopiperazin-2-yl)phenyl]amino}-4-methyl-5-oxo-4,5-dihydropyrazin-2-yl)-6-fluoro-2-methylphenyl]-4,5,6,7-tetrahydro-1-benzothiophene-2-carboxamide;

N-[5-(6-{[4-(2,4-dimethyl-3-oxopiperazin-2-yl)phenyl]amino}-4-methyl-5-oxo-4,5-dihydropyrazin-2-yl)-2-fluorophenyl]-4,5,6,7-tetrahydro-1-benzothiophene-2-carboxamide;

N-{5-[6-({4-[2-(azetidin-1-yl)-1-(dimethylamino)-2-oxoethyl]phenyl}amino)-4-methyl-5-oxo-4,5-dihydropyrazin-2-yl]-2-fluorophenyl}-4,5,6,7-tetrahydro-1-benzothiophene-2-carboxamide;

N-{2-fluoro-5-[6-({4-[1-(2-hydroxyethyl)-4-methyl-3-oxopiperazin-2-yl]phenyl}amino)-4-methyl-5-oxo-4,5-dihydropyrazin-2-yl]phenyl}-4,5,6,7-tetrahydro-1-benzothiophene-2-carboxamide;

N-[5-(6-{[4-(1,4-dimethyl-3-oxopiperazin-2-yl)phenyl]amino}-4-methyl-5-oxo-4,5-dihydropyrazin-2-yl)-2-fluorophenyl]-4,4-difluoro-4,5,6,7-tetrahydro-1-benzothiophene-2-carboxamide;

N-[3-(6-{[4-(1,4-dimethyl-3-oxopiperazin-2-yl)phenyl]
amino}-4-methyl-5-oxo-4,5-dihydropyrazin-2-yl)-2-
methylphenyl]-4-hydroxy-4,5,6,7-tetrahydro-1-ben-
zothiophene-2-carboxamide; and N-[3-(5-{[5-(1,4-dimethyl-3-oxopiperazin-2-yl)pyridin-
2-yl]amino}-1-methyl-6-oxo-1,6-dihydropyridin-3-
yl)-2-methylphenyl]-4,5,6,7-tetrahydro-1-ben-
zothiophene-2-carboxamide.

37. A pharmaceutical composition, comprising a compound of claim 1, together with at least one pharmaceutically acceptable vehicle chosen from carriers, adjuvants, and excipients.

38. A pharmaceutical composition of claim 37, wherein the composition is formulated in a form chosen from injectable fluids, aerosols, creams, gels, tablets, pills, capsules, syrups, ophthalmic solutions, and transdermal patches.

39. A packaged pharmaceutical composition, comprising
a pharmaceutical composition of claim 37; and
instructions for using the composition to treat a patient suffering from a disease responsive to inhibition of Btk activity.

40. The packaged pharmaceutical composition of claim 39 wherein the disease responsive to inhibition of Btk activity is cancer.

41. The packaged pharmaceutical composition of claim 39 wherein the disease responsive to inhibition of Btk activity is chosen from bone disorders, allergic disorders, autoimmune diseases, inflammatory diseases, and acute inflammatory reactions.

42. A method for determining the presence of Btk in a sample, comprising contacting the sample with a compound of claim 1 under conditions that permit detection of Btk activity, detecting a level of Btk activity in the sample, and therefrom determining the presence or absence of Btk in the sample.

43. A method for decreasing B-cell activity comprising contacting cells expressing Btk with a compound of claim 1, in an amount sufficient to detectably decrease B-cell activity in vitro.

44. A compound of Formula I, or a pharmaceutically acceptable salt or mixture thereof:

(Formula I)

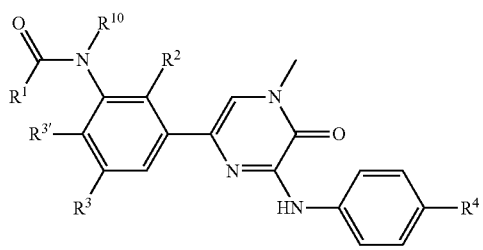

wherein
$R^1$ is chosen from:

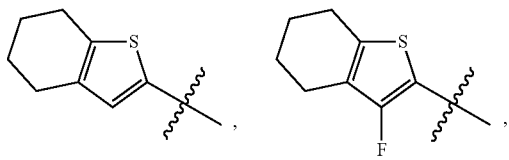

-continued $R^2$ is chosen from H, $CH_3$, F, and Cl;
$R^3$ is chosen from H, $CH_3$, F and Cl;
$R^{3'}$ is chosen from H, $CH_3$, F and Cl;
$R^4$ is m is 0 or 1;
n is 0 or 1;
$R^5$ is H or $C_1$-$C_6$ alkyl;
$R^6$ is H or $C_1$-$C_6$ alkyl; or $R^5$ and $R^6$ are optionally taken together with the nitrogen atom to which they are attached to form a 6-membered cyclic ring having 0-1 additional N, S or O, wherein the optional additional ring nitrogen is optionally substituted with $C_1$-$C_3$ alkyl;
$R^7$ is H or $C_1$-$C_6$ alkyl wherein said alkyl is optionally substituted with one or more substituents chosen from OH and O($C_1$-$C_4$ alkyl); or $R^6$ and $R^7$ are optionally taken together with the —N($R^5$)C($R^9$)(CH$_2$)$_n$C(=O)N($R^8$)— group through the respective nitrogen atoms to which they are directly attached to form a 6-membered cyclic ring;
$R^8$ is H or $C_1$-$C_6$ alkyl; or $R^7$ and $R^8$ are optionally taken together with the nitrogen atom to which they are attached to form a 4- to 6-membered cyclic ring having 0-1 additional N, S or O, wherein the optional additional ring nitrogen is optionally substituted with $C_1$-$C_3$ alkyl;
$R^9$ is H or $CH_3$; and
$R^{10}$ is H or $CH_3$.

* * * * *